(12) United States Patent
Tabuteau

(10) Patent No.: US 9,901,589 B2
(45) Date of Patent: *Feb. 27, 2018

(54) COMPOSITIONS FOR ORAL ADMINISTRATION OF ZOLEDRONIC ACID OR RELATED COMPOUNDS FOR TREATING COMPLEX REGIONAL PAIN SYNDROME

(71) Applicant: ANTECIP BIOVENTURES II LLC, New York, NY (US)

(72) Inventor: Herriot Tabuteau, New York, NY (US)

(73) Assignee: ANTECIP BIOVENTURES II LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/416,995

(22) Filed: Jan. 26, 2017

(65) Prior Publication Data

US 2017/0136046 A1   May 18, 2017

Related U.S. Application Data

(63) Continuation-in-part of application No. 15/164,651, filed on May 25, 2016, which is a continuation of application No. 15/055,386, filed on Feb. 26, 2016, now abandoned, which is a continuation of application No. 14/635,857, filed on Mar. 2, 2015, now Pat. No. 9,283,239, which is a continuation of application No. 14/279,232, filed on May 15, 2014, now Pat. No. 9,149,487, which is a continuation of application No. 14/063,979, filed on Oct. 25, 2013, now Pat. No. 8,802,658, which is a continuation-in-part of application No. 13/894,274, filed on May 14, 2013, now abandoned, application No. 15/416,995, which is a continuation-in-part of application No. 15/347,696, filed on Nov. 9, 2016, which is a continuation-in-part of application No. PCT/US2015/032739, filed on May 27, 2015.

(60) Provisional application No. 61/646,538, filed on May 14, 2012, provisional application No. 61/647,478, filed on May 15, 2012, provisional application No. 61/654,292, filed on Jun. 1, 2012, provisional application No. 61/654,383, filed on Jun. 1, 2012, provisional application No. 61/655,527, filed on Jun. 5, 2012, provisional application No. 61/655,541, filed on Jun. 5, 2012, provisional application No. 61/764,563, filed on Feb. 14, 2013, provisional application No. 61/762,225, filed on Feb. 7, 2013, provisional application No. 61/767,647, filed on Feb. 21, 2013, provisional application No. 61/767,676, filed on Feb. 21, 2013, provisional application No. 61/803,721, filed on Mar. 20, 2013.

(51) Int. Cl.
*A61K 31/675*    (2006.01)
*A61K 9/00*    (2006.01)
*A61K 31/56*    (2006.01)
*A61K 9/28*    (2006.01)

(52) U.S. Cl.
CPC .......... *A61K 31/675* (2013.01); *A61K 9/0053* (2013.01); *A61K 9/28* (2013.01); *A61K 31/56* (2013.01)

(58) Field of Classification Search
None
See application file for complete search history.

(56) References Cited

U.S. PATENT DOCUMENTS

| | | |
|---|---|---|
| 4,939,130 A | 7/1990 | Jaeggi et al. |
| 5,869,471 A | 2/1999 | Hovancik et al. |
| 6,015,801 A | 1/2000 | Daifotis |
| 6,419,955 B1 | 7/2002 | Gabel et al. |
| 6,943,155 B2 | 9/2005 | Lichtenberger |
| 7,658,939 B2 | 2/2010 | Oshlack et al. |
| 7,704,977 B2 | 4/2010 | Leonard |
| 8,053,429 B2 | 11/2011 | Cumming et al. |
| 8,119,159 B2 | 2/2012 | Cumming et al. |
| 8,323,689 B2 | 12/2012 | Cumming et al. |
| 8,323,690 B2 | 12/2012 | Cumming et al. |
| 8,399,023 B2 | 3/2013 | Hanna et al. |
| 8,772,267 B2 | 7/2014 | Pappagallo |
| 8,802,658 B2 | 8/2014 | Tabuteau |
| 8,822,436 B1 | 9/2014 | Tabuteau |
| 8,828,431 B2 | 9/2014 | Cumming et al. |
| 8,835,650 B1 | 9/2014 | Tabuteau |
| 8,859,530 B2 | 10/2014 | Desai |

(Continued)

FOREIGN PATENT DOCUMENTS

| | | |
|---|---|---|
| CN | 101259133 | 3/2008 |
| EP | 1057488 | 12/2000 |

(Continued)

OTHER PUBLICATIONS

US Food and Drug Administration, Pharmacology Review of ZOMETA®, 261 pgs., Nov. 2001, available at: http://www.accessdata.fda.gov/drugsatfda_docs/nda/2001/21-223_Zometa.cfm.
US Food and Drug Administration, Severe Pain with Osteoporosis Drugs; FDA patient safety news: Show #73, 1 pg., Mar. 2008, available at: http://www.fda.govklownloads/Safety/FDAPatientSafetyNews/UCM417867.pdf.
U.S. Appl. No. 13/894,244, filed May 14, 2013 First Named Inventor: Herriot Tabuteau Assignee: Antecip Bioventures II LLC.
U.S. Appl. No. 13/894,252, filed May 14, 2013 First Named Inventor: Herriot Tabuteau Assignee: Antecip Bioventures II LLC.

(Continued)

*Primary Examiner* — Robert A Wax
*Assistant Examiner* — Quanglong N Truong
(74) *Attorney, Agent, or Firm* — Maschoff Brennan; Brent A. Johnson; Yuefen Zhou

(57) ABSTRACT

Oral dosage forms of osteoclast inhibitors, such as nitrogen-containing bisphosphonates, such as zoledronic acid in an acid or a salt form can be used to treat or alleviate pain or related conditions, such as complex regional pain syndrome.

30 Claims, 17 Drawing Sheets

(56) References Cited

U.S. PATENT DOCUMENTS

| | | |
|---|---|---|
| 8,865,757 B1 | 10/2014 | Tabuteau |
| 8,883,201 B2 | 11/2014 | Leonard |
| 8,883,203 B2 | 11/2014 | Leonard |
| 8,901,161 B1 | 12/2014 | Tabuteau |
| 8,901,162 B1 | 12/2014 | Tabuteau |
| 8,933,057 B2 | 1/2015 | Hanna et al. |
| 8,962,599 B1 | 2/2015 | Tabuteau |
| 9,006,279 B1 | 4/2015 | Tabuteau |
| 9,034,889 B2 | 5/2015 | Tabuteau |
| 9,079,927 B1 | 7/2015 | Tabuteau |
| 9,149,487 B2 | 10/2015 | Tabuteau |
| 9,169,279 B2 | 10/2015 | Hanna et al. |
| 9,205,045 B1 | 12/2015 | Tabuteau |
| 9,211,257 B2 | 12/2015 | Tabuteau |
| 9,216,153 B2 | 12/2015 | Tabuteau |
| 9,216,168 B1 | 12/2015 | Tabuteau |
| 9,265,778 B2 | 2/2016 | Tabuteau |
| 9,278,106 B2 | 3/2016 | Tabuteau |
| 9,283,239 B2 | 3/2016 | Tabuteau |
| 9,289,384 B2 | 3/2016 | Tabuteau |
| 9,289,385 B2 | 3/2016 | Tabuteau |
| 9,289,441 B2 | 3/2016 | Tabuteau |
| 9,290,575 B2 | 3/2016 | Tabuteau |
| 9,301,964 B2 | 4/2016 | Tabuteau |
| 9,408,860 B2 | 8/2016 | Tabuteau |
| 9,408,861 B2 | 8/2016 | Tabuteau |
| 9,408,862 B2 | 8/2016 | Tabuteau |
| 9,427,403 B2 | 8/2016 | Tabuteau |
| 9,511,081 B2 | 12/2016 | Tabuteau |
| 9,517,242 B2 | 12/2016 | Tabuteau |
| 9,522,157 B2 | 12/2016 | Tabuteau |
| 9,539,268 B2 | 1/2017 | Tabuteau |
| 9,585,901 B2 | 3/2017 | Tabuteau |
| 9,585,902 B2 | 3/2017 | Tabuteau |
| 9,610,300 B2 | 4/2017 | Tabuteau |
| 9,616,077 B2 | 4/2017 | Tabuteau |
| 9,616,078 B2 | 4/2017 | Tabuteau |
| 9,623,036 B2 | 4/2017 | Tabuteau |
| 9,623,037 B2 | 4/2017 | Tabuteau |
| 9,623,038 B2 | 4/2017 | Tabuteau |
| 9,655,908 B2 | 5/2017 | Tabuteau |
| 9,662,343 B2 | 5/2017 | Tabuteau |
| 9,669,040 B2 | 6/2017 | Tabuteau |
| 9,675,626 B2 | 6/2017 | Tabuteau |
| 9,694,023 B2 | 7/2017 | Tabuteau |
| 9,700,570 B2 | 7/2017 | Tabuteau |
| 9,707,245 B2 | 7/2017 | Tabuteau |
| 9,707,247 B2 | 7/2017 | Tabuteau |
| 9,717,747 B2 | 8/2017 | Tabuteau et al. |
| 9,770,457 B2 | 9/2017 | Tabuteau |
| 9,782,421 B1 | 10/2017 | Tabuteau |
| 9,789,128 B2 | 10/2017 | Tabuteau |
| 2004/0063670 A1* | 4/2004 | Fox ............... A61K 31/663 514/102 |
| 2005/0026871 A1 | 2/2005 | Flashner-Barak et al. |
| 2005/0054616 A1 | 3/2005 | Aronhime et al. |
| 2005/0260262 A1 | 11/2005 | Tabuteau |
| 2006/0068010 A1 | 3/2006 | Turner et al. |
| 2007/0134319 A1 | 6/2007 | Zannou et al. |
| 2009/0281064 A1 | 11/2009 | Ahmed et al. |
| 2010/0121040 A1 | 5/2010 | Tabuteau |
| 2010/0215743 A1 | 8/2010 | Leonard |
| 2011/0028435 A1 | 2/2011 | Hanna et al. |
| 2011/0098252 A1 | 4/2011 | Pappagallo |
| 2012/0190647 A1 | 7/2012 | Hanna et al. |
| 2013/0035315 A1 | 2/2013 | Hanna et al. |
| 2013/0274282 A1 | 10/2013 | Tabuteau |
| 2013/0303485 A1 | 11/2013 | Tabuteau |
| 2013/0303486 A1 | 11/2013 | Tabuteau |
| 2013/0303487 A1 | 11/2013 | Tabuteau |
| 2013/0303488 A1 | 11/2013 | Tabuteau |
| 2014/0051669 A1 | 2/2014 | Tabuteau |
| 2014/0051718 A1 | 2/2014 | Tabuteau |
| 2014/0107345 A1 | 4/2014 | Tabuteau |
| 2014/0249107 A1 | 9/2014 | Tabuteau |
| 2014/0249108 A1 | 9/2014 | Tabuteau |
| 2014/0249109 A1 | 9/2014 | Tabuteau |
| 2014/0249110 A1 | 9/2014 | Tabuteau |
| 2014/0249111 A1 | 9/2014 | Tabuteau |
| 2014/0249112 A1 | 9/2014 | Tabuteau |
| 2014/0249113 A1 | 9/2014 | Tabuteau |
| 2014/0249317 A1 | 9/2014 | Tabuteau |
| 2014/0256683 A1 | 9/2014 | Tabuteau |
| 2014/0329773 A1 | 11/2014 | Tabuteau |
| 2014/0348916 A1 | 11/2014 | Tabuteau |
| 2014/0349974 A1 | 11/2014 | Tabuteau |
| 2015/0051175 A1 | 2/2015 | Tabuteau |
| 2015/0057250 A1 | 2/2015 | Tabuteau |
| 2015/0133403 A1 | 5/2015 | Tabuteau |
| 2015/0141373 A1 | 5/2015 | Tabuteau |
| 2015/0141374 A1 | 5/2015 | Tabuteau |
| 2015/0148312 A1 | 5/2015 | Tabuteau |
| 2015/0157564 A1 | 6/2015 | Tabuteau |
| 2015/0164929 A1 | 6/2015 | Tabuteau |
| 2015/0216884 A1 | 8/2015 | Tabuteau |
| 2015/0344505 A1 | 12/2015 | Tabuteau |
| 2015/0361179 A1 | 12/2015 | Tabuteau |
| 2016/0038517 A1 | 2/2016 | Tabuteau |
| 2016/0095871 A1 | 4/2016 | Tabuteau |
| 2016/0095872 A1 | 4/2016 | Tabuteau |
| 2016/0113950 A1 | 4/2016 | Tabuteau |
| 2016/0151398 A1 | 6/2016 | Tabuteau |
| 2016/0158254 A1 | 6/2016 | Tabuteau |
| 2016/0158255 A1 | 6/2016 | Tabuteau |
| 2016/0158256 A1 | 6/2016 | Tabuteau |
| 2016/0166589 A1 | 6/2016 | Tabuteau |
| 2016/0166590 A1 | 6/2016 | Tabuteau |
| 2016/0175333 A1 | 6/2016 | Tabuteau |
| 2016/0199394 A1 | 7/2016 | Tabuteau |
| 2016/0199395 A1 | 7/2016 | Tabuteau |
| 2016/0206636 A1 | 7/2016 | Tabuteau |
| 2016/0235772 A1 | 8/2016 | Tabuteau |
| 2016/0263134 A1 | 9/2016 | Tabuteau |
| 2016/0296539 A1 | 10/2016 | Tabuteau |
| 2016/0324882 A1 | 11/2016 | Tabuteau |
| 2016/0331679 A1 | 11/2016 | Tabuteau |
| 2016/0331766 A1 | 11/2016 | Tabuteau |
| 2016/0331767 A1 | 11/2016 | Tabuteau |
| 2016/0331768 A1 | 11/2016 | Tabuteau |
| 2017/0042914 A1 | 2/2017 | Tabuteau |
| 2017/0049791 A1 | 2/2017 | Tabuteau |
| 2017/0056425 A1 | 3/2017 | Tabuteau |
| 2017/0056426 A1 | 3/2017 | Tabuteau |
| 2017/0056427 A1 | 3/2017 | Tabuteau |
| 2017/0065620 A1 | 3/2017 | Tabuteau |
| 2017/0065621 A1 | 3/2017 | Tabuteau |
| 2017/0065622 A1 | 3/2017 | Tabuteau |
| 2017/0065623 A1 | 3/2017 | Tabuteau |
| 2017/0065624 A1 | 3/2017 | Tabuteau |
| 2017/0065625 A1 | 3/2017 | Tabuteau |
| 2017/0071958 A1 | 3/2017 | Tabuteau |
| 2017/0071960 A1 | 3/2017 | Tabuteau |
| 2017/0079995 A1 | 3/2017 | Tabuteau |
| 2017/0079996 A1 | 3/2017 | Tabuteau |
| 2017/0079997 A1 | 3/2017 | Tabuteau |
| 2017/0079998 A1 | 3/2017 | Tabuteau |
| 2017/0087168 A1 | 3/2017 | Tabuteau |
| 2017/0087169 A1 | 3/2017 | Tabuteau |
| 2017/0095486 A1 | 4/2017 | Tabuteau |
| 2017/0095487 A1 | 4/2017 | Tabuteau |
| 2017/0095488 A1 | 4/2017 | Tabuteau |
| 2017/0100416 A1 | 4/2017 | Tabuteau |
| 2017/0100417 A1 | 4/2017 | Tabuteau |
| 2017/0119801 A1 | 5/2017 | Tabuteau |
| 2017/0128470 A1 | 5/2017 | Tabuteau |
| 2017/0128472 A1 | 5/2017 | Tabuteau |
| 2017/0136046 A1 | 5/2017 | Tabuteau |
| 2017/0143747 A1 | 5/2017 | Tabuteau |
| 2017/0157039 A1 | 6/2017 | Tabuteau |
| 2017/0157152 A1 | 6/2017 | Tabuteau |
| 2017/0157153 A1 | 6/2017 | Tabuteau |
| 2017/0172917 A1 | 6/2017 | Tabuteau |
| 2017/0173054 A1 | 6/2017 | Tabuteau |
| 2017/0182072 A1 | 6/2017 | Tabuteau |

(56) References Cited

U.S. PATENT DOCUMENTS

| | | |
|---|---|---|
| 2017/0209469 A1 | 7/2017 | Tabuteau |
| 2017/0216324 A1 | 8/2017 | Tabuteau |
| 2017/0224710 A1 | 8/2017 | Tabuteau |
| 2017/0232018 A1 | 8/2017 | Tabuteau |
| 2017/0252299 A1 | 9/2017 | Tabuteau |
| 2017/0252361 A1 | 9/2017 | Tabuteau |
| 2017/0260144 A1 | 9/2017 | Tabuteau |
| 2017/0266209 A1 | 9/2017 | Tabuteau |
| 2017/0281654 A1 | 10/2017 | Tabuteau |
| 2017/0281655 A1 | 10/2017 | Tabuteau |
| 2017/0281656 A1 | 10/2017 | Tabuteau |

FOREIGN PATENT DOCUMENTS

| | | |
|---|---|---|
| WO | 1999015155 | 4/1999 |
| WO | 2000028954 | 5/2000 |
| WO | 2002043738 | 1/2002 |
| WO | 2002087555 | 11/2002 |
| WO | 2003075741 | 9/2003 |
| WO | 2004035061 | 4/2004 |
| WO | 2005063218 | 7/2005 |
| WO | 2005072747 | 8/2005 |
| WO | 2005107751 | 11/2005 |
| WO | 2005115331 | 12/2005 |
| WO | 2005115406 | 12/2005 |
| WO | 2006102117 | 9/2006 |
| WO | 2011014781 | 2/2011 |
| WO | 2012071517 | 5/2012 |
| WO | 2013173330 | 11/2013 |

OTHER PUBLICATIONS

U.S. Appl. No. 13/894,262, filed May 14, 2013 First Named Inventor: Herriot Tabuteau Assignee: Antecip Bioventures II LLC.
U.S. Appl. No. 14/894,274, filed May 14, 2013 First Named Inventor: Herriot Tabuteau Assignee: Antecip Bioventures II LLC.
U.S. Appl. No. 14/063,979, filed Oct. 25, 2013 First Named Inventor: Herriot Tabuteau Assignee: Antecip Bioventures II LLC.
U.S. Appl. No. 14/106,291, filed Dec. 13, 2013 First Named Inventor: Herriot Tabuteau Assignee: Antecip Bioventures II LLC.
U.S. Appl. No. 14/279,196, filed May 15, 2014 First Named Inventor: Herriot Tabuteau Assignee: Antecip Bioventures II LLC.
U.S. Appl. No. 14/279,206, filed May 15, 2014 First Named Inventor: Herriot Tabuteau Assignee: Antecip Bioventures II LLC.
U.S. Appl. No. 14/279,213, filed May 15, 2014 First Named Inventor: Herriot Tabuteau Assignee: Antecip Bioventures II LLC.
U.S. Appl. No. 14/279,222, filed May 15, 2014 =first Named Inventor: Herriot Tabuteau Assignee: Antecip Bioventures II LLC.
U.S. Appl. No. 14/279,226, filed May 15, 2014 First Named Inventor: Herriot Tabuteau Assignee: Antecip Bioventures II LLC.
U.S. Appl. No. 14/279,229, filed May 15, 2014 First Named Inventor: Herriot Tabuteau Assignee: Antecip Bioventures II LLC.
U.S. Appl. No. 14/279,232, filed May 15, 2014 First Named Inventor: Herriot Tabuteau Assignee: Antecip Bioventures II LLC.
U.S. Appl. No. 14/279,236, filed May 15, 2014 First Named Inventor: Herriot Tabuteau Assignee: Antecip Bioventures II LLC.
U.S. Appl. No. 14/279,241, filed May 15, 2014 First Named Inventor: Herriot Tabuteau Assignee: Antecip Bioventures II LLC.
U.S. Appl. No. 14/288,241, filed May 27, 2014 First Named Inventor: Herriot Tabuteau Assignee: Antecip Bioventures II LLC.
U.S. Appl. No. 14/288,713, filed May 28, 2014 First Named Inventor: Herriot Tabuteau Assignee: Antecip Bioventures II LLC.
U.S. Appl. No. 14/288,716, filed May 28, 2014 First Named Inventor: Herriot Tabuteau Assignee: Antecip Bioventures II LLC.
U.S. Appl. No. 14/288,720, filed May 28, 2014 First Named Inventor: Herriot Tabuteau Assignee: Antecip Bioventures II LLC.
U.S. Appl. No. 14/310,811, filed Jun. 20, 2014 First Named Inventor: Herriot Tabuteau Assignee: Antecip Bioventures II LLC.
U.S. Appl. No. 14/336,642, filed Jul. 21, 2014 First Named Inventor: Herriot Tabuteau Assignee: Antecip Bioventures II LLC.
U.S. Appl. No. 14/446,184, filed Jul. 29, 2014 First Named Inventor: Herriot Tabuteau Assignee: Antecip Bioventures II LLC.
U.S. Appl. No. 14/456,939, filed Aug. 11, 2014 First Named Inventor: Herriot Tabuteau Assignee: Antecip Bioventures II LLC.
U.S. Appl. No. 14/457,659, filed Aug. 12, 2014 First Named Inventor: Herriot Tabuteau Assignee: Antecip Bioventures II LLC.
U.S. Appl. No. 14/481,097, filed Sep. 9, 2014 First Named Inventor: Herriot Tabuteau Assignee: Antecip Bioventures II LLC.
U.S. Appl. No. 14/530,556, filed Oct. 31, 2014 First Named Inventor: Herriot Tabuteau Assignee: Antecip Bioventures II LLC.
U.S. Appl. No. 14/536,526, filed Nov. 7, 2014 First Named Inventor: Herriot Tabuteau Assignee: Antecip Bioventures II LLC.
U.S. Appl. No. 14/538,709, filed Nov. 11, 2014 First Named Inventor: Herriot Tabuteau Assignee: Antecip Bioventures II LLC.
U.S. Appl. No. 14/540,333, filed Nov. 13, 2014 First Named Inventor: Herriot Tabuteau Assignee: Antecip Bioventures II LLC.
U.S. Appl. No. 14/604,524, filed Jan. 23, 2015 First Named Inventor: Herriot Tabuteau Assignee: Antecip Bioventures II LLC.
U.S. Appl. No. 14/605,822, filed Jan. 26, 2015 First Named Inventor: Herriot Tabuteau Assignee: Antecip Bioventures II LLC.
U.S. Appl. No. 14/607,947, filed Jan. 28, 2015 First Named Inventor: Herriot Tabuteau Assignee: Antecip Bioventures II LLC.
U.S. Appl. No. 14/607,985, filed Jan. 28, 2015 First Named Inventor: Herriot Tabuteau Assignee: Antecip Bioventures II LLC.
U.S. Appl. No. 14/608,855, filed Jan. 29, 2015 First Named Inventor: Herriot Tabuteau Assignee: Antecip Bioventures II LLC.
U.S. Appl. No. 14/625,457, filed Feb. 18, 2015 First Named Inventor: Herriot Tabuteau Assignee: Antecip Bioventures II LLC.
U.S. Appl. No. 14/635,857, filed Mar. 2, 2015 First Named Inventor: Herriot Tabuteau Assignee: Antecip Bioventures II LLC.
U.S. Appl. No. 14/639,013, filed Mar. 13, 2015 First Named Inventor: Herriot Tabuteau Assignee: Antecip Bioventures II LLC.
U.S. Appl. No. 14/686,551, filed Apr. 14, 2015 First Named Inventor: Herriot Tabuteau Assignee: Antecip Bioventures II LLC.
U.S. Appl. No. 14/967,224, filed Dec. 11, 2015 First Named Inventor: Herriot Tabuteau Assignee: Antecip Bioventures II LLC.
U.S. Appl. No. 14/967,234, filed Dec. 11, 2015 First Named Inventor: Herriot Tabuteau Assignee: Antecip Bioventures II LLC.
U.S. Appl. No. 14/968,514, filed Dec. 14, 2015 First Named Inventor: Herriot Tabuteau Assignee: Antecip Bioventures II LLC.
U.S. Appl. No. 15/009,712, filed Jan. 28, 2016 First Named Inventor: Herriot Tabuteau Assignee: Antecip Bioventures II LLC.
U.S. Appl. No. 15/014,994, filed Feb. 3, 2016 First Named Inventor: Herriot Tabuteau Assignee: Antecip Bioventures II LLC.
U.S. Appl. No. 15/042,017, filed Feb. 11, 2016 First Named Inventor: Herriot Tabuteau Assignee: Antecip Bioventures II LLC.
U.S. Appl. No. 15/043,141, filed Feb. 12, 2016 First Named Inventor: Herriot Tabuteau Assignee: Antecip Bioventures II LLC.
U.S. Appl. No. 15/043,281, filed Feb. 12, 2016 First Named Inventor: Herriot Tabuteau Assignee: Antecip Bioventures II LLC.
U.S. Appl. No. 15/043,419, filed Feb. 12, 2016 First Named Inventor: Herriot Tabuteau Assignee: Antecip Bioventures II LLC.
U.S. Appl. No. 15/055,386, filed Feb. 26, 2016 First Named Inventor: Herriot Tabuteau Assignee: Antecip Bioventures II LLC.
Laslett et al., Zoledronic Acid Reduces Knee Pain and Bone Marrow Lesions over 1 Year: A Randomized Controlled Trial, Annals of the Rheumatic Diseases, 71(8), 1322-1328, Aug. 2012.
Leonard et al., MER-101 Tablets: A Pilot Bioavailability Study of a Novel Oral Formulation of Zoledronic Acid, Poster Presentation, Molecular Targets and Cancer Therapeutics, San Francisco, CA, USA, Oct. 22-26, 2007.
Leonard et al., Safety Profile of Zoledronic Acid in a Novel Oral Formulation, Poster Presentation, Molecular Targets & Cancer Therapeutics Conference, Boston, MA, USA, Nov. 15-19, 2009.
Leonard et al., Studies of Bioavailability and Food Effects of MER-101 Zoledronic Acid Tablets in Postmenopausal Women, Poster Presentation, ASCO Breast Cancer Symposium, San Francisco, CA, USA, Oct. 2009.
Lipton et al., The New Bisphosphonate, Zometa (Zoledronic Acid), Decreases Skeletal Complications in Both Osteolytic and Osteoblastic Lesions: A Comparison to Pamidronate, Cancer Investigation, 20(Supp 2), 45-54, Jan. 2002.

(56) References Cited

OTHER PUBLICATIONS

Miaillefert et al., Treatment of Refractory Reflex Sympathetic Dystrophy with Pamidronate, Annals of the Rhematic Diseases, 54(8), 687, Sep. 1995.
Maksymowych et al., A Six-Month Randomized, Controlled, Double-Blind, Dose-Response Comparison of Intravenous Pamidronate (60 mg versus 10 mg) in the Treatment of Nonsteroidal Antiinflammatory Drug-Refractory Ankylosing Spondylitis, Arthritis & Rheumatism, 46(3), 766-773, Mar. 2002.
Manicourt et al., Role of Alendronate in Therapy for Posttraumatic Complex Regional Pain Syndrome Type 1 of the Lower Extremity, Rheumatoid & Arthritis, 50(11), 3690-3697, Nov. 2004.
Marinus et al., Clinical Features and Pathophysiology of Complex Regional Pain Syndrome, The Lancet Neurology, 10(7), 637-648, Jul. 2011.
Matsuo et al., Antiinflammatory and Chondroprotective Effects of the Aminobisphosphonate Incadronate (YM175) in Adjuvant Induced Arthritis, abstract, The Journal of rheumatology, 30(6), 1280-1290, Jun. 2003.
Mc Hugh et al., MER-101-03, A Multi Center, Phase II Study to Compare MER-101 20 mg Tablets to Intravenous ZOMETA® 4 mg in Prostate Cancer Patients, Abstract and Presentation, American Society of Clinical Oncology Annual Meeting, Orlando, FL, USA, May 29-Jun. 2, 2009.
Merck & Co., Inc., Highlights of Prescribing Information for FOSAMAX® (Alendronate Sodium) Tablets for Oral Use, last revised Feb. 2012, 24 pgs., available at http://www.accessdata.fda.gov/drugsatfda_docs/label/2012/021575s017lbl.pdf.
Merrion Pharmaceuticals, ORAZOL®: Novel Approach to Adjuvant Therapy for Improving Outcomes in Breast Cancer, Presentation, 15 pgs., Apr. 2011, last accessed at http://www.merrionpharma.com/archive/presentations/ORAZOLPresentationQ12011.pdf.
Munns et al., Acute Phase Response and Mineral Status Following Low Dose Intravenous Zoledronic Acid in Children, Bone, 41(3), 366-370, Sep. 2007.
Nagae et al., Acidic Microenvironment Created by Osteoclasts Causes Bone Pain Associated with Tumor Colonization, Journal of Bone and Mineral Metabolism, 25(2), 99-104, Mar. 2007.
Nagae et al., Osteoclasts Play a Part in Pain Due to the Inflammation Adjacent to Bone, Bone, 39(5), 1107-1115, Nov. 2006.
Nath et al., Reflex Sympathetic Dystrophy. The Controversy Continues, Clinics in Plastic Surgery, 23(3), 435-446, Jul. 1996.
National Health Service, Complex Regional Pain Syndrome, 11 pgs., Jul. 27, 2012.
Novartis Pharmaceutical Corporation, Highlights of Prescribing Information for RECLAST® (Zoledronic Acid), Injection, 28 pgs., last revised Apr. 2013, available at http://www.accessdata.fda.gov/drugsatfda_docs/label/2013/021817s015lbl.pdf.
Novartis Pharmaceutical Corporation, Highlights of Prescribing Information for ZOMETA® (Zoledronic Acid), Injection, 22 pgs., last revised Mar. 2012.
Novartis Pharmaceutical Corporation, RECLAST® Medication Guide, 4 pgs., Aug. 2011.
Orcel et al., Bisphosphonates in Bone Diseases Other than Osteoporosis, Joint Bone Spine, 69(1), 19-27, Jan. 2002.
Orcel, Response, Joint Bone Spine, 69(5), 522, Oct. 2002.
Oura et al., Bisphosphonate Therapy for Bone Metastases from Breast Cancer: Clinical Results and a New Therapeutic Approach, abstract, Breast Cancer, 7(4), 307-310, Oct. 2000.
Perez et al., Evidence Based Guideline for Complex Regional Pain Syndrome Type 1, BMC Neurology, 10(1), 14 pgs., Mar. 2010.
Podworny et al., Partial Chondroprotective Effect of Zoledronate in a Rabbit Model of Inflammatory Arthritis, abstract, The Journal of Rheumatology, 26(9), 1972-1982, Sep. 1999.
Reflex Sympathetic Dystropy Syndrome Association, Complex Regional Pain Syndrome: Treatment Guidelines, 74 pgs., Jun. 2006.
Reginster et al., Evaluation of the Efficacy and Safety of Oral Tiludronate in Paget's Disease of Bone, abstract, Arthritis & Rheumatism, 35(8), 967-974, Aug. 1992.
Rehman et al., Treatment of Reflex Sympathetic Dystrophy with Intravenous Pamidronate, Abstract P36, Bone and Tooth Society Meeting, p. 116, Apr. 1991.
Binge et al., A Review of Bone Pain Relief with Ibandronate and Other Bisphosphonates in Disorders of Increased Bone Turnover, Clinical and Experimental Rheumatology, 25(5), 766-774, Sep. 2007.
Ringe, Development of Clinical Utility of Zoledronic Acid and Patient Consideration in the Treatment of Osteoporosis, Patient Preference and Adherence, 4, 231-245, Jul. 2010.
Ripamonti et al., Decreases in Pain at Rest and Movement-Related Pain During Zoledronic Acid Treatment in Patients with Bone Metastases due to Breast or Prostate Cancer: A Pilot Study, Support Care in Cancer, 15(10), 1177-1184, Oct. 2007.
Robinson et al., Efficacy of Pamidronate in Complex Regional Pain Syndrome Type I, Pain Medicine, 5(3), 276-280, Sep. 2004.
Rovetta et al., Efficacy of Disodium-Clodronate in the Management of Joint Pain in Rheumatoid Arthritis. Six Months Open Study, abstract, Minerva Medica, 94(5), 353-7, Oct. 2003.
Russell et al., Mechanisms of Action of Bisphosphonates: Similarities and Differences and Their Potential Influence on Clinical Efficacy, Osteoporosis International, 19(6), 733-759, Jun. 2008.
Schinkel et al., Inflammatory Mediators are Altered in the Acute Phase of Posttraumatic Complex Regional Pain Syndrome, Clinical Journal of Pain, 22(3), 235-239, Mar.-Apr. 2006.
Schott, Bisphosphonates for Pain Relief in Reflex Sympathetic Dystrophy?, The Lancet, 350(9085), 1117, Oct. 1997.
Sebastian, Complex Regional Pain Syndrome, Indian Journal of Plastic Surgery, 44(2), 298-307, May 2011.
Seok et al., Treatment of Transient Osteoporosis of the Hip with Intravenous Zoledronate, Annals of Rehabilitation Medicine, 35(3), 432-435, Jun. 2011.
Sevcik et al., Bone Cancer Pain: the Effects of the Bisphosphonate Alendronate on Pain, Skeletal Remodeling, Tumor Growth and Tumor Necrosis, Pain, 111(1-2), 169-180, Sep. 2004.
Sharma et al., Advances in Treatment of Complex Regional Pain Syndrome: Recent Insights on a Perplexing Disease, Current Opinion in Anesthesiology, 19(5), 566-572, Oct. 2006.
Siminoski et al., Intravenous Pamidronate for Treatment of Reflex Sympathetic Dystrophy During Breast Feeding, Journal of Bone and Mineral Research, 15(10), 2052-2055, Oct. 2000.
Simm et al., The Successful Use of Pamidronate in an 11-year-old Girl with Complex Regional Pain Syndrome: Response to Treatment Demonstrated by Serial Peripheral Quantitative Computerised Tomographic Scan, Bone, 46(4), 885-888, Apr. 2010.
Slobodin et al., The Synergistic Efficacy of Adalimumab and Pamidronate in a Patient with Ankylosing Spondylitis, Clinical Rheumatology, 29(7), 793-794, Jul. 2010.
Sorbera et al., Zoledronate Disodium, Drugs of the Future, 25(3), 259-268, Mar. 2000.
Stanton-Hicks et al., Complex Regional Pain Syndromes: Guidelines for Therapy, The Clinical Journal of Pain, 14(2), 155-166, Jun. 1998.
The University of Sheffiled, Health and Economic Impact of a New Drug Intervention for Osteoporosis, 2 pgs., last accessed Jun. 2014, available at http://www.sheffield.ac.uk/humanmetabolism/researchandyou/zoledronicacid.
The Use of Zoledronic Acid to Complex Regional Pain Syndrome (Aclasta), ClinicalTrials.gov, 3 pgs., last accessed on Feb. 8, 2013, available at: http://clinicaltrials.gov/ct2/show/NCT01788176.
Tran et al., Treatment of Complex Regional Pain Syndrome: A Review of the Evidence, Canadian Journal of Anesthesia, 57(2), 149-166, Feb. 2010.
U.S. Appl. No. 15/074,367, filed Mar. 18, 2016 First Named Inventor: Herriot Tabuteau Assignee: Antecip Bioventures II LLC.
U.S. Appl. No. 15/074,380, filed Mar. 18, 2016 FirstNamed Inventor: Herriot Tabuteau Assignee: Antecip Bioventures II LLC.
U.S. Appl. No. 15/083,105, filed Mar. 28, 2016 First Named Inventor: Herriot Tabuteau Assignee: Antecip Bioventures II LLC.
U.S. Appl. No. 15/136,092, filed Apr. 22, 2016 First Named Inventor: Herriot Tabuteau Assignee: Antecip Bioventures II LLC.
U.S. Appl. No. 15/164,651, filed May 25, 2016 First Named Inventor: Herriot Tabuteau Assignee: Antecip Bioventures II LLC.

(56) References Cited

OTHER PUBLICATIONS

U.S. Appl. No. 15/188,725, filed Jun. 21, 2016 First Named Inventor: Herriot Tabuteau Assignee: Antecip Bioventures II LLC.
U.S. Appl. No. 15/211,827, filed Jul. 15, 2016 First Named Inventor: Herriot Tabuteau Assignee: Antecip Bioventures II LLC.
U.S. Appl. No. 15/217,752, filed Jul. 22, 2016 First Named Inventor: Herriot Tabuteau Assignee: Antecip Bioventures II LLC.
U.S. Appl. No. 15/217,773, filed Jul. 22, 2016 First Named Inventor: Herriot Tabuteau Assignee: Antecip Bioventures II LLC.
U.S. Appl. No. 15/223,487, filed Jul. 29, 2016 First Named Inventor: Herriot Tabuteau Assignee: Antecip Bioventures II LLC.
U.S. Appl. No. 15/223,548, filed Jul. 29, 2016 First Named Inventor: Herriot Tabuteau Assignee: Antecip Bioventures II LLC.
Turner-Stokes et al., Complex Regional Pain Syndrome in Adults: Concise Guidance, Clinical Medicine, 11(6), 596-600, Dec. 2011.
US Food and Drug Administration, CRPS Orphan Drug Designation for Zoledronic Acid, 1 pg., May 6, 2013, available at http://www.accessdata.fda.gov/scripts/opdlisting/oopd/OOPD_Results_2.cfm?Index_Number=374112.
Van Beek et al., Binding and Antiresorptive Properties of Heterocycle-Containing Bisphosphonate Analogs: Structure-Activity Relationships, Bone, 23(5), 437-442, Nov. 1998.
Van Offel et al., Influence of Cyclic Intravenous Pamidronate on Proinflammatory Monocytic Cytokine Profiles and Bone Density in Rheumatoid Arthritis Treated with Low Dose Prednisolone and Methrotrexate, Clinical and Experimental Rheumatology, 19(1), 13-20, Jan. 2001.
Varenna et al., Intravenous Clodronate in the Treatment of Reflex Sympathetic Dystrophy Syndrome. A Randomized, Double Blind, Placebo Controlled Study, The Journal of Rheumatology, 27(6), 1477-1483, Jun. 2000.
Varenna et al., Treatment of Complex Regional Pain Syndrome Type I with Neridronate: A Randomized, Double-Blind, Placebo-Controlled Study, Rheumatology, 534-542, Nov. 2012.
Nalker et al., Disease Modifying and Anti-Nociceptive Effects of the Bisphosphonate, Zoledronic Acid in a Model of Bone Cancer Pain, Pain, 100(3), 219-229, Dec. 2002.
Yanow et al., Complex Regional Pain Syndrome (CRPS/RSD) and Neuropathic Pain: Role of Intravenous Bisphosphonates as Analgesics, The Scientific World Journal, 8, 229-236, Feb. 2008.
Zaspel et al., Treatment of Early Stage CRPS I—Cortisone (Methylprednisolone) Versus Bisphosphonate (Zoledronic Acid), German Congress of Orthopedics and Traumatology, Berlin, DE, Oct. 24-27, 2007.
Zhang et al., Modic Changes: A Systematic Review of the Literature, European Spine Journal, 17(10), 1289-1299, Oct. 2008.
Altman et al., Low Back Pain in Paget's Disease of Bone, Clinical Orthopedic and Related Research, 217, 152-161, Apr. 1987.
Hendren et al., A Review of the Differences Between Normal and Osteoarthritis Articular Cartilage in Human Knee and Ankle Joints, The Foot, 19(3), 171-176, Sep. 2009.
McHugh et al., MER-101 Tablets: A Pilot Bioavailability Study of a Novel Oral Formulation of Zoledronic Acid, Molecular Cancer Therapeutics, Nov., 2007; B194.
U.S. Appl. No. 15/246,325, filed Aug. 24, 2016 First Named Inventor: Herriot Tabuteau Assignee: Antecip Bioventures II LLC.
U.S. Appl. No. 15/335,381, filed Oct. 26, 2016 First Named Inventor: Herriot Tabuteau Assignee: Antecip Bioventures II LLC.
U.S. Appl. No. 15/347,696, filed Nov. 9, 2016 First Named Inventor: Herriot Tabuteau Assignee: Antecip Bioventures II LLC.
U.S. Appl. No. 15/348,808, filed Nov. 10, 2016 First Named Inventor: Herriot Tabuteau Assignee: Antecip Bioventures II LLC.
U.S. Appl. No. 15/348,842, filed Oct. 26, 2016 First Named Inventor: Herriot Tabuteau Assignee: Antecip Bioventures II LLC.
U.S. Appl. No. 15/349,926, filed Nov. 11, 2016 First Named Inventor: Herriot Tabuteau Assignee: Antecip Bioventures II LLC.
U.S. Appl. No. 15/352,461, filed Nov. 15, 2016 First Named Inventor: Herriot Tabuteau Assignee: Antecip Bioventures II LLC.
U.S. Appl. No. 15/353,550, filed Nov. 16, 2016 First Named Inventor: Herriot Tabuteau Assignee: Antecip Bioventures II LLC.
U.S. Appl. No. 15/354,862, filed Nov. 17, 2016 First Named Inventor: Herriot Tabuteau Assignee: Antecip Bioventures II LLC.
U.S. Appl. No. 15/354,908, filed Nov. 17, 2016 First Named Inventor: Herriot Tabuteau Assignee: Antecip Bioventures II LLC.
U.S. Appl. No. 15/356,434, filed Nov. 18, 2016 First Named Inventor: Herriot Tabuteau Assignee: Antecip Bioventures II LLC.
U.S. Appl. No. 15/357,769, filed Nov. 21, 2016 First Named Inventor: Herriot Tabuteau Assignee: Antecip Bioventures II LLC.
U.S. Appl. No. 15/357,932, filed Nov. 21, 2016 First Named Inventor: Herriot Tabuteau Assignee: Antecip Bioventures II LLC.
U.S. Appl. No. 15/360,886, filed Nov. 23, 2016 First Named Inventor: Herriot Tabuteau Assignee: Antecip Bioventures II LLC.
U.S. Appl. No. 15/364,117, filed Nov. 29, 2016 First Named Inventor: Herriot Tabuteau Assignee: Antecip Bioventures II LLC.
U.S. Appl. No. 15/365,748, filed Nov. 30, 2016 First Named Inventor: Herriot Tabuteau Assignee: Antecip Bioventures II LLC.
U.S. Appl. No. 15/367,048, filed Dec. 1, 2016 First Named Inventor: Herriot Tabuteau Assignee: Antecip Bioventures II LLC.
U.S. Appl. No. 15/368,355, filed Dec. 2, 2016 First Named Inventor: Herriot Tabuteau Assignee: Antecip Bioventures II LLC.
U.S. Appl. No. 15/371,052, filed Dec. 6, 2016 First Named Inventor: Herriot Tabuteau Assignee: Antecip Bioventures II LLC.
U.S. Appl. No. 15/377,907, filed Dec. 13, 2016 First Named Inventor: Herriot Tabuteau Assignee: Antecip Bioventures II LLC.
U.S. Appl. No. 15/378,939, filed Dec. 14, 2016 First Named Inventor: Herriot Tabuteau Assignee: Antecip Bioventures II LLC.
U.S. Appl. No. 15/380,824, filed Dec. 15, 2016 First Named Inventor: Herriot Tabuteau Assignee: Antecip Bioventures II LLC.
U.S. Appl. No. 15/384,125, filed Dec. 19, 2016 First Named Inventor: Herriot Tabuteau Assignee: Antecip Bioventures II LLC.
Marmo et al., Experimental analysis of certain pharmacodynamic features of ketoprofen lysine, Archive for Medical Sciences, 137, 387-395, 1980. (English Translation).
Varenna, Efficacy Study of Neridronate to Treat Painful Osteoarthritis of the Knee With Bone Marrow Lesions, ClinicalTrials.gov, 3 pgs., last accessed on Mar. 13, 2013, available at: https://clinicaltrials.gov/ct2/show/NCT01803360.
Grunenthal GmbH, Efficacy and Safety of Intravenous Neridronic Acid in CRPS-I, ClinicalTrials.gov, 6 pgs., last accessed on Nov. 11, 2016, available at: https://clinicaltrials.gov/ct2/show/NCT02402530.
Abe et al., Improvement of Pain and Regional Osteoporotic Changes in the Foot and Ankle by Low Dose Bisphosphonate Therapy for Complex Regional Pain Syndrome Type I: A Case Series, Journal of Medical Case Reports, 5(1), 349-354, Aug. 2011.
Adami et al., Bisphosphonate Therapy of Reflex Sympathetic Dystrophy Syndrome, Annals of Rheumatic Diseases, 56(3), 201-204, Mar. 1997.
Allen et al., Cancer Treatment Dosing Regimens of Zoledronic Acid Result in Near-Complete Suppression of Mandible Intracortical Bone Remodeling in Beagle Dogs, Journal of Bone and Mineral Research, 25(1), 98-105, Jan. 2010.
Bingham et al., Risedronate Decreases Biochemical Markers of Cartilage Degradation but Does Not Decrease Symptoms or Slow Radiographic Progression in Patients with Medical Compartment Osteoarthritis of the Knee, Arthritis & Rheumatism, 54(11), 3494-3507, Nov. 2006.
Bonabello et al., Analgesic Effect of Bisphosphonates in Mice, Pain, 91(3), 269-275, Apr. 2001.
Bonefos Product Monograph, Part III: Consumer Information Bonefos® clodronate isodium, 25-28, revised Sep. 22, 2011, last accessed http://www.bayer.ca/files/BONEFOS-PM-ENG-PT3-22SEP2011-147998.pdf.
Breuer et al., An Open-Label Pilot Trial of Ibandronate for Complex Regional Pain Syndrome, The Clinical Journal of Pain, 24(8), 685-689, Oct. 2008.
Bruehl, An Update on the Pathophysiology of Complex Regional Pain Syndrome, Anesthesiology, 113(3), 713-725, Sep. 2010.
Brunner et al., Biphosphonates for the Therapy of Complex Regional Pain Syndrome I—Systematic Review, European Journal of Pain, 13(1), 17-21, Jan. 2009.

(56) References Cited

OTHER PUBLICATIONS

Cantatore et al., Evaluation of Bone Turnover and Osteoclastic Cytokines in Early Rheumatoid Arthritis Treated with Alendronate, The Journal of Rheumatology, 26(11), 2318-2323, Nov. 1999.
Capello et al., Meta-Analysis of Imaging Techniques for the Diagnosis of Complex Regional Pain Syndrome Type I, Journal of Hand Surgery, 37(2), 288-296, Feb. 2012.
Cecchini et al., Bisphosphonates In Vitro Specifically Inhibit, Among the Hematopoietic Series, the Development of the Mouse Mononuclear Phagocyte Lineage, Journal of Bone and Mineral Research, 5(10), 1019-1027, Oct. 1990.
Chauvineau et al., What is the Place of Diphosphonates in the Treatment of Complex Regional Pain Syndrom I? A Literature Review, Annales de Readaptation et de Medecine Physique, 48(3), 150-157, Apr. 2005.
Clere, CRPS: Evidence Still Needed for Biphosphonates, Douleurs Evaluation—Diagnostic—Traitement 10(4), 214-215, Sep. 2009.
Conte et al., Safety of Intravenous and Oral Bisphosphonates and Compliance with Dosing Regimens, The Oncologist, 9 (Suppl 4), 28-37, Sep. 2004.
Cortet et al., Treatment of Severe, Recalcitrant Reflex Sympathetic Dystrophy: Assessment of Efficacy and Safety of the Second Generation Bisphosphonate Pamidronate, Clinical Rheumatology, 16(1), 51-56, Jan. 1997.
Cremers et al., Pharmacokinetics/Pharmacodynamics of Bisphosphonates, Clinical Pharmacokinetics, 44(6), 551-570, Jun. 2005.
Oullen et al., MER-101: A Bioavailability Study of Various GIPET™ Formulations in Beagle Dogs with Intraduodenal Cannulae, Abstract T3147, American Association of Pharmaceutical Scientists (AAPS), San Diego, CA, USA, Nov. 12-16, 2007.
De Castro et al., Zoledronic Acid to Treat Complex Regional Pain Syndrome Type I in Adult (Case Report), Revista Dor Pesquisa Clinica e Terapêutica, Sao Paulo, 12(1), 71-73, Jan.-Mar. 2011.
De Mos et al., Outcome of the Complex Regional Pain Syndrome, The Clinical Journal of Pain, 25(7), 590-597, Sep. 2009.
De Mos et al., The Association Between ACE Inhibitors and the Complex Regional Pain Syndrome: Suggestions for a Neuro-Inflammatory Pathogenesis of CRPS, Pain, 142(3), 218-224, Apr. 2009.
Devogelaer et al., Dramatic Improvement of Interactable Reflex Sympathetic Dystrophy Syndrome by Intravenous Infusions of the Second Generation Bisphosphonate APD., Abstract 213, 3(suppl), S122, Tenth Annual Meeting of the American Society for Bone and Mineral Research, New Orleans, LA, USA, Jun. 4-7, 1988.
Driban et al., Evaluation of Bone Marrow Lesion Volume as a Knee Osteoarthritis Biomarker—Longitudinal Relationships with Pain and Structural Changes: Data from the Osteoarthritis Initiative, Arthritis Research & Therapy, 15(5):R112, 11 pgs., Sep. 2013.
Dubin, Weekly, Oral Zoledronic Acid can Improve Quality of Life for Bone Metastases Sufferers, Specialty Pharma, 10(3), 30-33, Nov. 2010.
Eekhoff et al., Determinants of Induction and Duration of Remission of Paget's Disease of Bone after Bisphosphonate (Olpadronate) Therapy, abstract, Bone, 33(5), 831-838, Nov. 2003.
Epstein et al., Update of Monthly Oral Bisphosphonate Therapy for the Treatment of Osteoporosis: Focus on Ibandronate 150 mg and Risedronate 150 mg, Current Medical Research and Opinion, 25(12), 2951-2960, Oct. 2009.
European Medicines Agency, Opinion of the Committee for Orphan Medicinal Products on Orphan Medicinal Product Designation, 3 pgs., Sep. 2013.
European Medicines Agency, Public Summary of Opinion on Orphan Designation, Zoledronic Acid for the Treatment of Complex Regional Pain Syndrome, 4 pgs., Oct. 2013.
European Medicines Agency, Scientific Discussion of ACLASTA®, 24 pgs., Mar. 2005, available at: http://www.ema.europa.eu/docs/en_GB/document_library/EPAR_-_Scientific_Discussion/human/000595/WC500020933.pdf.
European Union Summary of Product Characteristics for ACLASTA®, last accessed Aug. 2012, 19 pgs.
European Union Summary of Product Characteristics for ZOMETA®, last accessed Aug. 2012, 49 pgs.
Forouzanfar et al., Treatment of Complex Regional Pain Syndrome Type I., European Journal of Pain, 6(2), 105-122, Apr. 2002.
Fujita et al., Analgesic and Chondroprotective Effects of Risedronate in Osteoarthritis assessed by Electroalgometry and Measurement of Collagen Type II Fragments in Urine, Journal of International Medical Research, 36(5), 93241, Oct. 2008.
Fujita et al., Comparison of Maximum Drug Concentration and Area Under the Time-Concentration Curve Between Humans and Animals for Oral and Intravenous Investigational Drugs, The Journal of Clinical Pharmacology, 46(6), 374-692, Jun. 2006.
Gangji et al., Analgesic Effect of Intravenous Pamidronate on Chronic Back Pain Due to Osteoporotic Vertebral Fractures, Clinical Rheumatology, 18(3), 266-267, May 1999.
Giles, Risedronate not an Effective Disease Modifier in Knee Osteoarthritis, John Hopkins Medicine, Oct. 2006, available at http://www.hopkinsarthritis.org/arthritis-news/risedronate-not-an-effective-disease-modifier-in-knee-Osteoarthritis.
Goa et al., Risedronate, abstract, Drugs & Aging, 13(1), 83-91, Jul. 1998.
Green et al., Pharmacologic Profile of Zoledronic Acid: A Highly Potent Inhibitor of Bone Resorption, Drug Development Research, 55(4), 210-224, Apr. 2002.
Gremeaux et al., Complex Regional Pain Syndrome of the Knee: Early and Good Action of Biphosphonates on Pain and Function, Annales de réadaptation et de médecine physique 50(4), 240-243, May 2007.
Guo et al., Substance P Signaling Contributes to the Vascular and Nociceptive Abnormalities Observed in a Tibial Fracture Rat Model of Complex Regional Pain Syndrome Type I, Pain, 108(1), 95-107, Mar. 2004.
Hadjipavlou et al., Paget's Disease of the Spine and its Management, European Spine Journal, 10(5), 370-384, Oct. 2001.
Hamida et al., Myositis Ossificans Circumscripta of the Knee Improved by Alendronate, Joint Bone Spine, 71(2), 144-146, Apr. 2004.
Henson et al., Complex Regional Pain Syndrome: State-of-the-Art Update, Current Treatment Options in Cardiovascular Medicine, 12(2), 156-167, Apr. 2010.
Huygen et al., Evidence for Local Inflammation in Complex Regional Pain Syndrome Type 1, Mediators of Inflammation, 11(1), 47-51, Feb. 2002.
Kim et al., Analgesic Effects of the Non-Nitrogen-Containing Bisphosphonates Etidronate and Clodronate, Independent of Anti-Resorptive Effects on Bone, European Journal of Pharmacology, 699(1-3), 14-22, Jan. 2013.
Kingery et al., A Substance P Receptor (NK1) Antagonist can Reverse Vascular and Nociceptive Abnormalities in a Rat Model of Complex Regional Pain Syndrome Type II, Pain, 104(1-2), 75-84, Jul. 2003.
Koivisto et al., Efficacy of Zoledronic Acid for Chronic Low Back Pain Associated with Modic Changes in Magnetic Resonance Imaging, BMC Musculoskeletal Disorders, 15(64), 1-9, Mar. 2014.
Kopterides et al., Successful Treatment of SAPHO Syndrome with Zoledronic Acid, Rheumatoid Arthritis, 50(9), 2970-2973, Sep. 2004.
Kretzchmar et al., Rapid and Sustained Influence of Intravenous Zoledronic Acid on Course of Pain and Analgesics Consumption in Patients with Cancer with Bone Metastases: A Multicenter Open-Label Study over 1 Year, Supportive Cancer Therapy, 4(4), 203-210, Sep. 2007.
Kubalek et al., Treatment of Reflex Sympathetic Dystrophy with Pamidronate: 29 Cases, Rheumatology, 40(12),1394-1397, Dec. 2001.
Bennett et al., A Peripheral Mononeuropathy in Rat That Produces Disorders of Pain Sensation Like Those Seen in Man, Pain, 33(1), 87-107, Apr. 1988.
Daemen et al., Neurogenic Inflammation and Reflex Sympathetic Dystrophy (in Vivo and in Vitro Assessment in an Experimental Model), Acta Orthopaedica Belgica, 64(4), 441-447,1998.

(56) References Cited

OTHER PUBLICATIONS

Kurvers et al., Influence of Partial Nerve Injury in the Rat on Efferent Function of Sympathetic and Antidromically Acting Sensory Nerve Fibers, Journal of Trauma and Acute Care Surgery, 41(6), 981-988, Dec. 1996.
Seltzer et al., A Novel Behavioral Model of Neuropathic Pain Disorders Produced in Rats by Partial Sciatic Nerve Injury, Pain 43(2), 205-218, Nov. 1990.
Messeri et al., Analgesic Efficacy and Tolerability of Ketoprofen Lysine Salt vs Paracetamol in Common Paediatric Surgery. A Randomized, Single-Blind, Parallel, Multicentre Trial, Paediatric Anaesthesia,13(7), 574-578, Sep. 2003.
Cimini et al., Gastroprotective Effects of L-Lysine Salification of Ketoprofen in Ethanol-Injured Gastric Mucosa, Journal of Cellular Physiology, 230, 813-820, Oct. 2014.
Bernardi et al., Protective Effect of Some Basic Amino Acids Against the Damage to the Gastric Mucosa Produced by Indomethacin in Pylorus-Ligated Rats, Rivista di Farmacologia e Terapia, 6(3), 245-248, 1975.
Ruperto, A Randomized, Double-Blind, Placebo-Controlled Trial of Paracetamol and Ketoprofren Lysine Salt for Pain Control in Children with Pharyngotonsillitis Cared by Family Pediatricians, Italian Journal of Pediatrics, 37:48, 2011.
Novartis, Novartis Reports Record Results for 2009 as Sales Increase 7%, IHS Markit, Same-Day Analysis, 7 pages, Jan. 26, 2010, available at: https://www.ihs.com/country-industry-forcasting.html?ID=106594641.
U.S. Appl. No. 15/385,415, filed Dec. 20, 2016 First Named Inventor: Herriot Tabuteau Assignee: Antecip Bioventures II LLC.
U.S. Appl. No. 15/386,858, filed Dec. 21, 2016 First Named Inventor: Herriot Tabuteau Assignee: Antecip Bioventures II LLC.
Grünenthal GmbH, Petition for Post Grant Review of U.S. Pat. No. 9,283,239, Dec. 14, 2016.
Grunenthal GmbH, Declaration of Stephen Bruehl, for Petition for Post Grant Review of U.S. Pat. No. 3,283,239, Dec. 15, 2016.
U.S. Appl. No. 15/403,073, filed Jan. 10, 2017 First Named Inventor: Herriot Tabuteau Assignee: Antecip Bioventures II LLC.
U.S. Appl. No. 15/408,783, filed Jan. 18, 2017 First Named Inventor: Herriot Tabuteau Assignee: Antecip Bioventures II LLC.
U.S. Appl. No. 15/414,402, filed Jan. 24, 2017 First Named Inventor: Herriot Tabuteau Assignee: Antecip Bioventures II LLC.
U.S. Appl. No. 15/416,995, filed Jan. 26, 2017 First Named Inventor: Herriot Tabuteau Assignee: Antecip Bioventures II LLC.
U.S. Appl. No. 15/426,908, filed Feb. 7, 2017 First Named Inventor: Herriot Tabuteau Assignee: Antecip Bioventures II LLC.
Carbonare et al., Safety and Tolerability of Zoledronic Acid and Other Bisphosphonates in Osteoporosis Management, Drug, Healthcare & Patient Safety, 2, 121-137, Jan. 2010.
Pazianas et al., Eliminating the Need for Fasting with Oral Administration of Bisphosphonates, Therapeutics & Clinical Risk Management, 9, 395-402, 2013.
WHO Expert Committee on Specifications for Pharmaceutical Preparations, Good Manufacturing Practices for Pharmaceutical Products: Main Principles, Annex 2, Forty-Eighth Report, WHO Technical Report series, 986, 77-135, 2014.
Aungst, Absorption Enhancers: Applications and Advances, The AAPS Journal, 14(1), 10-18, Mar. 2012.
Auxilium Pharmaceuticals Corporation, Testim® Drug Label, Aug. 2013.
Losina et al., Lifetime Risk and Age at Diagnosis of Symptomatic Knee Osteoarthritis in the US, Arthritis Care & Research, 65(5), 703-711, May 2013.
Harden et al., The Osteoarthritis Knee Model: Psychophysical Characteristics and Putative Outcomes, The Journal of Pain, 14(3): 281-289, Mar. 2013.
Spector, Bisphosphonates: Potential Therapeutic Agents for Disease Modification in Osteoarthritis, Aging Clinical & Experimental Research, 15(5), 413-418, Oct. 2003.

Spector et al., Effect of Risedronate on Joint Structure and Symptoms of Knee Osteoarthritis: Results of the BRISK Randomized, Controlled Trial [ISRCTN01928173], Arthritis Reserch & Therapy, 7(3), R625, Mar. 2005.
Carbone et al., The Relationship of Antiresorptive Drug Use to Structural Findings and Symptoms of Knee Osteoarthritis, Arthritis & Rheumatism, 50(11), 3516-3525, Nov. 2004.
Fujita et al., Comparison of the Analgesic Effects of Bisphosphonates: Etidronate, Alendronate and Risedronate by Electroalgometry Utilizing the Fall of Skin Impedance, Journal of Bone & Mineral Metabolism, 27(2), 234-239, Mar. 2009.
Piscitelli et al., Painful Prosthesis: Approaching the Patient with Persistent Pain Following Total Hip and Knee Arthroplasty, Clinical Cases in Mineral & Bone Metabolism, 10(2), 97-110, May 2013.
Riedel, Nociception, Pain, and Antinociception: Current Concepts, Zeitschrift für Rheumatologie, 60(6), 404-415, Dec. 2001.
.Hen et al., Osteoarthritis: Toward a Comprehensive Understanding of Pathological Mechanism, Bone Research, 5, 16044, Jan. 2017.
Harden et al., Prospective Examination of Pain-Related and Psychological Predictors of CRPS-Like Phenomena Following Total Knee Arthroplasty: A Preliminary Study, Pain, 106(3), 393-400, Dec. 2003.
Harden et al., Development of a Severity Score for CRPS, Pain, 151(3), 870-876, Dec. 2010.
Bruehl et al., Associations Between KCNJ6 (GIRK2) Gene Polymorphisms and Pain-Related Phenotypes, Pain, 154(12), 2853-2859, Dec. 2013.
Rowe et al., Handbook of Pharmaceutical Excipients, 6th edition, Pharmaceutical Press, London, England, 285, 2009.
Banker & Rhodes, Modern Pharmaceutics, second edition, Drugs and Pharmaceutical Sciences, vol. 40, 91-142, 1990 (Chapter 3: Pharmacokinetics).
U.S. Appl. No. 15/599,319, filed May 18, 2017 First Named Inventor: Herriot Tabuteau Assignee: Antecip Bioventures II LLC.
U.S. Appl. No. 15/604,394, filed May 24, 2017 First Named Inventor: Herriot Tabuteau Assignee: Antecip Bioventures II LLC.
U.S. Appl. No. 15/605,730, filed May 25, 2017 First Named Inventor: Herriot Tabuteau Assignee: Antecip Bioventures II LLC.
U.S. Appl. No. 15/623,274, filed Jun. 14, 2017 First Named Inventor: Herriot Tabuteau Assignee: Antecip Bioventures II LLC.
U.S. Appl. No. 15/624,428, filed Jan. 10, 2017 First Named Inventor: Herriot Tabuteau Assignee: Antecip Bioventures II LLC.
U.S. Appl. No. 15/624,471, filed Jun. 15, 2017 First Named Inventor: Herriot Tabuteau Assignee: Antecip Bioventures II LLC.
Reid et al., Comparison of a Single Infusion of Zoledronic Acid with Risedronate for Paget's Disease, The New England Journal of Medicine, 353(9), 898-908, Sep. 2005.
Jarrett et al., Preliminary Evidence for a Structural Benefit of the New Bisphosphonate Zoledronic Acid in Early Rheumatoid Arthritis, Arthritis and Rheumatism, 54(5), 1410-1414, May 2006.
Polascik et al., Zoledronic Acid in the Management of Metastatic Bone Disease, Therapeutics and Clinical Risk Management, 4(1), 261-268, Feb. 2008.
Amanat et al., Optimal Timing of a Single Dose of Zoledronic Acid to Increase Strength in Rat Fracture Repair, Journal of Bone and Mineral Research, 22(6), 867-876, Jun. 2007.
U.S. Appl. No. 15/432,777, filed Feb. 14, 2016 First Named Inventor: Herriot Tabuteau Assignee: Antecip Bioventures II LLC.
U.S. Appl. No. 15/438,513, filed Feb. 21, 2017 First Named Inventor: Herriot Tabuteau Assignee: Antecip Bioventures II LLC.
U.S. Appl. No. 15/439,774, filed Feb. 22, 2017 First Named Inventor: Herriot Tabuteau Assignee: Antecip Bioventures II LLC.
U.S. Appl. No. 15/446,971, filed Mar. 1, 2017 First Named Inventor: Herriot Tabuteau Assignee: Antecip Bioventures II LLC.
Varenna et al., Predictors of Responsiveness to Bisphosphonate Treatment in Patients with Complex Regional Pain Syndrome Type I: A Retrospective Chart Analysis, Pain Medicine, pnw207, Sep. 2016.
U.S. Appl. No. 15/454,874, filed Mar. 9, 2017 First Named Inventor: Herriot Tabuteau Assignee: Antecip Bioventures II LLC.
U.S. Appl. No. 15/459,992, filed Mar. 15, 2017 First Named Inventor: Herriot Tabuteau Assignee: Antecip Bioventures II LLC.

(56) References Cited

OTHER PUBLICATIONS

Rodriguez et al., Long-Term Results of Total Knee Arthroplasty in Class 3 and 4 Rheumatoid Arthritis. The Journal of Arthroplasty, 11(2), 141-145, Feb. 1996.
Pain Assessment Scale, Galer, Hensen & Gammaitoni, 2003.
U.S. Appl. No. 15/481,330, filed Apr. 6, 2017 First Named Inventor: Herriot Tabuteau Assignee: Antecip Bioventures II LLC.
U.S. Appl. No. 15/484,766, filed Apr. 11, 2017 First Named Inventor: Herriot Tabuteau Assignee: Antecip Bioventures II LLC.
Gad et al., Preclinical Development Handbook: ADME and Biopharmaceutical Properties. A John Wiley and Sons. Inc, Hoboken, New Jersey. p. 301, 2008.
Lindmark et al., Mechanisms of absorption enhancement by medium chain fatty acids in intestinal epithelial Caco-2 cell monolayers. Journal of Pharmacology and Experimental Therapeutics, 275(2), 958-64, Nov. 1995.
Falk et al., Pain and Nociception: Mechanisms of Cancer-Induced Bone Pain, Journal of Clinical Oncology, 32(16),1647-54, May 2014.
Wasner et al., R. Complex Regional Pain Syndrome-Diagnostic, Mechanisms, CNS Involvement and Therapy, Spinal Cord, 41(2), 61-75, Feb. 2003.
Wu et al., Patterns of Pain and Interference in Patients with Painful Bone Metastases: A Brief Pain Inventory Validation Study, Journal of Pain and Symptom Management, 39(2), 230-40, Feb. 2010.
Anson, Pain News Network, Apr. 8, 2016.
Moseley et al., Intense Pain Soon After Wrist Fracture Strongly Predicts Who Will Develop Complex Regional Pain Syndrome: Prospective Cohort Study. The Journal of Pain,15(1),16-23, Jan. 2014.
Otrock et al. Intravenous Zoledronic Acid Treatment in Thalassemia-Induced Osteoporosis: Results of a Phase II clinical Trial, Annals of Hematology, 85(9), 605-9, Sep. 2006.
U.S. Appl. No. 15/498,251, filed Feb. 21, 2017 First Named Inventor: Herriot Tabuteau Assignee: Antecip Bioventures II LLC.
U.S. Appl. No. 15/587,108, filed Feb. 21, 2017 First Named Inventor: Herriot Tabuteau Assignee: Antecip Bioventures II LLC.
U.S. Appl. No. 15/587,246, filed Feb. 21, 2017 First Named Inventor: Herriot Tabuteau Assignee: Antecip Bioventures II LLC.
Grünenthal GmbH, Petition for Post Grant Review of U.S. Pat. No. 9,408,862, May 8, 2017.
Grünenthal GmbH, Declaration of Stephen Bruehl, for Petition for Post Grant Review of U.S. Pat. No. 3,408,862, May 8, 2017.
Grünenthal Gmbh, Declaration of Clive G. Wilson, for Petition for Post Grant Review of U.S. Pat. No. 3,408,862, May 8, 2017.
Wardley et al., Zoledronic Acid Significantly Improves Pain Scores and Quality of Life in Breast Cancer Patients with Bone Metastases: A Randomised, Crossover Study of Community vs Hospital Bisphosphonate Administration, British Journal Cancer, 92(10), 1869-1876, May 2005.
Merskey & Bogduk, eds., Classification of Chronic Pain: Descriptions of Chronic Pain Syndromes and Definitions of Pain Terms, 2nd ed., Seattle: IASP, 40-34, 1994.
Woolf, What Is This Thing Called Pain? The Journal of clinical investigation, 120(11), 3742-3744, Nov. 2010.
Ruza et al., Clinical Experience with Intravenous Zoledronic Acid in the Treatment of Male Osteoporosis: Evidence and Opinions,Therapeutic Advances Musculoskeletal Disease 5(4), 182-198, Aug. 2013.
U.S. Appl. No. 15/702,616, filed Sep. 12, 2017, First Named Inventor: Herriot Tabuteau, Assignee: Antecip Bioventures II LLC.
U.S. Appl. No. 15/703,891, filed Sep. 13, 2017, First Named Inventor: Herriot Tabuteau, Assignee: Antecip Bioventures II LLC.
U.S. Appl. No. 15/707,238, filed Sep. 18, 2017, First Named Inventor: Herriot Tabuteau, Assignee: Antecip Bioventures II LLC.
U.S. Appl. No. 15/707,673, filed Sep. 18, 2017, First Named Inventor: Herriot Tabuteau, Assignee: Antecip Bioventures II LLC.
U.S. Appl. No. 15/710,759, filed Sep. 20, 2017, First Named Inventor: Herriot Tabuteau, Assignee: Antecip Bioventures II LLC.
U.S. Appl. No. 15/716,334, filed Sep. 26, 2017, First Named InventorL Herriot Tabuteau, Assignee: Antecip Bioventures II LLC.
Grünenthal Gmbh, Petition for Post Grant Review of U.S. Pat. No. 9,539,268, Oct. 10, 2017.
U.S. Appl. No. 15/782,480, filed Oct. 12, 2017, First Named Inventor: Herriot Tabuteau, Assignee: Antecip Bioventures II LLC.
U.S. Appl. No. 15/787,612, filed Oct. 18, 2017, First Named Inventor: Herriot Tabuteau, Assignee: Antecip Bioventures II LLC.
Grünenthal Gmbh, Declaration of Stephen Bruehl, for Petition for Post Grant Review of U.S. Pat. No. 9,539,268, Oct. 10, 2017.
Grünenthal Gmbh, Declaration of Clive G. Wilson, for Petition for Post Grant Review of U.S. Pat. No. 9,539,268, Oct. 10, 2017.
Catrina et al., Mechanisms Leading from Systemic Auto Immunity to Joint-specific Disease in Rheumatoid Arthritis, Natural Review, Rheumatology, 13(2), 79-86, Dec. 2016.
Neogi et al., The Effect of Alendronate on Progression of Spinal Osteophytes and Disc-space Narrowing, Annals Rheumatic Diseases, 67, 1427-30, Feb. 2008.
Almarestani et al., Imaging Studies in Freund's Complete Adjuvant Model of Regional Polyarthritis, a Model Suitable for the Study of Pain Mechanisms, in the Rat, Arthritis & Rheumatism, 63(6), 1573-81, Jun. 2011.
Chillingworth & Donaldson, Characterisation of a Freund's complete adjuvant-induced model of chronic arthritis in mice, J. Neurosci. Methods, 128(1-2), 45-52, Sep. 2003.
Rollins, Chapter 38: Preformulation, in Remington's Pharm. Sci., 700-20, 2000 (Limmer et al. eds., 20th ed. 2000).
Malinowski, Chapter 53: Bioavailability & Bioequivalence Testing, in Remington's Pharm. Sci., 995-1004, 2000 (Limmer et al. eds., 20th ed. 2000).
Rollins, Chapter 59: Clinical Pharmacokinetics, in Remington's Pharm. Sci., 1145-55, 2000 (Limmer et al. eds., 20th ed. 2000).
Yamada, et al., Gastric pH Profile and Its Control in Fasting Beagle Dogs, Chem. Pharm. Bull, 37(9), 2539-2541, Sep. 1989.
Lui, et al., Comparison of Gastrointestinal pH in Dogs and Humans: Implications on the Use of the Beagle Dog as a Model for Oral Absorption in Humans, J. Pharm. Sci., 75(3), 271-74, Mar. 1986.
Buckland-Wright et al., A 2 yr Longitudinal Radiographic Study Examining the Effect of a Bisphosphonate (Risedronate) upon Subchondral Bone Loss in Osteoarthritic Knee Patients, Rheumatology, 46, 257-64, Jul. 2007.
McQueen et al., Zoledronic Acid Does not Reduce MRI ErosiveProgression in PsA but may Suppress Bone Oedema: the Zoledronic Acid in Psoriatic Arthritis (ZAPA) Study, Annals Rheumatic Diseases, 70, 1091-94, Feb. 2011.
U.S. Appl. No. 15/647,140, filed Jul. 11, 2017, First Named Inventor: Herriot Tabuteau, Assignee: Antecip Bioventures II LLC.
Expert Declaration of Dr. Socrates Papapoulos, paragraphs 40-46, Apr. 2017.
*Grunenthal GMBH v. Antecip Bioventures II LLC*, Case PGR2017-00008, U.S. Pat. No. 9,238,239, Patent Owner's Preliminary Response, p. 35, Apr. 2017.
*Grunenthal GMBH v. Antecip Bioventures II LLC*, Case PGR2017-00008, U.S. Pat. No. 9,238,239, Decision, Institution of Post-Grant Review, pp. 29-30, Jul. 2017.
U.S. Appl. No. 15/672,126, filed Aug. 8, 2017, First Named Inventor: Herriot Tabuteau, Assignee: Antecip Bioventures II LLC.
U.S. Appl. No. 15/672,147, filed Aug. 8, 2017, First Named Inventor: Herriot Tabuteau, Assignee: Antecip Bioventures II LLC.
Guermazi et al., Different Thresholds for Detecting Osteophytes and Joint Space Narrowing Exist Between the Site Investigators and the Centralized Reader in A Multicenter Knee Osteoarthritis Study— Data from the Osteoarthritis Initiative, Skeletal Radiology, 41(2), 179-86, Feb. 2012.
Jimenez-Boj et al., Interaction Between Synovial Inflammatory Tissue and Bone Marrow in Rheumatoid Arthritis. The Journal of Immunology, 175(4), 2579-2588, Aug. 2005.
Wolfe et al., Assessment of Pain in Rheumatoid Arthritis: Minimal Clinically Significant Difference, Predictors, And the Effect of Anti-tumor Necrosis Factor Therapy. The Journal of Rheumatology, 34(8), 1674-1683, Aug. 2007.
U.S. Appl. No. 15/697,211, filed Sep. 6, 2017, First Named Inventor: Herriot Tabuteau, Assignee: Antecip Bioventures II LLC.

(56) References Cited

OTHER PUBLICATIONS

U.S. Appl. No. 15/697,267, filed Sep. 6, 2017, First Named Inventor: Herriot Tabuteau, Assignee: Antecip Bioventures II LLC.

* cited by examiner

COMPOSITIONS FOR ORAL ADMINISTRATION OF ZOLEDRONIC ACID OR RELATED COMPOUNDS FOR TREATING COMPLEX REGIONAL PAIN SYNDROME

CROSS-REFERENCE TO RELATED APPLICATIONS

This application is a continuation-in-part of U.S. patent application Ser. No. 15/164,651, filed May 25, 2016, which is a continuation of U.S. patent application Ser. No. 15/055,386, filed Feb. 26, 2016, which is a continuation of U.S. patent application Ser. No. 14/635,857, filed Mar. 2, 2015, now U.S. Pat. No. 9,283,239, which is a continuation of U.S. patent application Ser. No. 14/279,232, filed May 15, 2014, now U.S. Pat. No. 9,149,487, which is a continuation of U.S. patent application Ser. No. 14/063,979, filed Oct. 25, 2013, now U.S. Pat. No. 8,802,658, which is a continuation-in-part of U.S. patent application Ser. No. 13/894,274, filed May 14, 2013, now abandoned, which claims the benefit of U.S. Prov. App. Nos. 61/646,538, filed May 14, 2012; 61/647,478, filed May 15, 2012; 61/654,292, filed Jun. 1, 2012; 61/654,383, filed Jun. 1, 2012; 61/655,527, filed Jun. 5, 2012; 61/655,541, filed Jun. 5, 2012; 61/764,563, filed Feb. 14, 2013; 61/762,225, filed Feb. 7, 2013; 61/767,647, filed Feb. 21, 2013; 61/767,676, filed Feb. 21, 2013; and 61/803,721, filed Mar. 20, 2013; this application is also a continuation-in-part of U.S. patent application Ser. No. 15/347,696, filed Nov. 9, 2016, which is a continuation-in-part of International Pat. App. No. PCT/US2015/032739, filed May 27, 2015; any of the applications, U.S. patents issued from, or U.S. publications of any of the above applications are incorporated by references in their entirety.

SUMMARY

Bisphosphonate compounds are potent inhibitors of osteoclast activity, and are used clinically to treat bone-related conditions such as osteoporosis and Paget's disease of bone; and cancer-related conditions including multiple myeloma, and bone metastases from solid tumors. They generally have low oral bioavailability.

Patchy osteoporosis and bone marrow edema may result from osteoclast hyperactivity. Zoledronic acid is a potent inhibitor of bone resorption and osteoclast activity. Nitrogen containing bisphosphonates, such as zoledronic acid, also inhibit the mevalonate pathway in the osteoclast thereby interrupting normal osteoclast function.

It has been discovered that oral dosage forms of bisphosphonate compounds, such as zoledronic acid, can be used to treat or alleviate pain or related conditions.

Some embodiments include a method of enhancing the oral bioavailability of zoledronic acid comprising orally administering a dosage form containing zoledronic acid in the disodium salt form.

Some embodiments include a dosage form comprising zoledronic acid in the disodium salt form, wherein the bioavailability, in a mammal, of zoledronic acid in the disodium salt form is greater than the bioavailability of zoledronic acid in the diacid form would be in the same dosage form.

Some embodiments include a dosage form comprising zoledronic acid in an acid or a salt form, such as the disodium salt form, wherein the dosage form contains an amount of zoledronic acid in the disodium salt form that provides an area under the plasma concentration curve of zoledronic acid of about 4 ng·h/mL to about 2000 ng·h/mL to a human being to which the dosage form is administered.

Some embodiments include a dosage form comprising zoledronic acid in the disodium salt form, wherein the disodium salt form is present in a lower molar amount than would be present if the zoledronic acid were in the diacid form; and wherein the zoledronic acid in the disodium salt form has an improved bioavailability as compared to the zoledronic acid in the diacid form to the extent that the lower molar amount of the disodium salt in the dosage form does not reduce the amount of zoledronic acid delivered to the plasma of a mammal.

Although an oral dosage form with enhanced bioavailability with respect to the bisphosphonate compound can be used, the treatment can also be effective using an oral dosage form that includes a bisphosphonate compound, such as zoledronic acid, wherein the bioavailability of the bisphosphonate is unenhanced, or is substantially unenhanced.

Some embodiments include a method of relieving inflammatory pain comprising administering an oral dosage form containing zoledronic acid to a mammal in need thereof, wherein the mammal experiences significant pain relief more than 3 hours after administration of the dosage form.

Some embodiments include a method of relieving pain associated with an arthritis comprising administering an oral dosage form containing zoledronic acid to a human being in need thereof.

Some embodiments include a method of treating complex regional pain syndrome comprising administering an oral dosage form containing zoledronic acid to a mammal in need thereof.

Some embodiments include an oral dosage form comprising zoledronic acid, wherein the oral bioavailability of zoledronic acid is substantially unenhanced. For example, in some embodiments, the oral bioavailability in the dosage form is about 0.01% to about 4%.

Some embodiments include a pharmaceutical product comprising more than one unit of an oral dosage form described herein. In some embodiments, each unit of the oral dosage form contains about 1 mg to about 50 mg of zoledronic acid.

Some embodiments include a method of relieving inflammatory pain comprising administering an oral dosage form containing zoledronic acid to a mammal in need thereof.

In some embodiments, the mammal receives a total monthly dose of zoledronic acid that is about 800 mg/m$^2$ or less.

In some embodiments, the dosage form contains about 10 mg/m$^2$ to about 20 mg/m$^2$ based upon the body surface area of the mammal.

Some embodiments include a method of relieving inflammatory pain comprising orally administering zoledronic acid to a mammal in need thereof.

In some embodiments, about 300 mg/m$^2$ to about 600 mg/m$^2$ of zoledronic acid is administered per month, based upon the body surface area of the mammal.

In some embodiments, about 50 mg/m² to about 600 mg/m² of zoledronic acid is administered per month, based upon the body surface area of the mammal.

Some embodiments include administering an osteoclast inhibitor, such as a bisphosphonate, including zoledronic acid, neridronic acid, etc. to inhibit the development of pain, unweighting, and edema when administered early such as when a precipitating event such as fracture occurs, wherein the precipitating event is associated with CRPS.

Some embodiments include administering an osteoclast inhibitor, such as a bisphosphonate, including zoledronic acid, neridronic acid, etc. to reverse established allodynia and unweighting when administered at least 4 weeks after a precipitating event such as fracture that is associated with CRPS.

DETAILED DESCRIPTION

Figure 1:
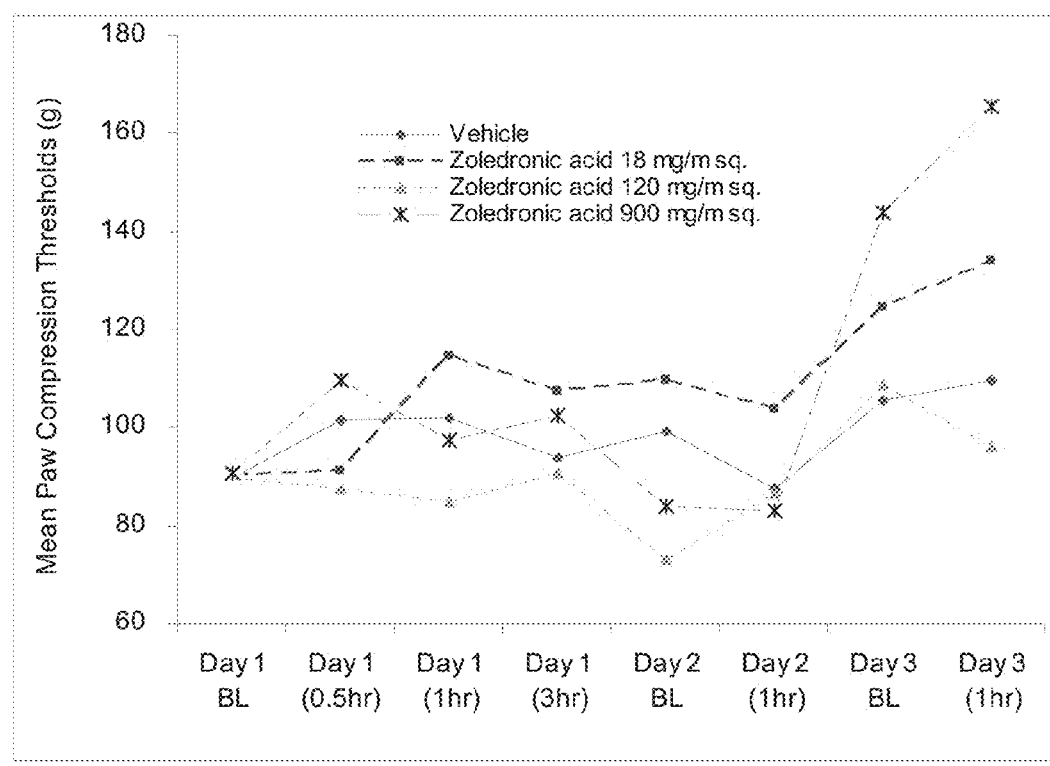
FIG. 1 is a plot of pain compression thresholds in a rat model of inflammatory pain using three different doses of zoledronic acid. Measurements were taken at baseline (BL) and at various time points after dosing on the days indicated.

Inhibitors of osteoclast activity include bisphosphonate compounds such as pamidronate or pamidronic acid, neridronate or neridronic acid, olpadronate or olpadronic acid, alendronate or alendronic acid, incadronate or incadronic acid, ibandronate or ibandronic acid, risedronate or risedronic acid, cimadronate or cimadronic acid, zoledronate or zoledronic acid, etidronate or etidronic acid, clodronate or clodronic acid, tiludronate or tiludronic acid, etc.

RANK/RANKL antagonists may be inhibitors of osteoclast activity. RANK/RANKL antagonists include but are not limited to OPG (osteoprotegerin) or a variant thereof, an anti-RANKL antibody such as denosumab, a monoclonal anti-RANKL antibody, a small interfering RNA, a microRNA, a precursor molecule, a ribozyme, an antisense nucleic acid, or an aptamer targeting RANKL. Antibodies such as AB-25E9, small molecules, small interfering RNAs, microRNAs, precursor molecules, ribozymes, antisense nucleic acids, or aptamers that target the cell-surface protein Siglec-15 may be osteoclast inhibitors.

Some Bruton's tyrosine kinase (BTK) inhibitors may be inhibitors of osteoclast activity. BTK inhibitors can include ONO-4059; ibrutinib; Benzo[b]thiophene-2-carboxamide, N-[3-[6-[[4-[(2R)-1,4-dimethyl-3-oxo-2-piperazinyl]phenyl]amino]-4,5-dihydro-4-methyl-5-oxo-2-pyrazinyl]-2-methylphenyl]-4,5,6,7-tetrahydro- (GDC-0834); RN-486; Benzamide, 4-(1,1-dimethylethyl)-N-[3-[8-(phenylamino)imidazo[1,2-a]pyrazin-6-yl]phenyl]-(CGI-560); Benzamide, N-[3-[4,5-dihydro-4-methyl-6-[[4-(4-morpholinylcarbonyl)phenyl]amino]-5-oxo-2-pyrazinyl]-2-methylphenyl]-4-(1,1-dimethylethyl)- (CGI-1746CAS Registry No. 910232-84-7); HM-71224; 2-Propenamide, N-[3-[[5-fluoro-2-[[4-(2-methoxyethoxy) phenyl]amino]-4-pyrimidinyl]amino]phenyl]- (CC-292, CAS Registry No. 1202757-89-8); 2-Pyridinecarboxamide, 4-[4-[[5-fluoro-4-[[3-[(1-oxo-2-propen-1-yl)amino]phenyl]amino]-2-pyrimidinyl]amino]phenoxy]-N-methyl- (CNX-774, CAS Registry No. 1202759-32-7), AVL-101 (CAS Registry No. 1552307-34-2), AVL-291 (CAS Registry No. 1552307-35-3), and AVL-292 (CAS Registry No. 1552307-36-4), [N-(2-chloro-6-methylphenyl)-2-(6-(4-(2-hydroxyethyl) piperazin-1-yl)-2-methylpyrimidin-4-ylamino)thiazole-5-carboxamide] (dasatinib), alpha-cyano-beta-hydroxy-beta-methyl-N-(2,5-bromophenyl) propenamide (LFM-A13), and ONO-WG-307.

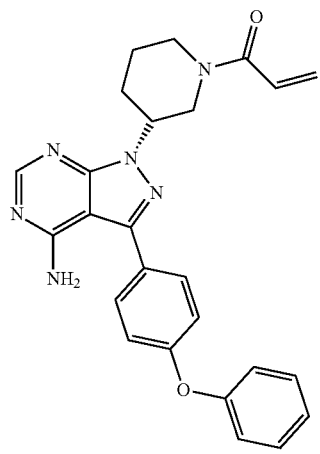
Ibrutinib
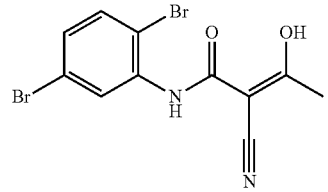
LFM-A13
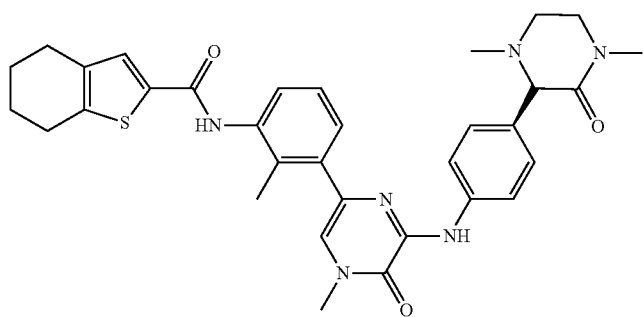
GDC-0834
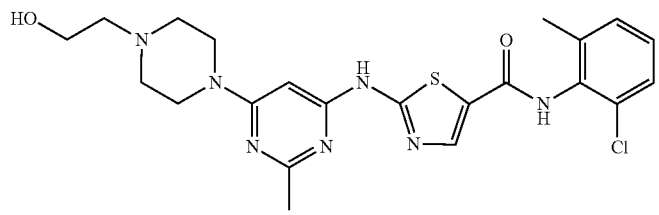
Dasatinib
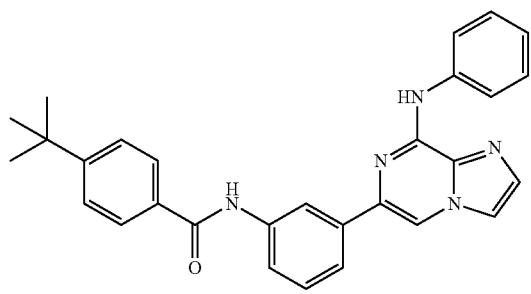
CGI-560
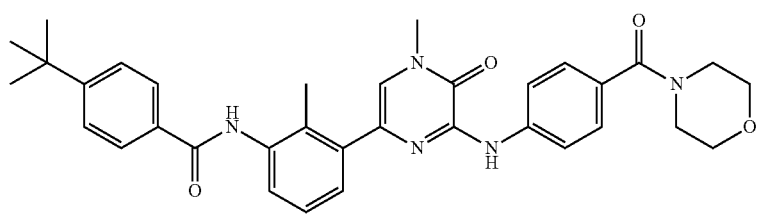
CGI-1746

-continued

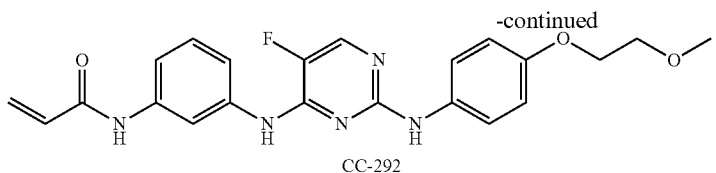
CC-292

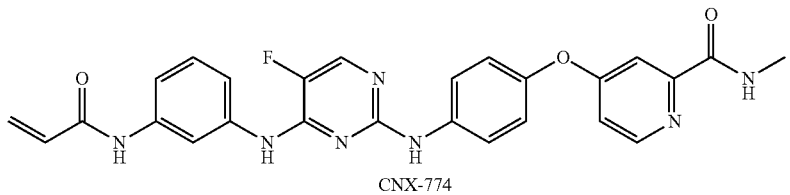
CNX-774

Inhibitors of osteoclast activity may be used for a number of medical purposes, such as treatment of undesirable conditions or diseases, including pain relief. This may be accomplished in many instances by administration of oral dosage forms. Generally, an oral dosage form comprising a bisphosphonate such as zoledronic acid is administered orally to a mammal, such as a human being, at least once, to treat a disease or condition, or to relieve pain.

The compounds containing Ion 1 or Ion 2 may also be osteoclast inhibitors:

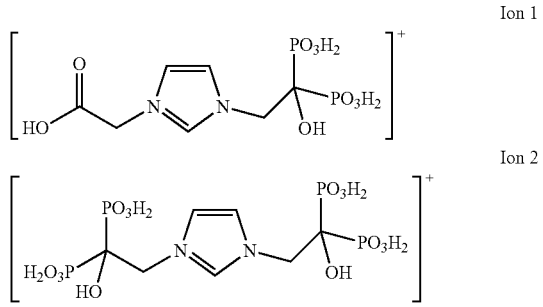

The term "treating" or "treatment" broadly includes any kind of treatment activity, including the diagnosis, cure, mitigation, or prevention of disease in man or other animals, or any activity that otherwise affects the structure or any function of the body of man or other animals.

An oral dosage form of a bisphosphonate such as zoledronic acid may be used to treat, or provide relief of, any type of pain including, but not limited to, inflammatory pain, arthritis pain, complex regional pain syndrome, lumbosacral pain, musculoskeletal pain, neuropathic pain, chronic pain, cancer-related pain, acute pain, postoperative pain, etc. In some instances, pain relief may be palliative, or pain relief may be provided independent of improvement of the disease or condition or the underlying cause of the disease or condition. For example, although the underlying disease may not improve, or may continue to progress, an individual suffering from the disease may experience pain relief. In some embodiments, enhanced bioavailability of the zoledronic acid may be achieved in treating one of these conditions by administering a dosage form comprising zoledronic acid in the form of a disodium salt. This may allow a reduced molar amount of the disodium salt to be used as compared to what would be used with the diacid form.

In some embodiments, the mammal being treated is not suffering from bone metastasis. In some embodiments, the mammal being treated is not suffering from cancer. In some embodiments, the mammal being treated is not suffering from osteoporosis.

For example, zoledronic acid or another bisphosphonate may be administered orally to relieve musculoskeletal pain including low back pain, and pain associated with rheumatoid arthritis, juvenile rheumatoid arthritis, osteoarthritis, erosive osteoarthritis, sero-negative (non-rheumatoid) arthropathies, non-articular rheumatism, peri-articular disorders, axial spondyloarthritis including ankylosing spondylitis, Paget's disease, fibrous dysplasia, SAPHO syndrome, transient osteoarthritis of the hip, vertebral crush fractures, osteoporosis, etc. In some embodiments, enhanced bioavailability of the zoledronic acid may be achieved in treating one of these conditions by administering a dosage form comprising zoledronic acid in the form of a disodium salt. This may allow a reduced molar amount of the disodium salt to be used as compared to what would be used with the diacid form.

An osteoclast inhibitor, such as a bisphosphonate, e.g. zoledronic acid, may also be used to treat bone fractures or to enhance the healing of bone fractures. In some embodiments, a human being that is treated for CRPS, suffered from a precipitating injury such as a bone fracture associated with the CRPS at least 4 weeks, at least 8 weeks, at least 12 weeks, at least six months, or at least 1 year before first administering an osteclast inhibitor, such as a bisphosphonate, including zoledronic acid, neridronic acid, etc. Examples of a precipitating event include a fracture, a cutting injury, a scratch, a puncture injury, etc.

In some embodiments, zoledronic acid or another bisphosphonate may also be administered orally to relieve neuropathic pain, including diabetic peripheral neuropathy, post-herpetic neuralgia, trigeminal neuralgia, monoradiculopathies, phantom limb pain, and central pain. Other causes of neuropathic pain include cancer-related pain, lumbar nerve root compression, spinal cord injury, post-stroke pain, central multiple sclerosis pain, HIV-associated neuropathy, and radio-therapy or chemo-therapy associated neuropathy. In some embodiments, enhanced bioavailability of the zoledronic acid may be achieved in treating one of these conditions by administering a dosage form comprising zoledronic acid in the form of a disodium salt. This may allow a reduced molar amount of the disodium salt to be used as compared to what would be used with the diacid form.

In some embodiments, zoledronic acid or another bisphosphonate may be administered orally to relieve inflammatory pain including musculoskeletal pain, arthritis pain, and complex regional pain syndrome. In some embodiments, enhanced bioavailability of the zoledronic acid may be achieved in treating one of these conditions by administering a dosage form comprising zoledronic acid in the form of a disodium salt. This may allow a reduced molar amount of the disodium salt to be used as compared to what would be used with the diacid form.

Examples of musculoskeletal pain include low back pain; and pain associated with vertebral crush fractures, fibrous dysplasia, osteogenesis imperfecta, Paget's disease of bone, transient osteoporosis, and transient osteoporosis of the hip.

Arthritis refers to inflammatory joint diseases that can be associated with pain. Examples of arthritis pain include pain associated with osteoarthritis, erosive osteoarthritis, rheumatoid arthritis, juvenile rheumatoid arthritis, sero-negative (non-rheumatoid) arthropathies, non-articular rheumatism, peri-articular disorders, neuropathic arthropathies including Charcot's foot, axial spondyloarthritis including ankylosing spondylitis, and SAPHO syndrome.

In some embodiments, a human being that is treated for a disease or condition, such as an inflammatory condition, e.g. arthritis or CRPS, by an osteoclast inhibitor, such as a bisphosphonate, e.g. an oral dosage form of zoledronic acid, has an age of at least 18 years, at least 50 years (including a male of at least 50 years), a postmenopausal female, about 10 years to about 90 years, about 20 years to about 80 years, about 30 years to about 75 years, about 40 years to about 70 years, about 1 year to about 16 years, or about 80 years to about 95 years. In some embodiments, the human being is a male at least 50 years of age or a postmenopausal female, with knee osteoarthritis (OA) and bone marrow lessions (BMLs), having moderate or worse knee pain.

In some embodiments, a human being that is treated for a disease or condition, such as an inflammatory condition, e.g. arthritis, low back pain, or CRPS, by an osteoclast inhibitor, such as a bisphosphonate, e.g. an oral dosage form of zoledronic acid, has suffered from the inflammatory condition for at least 1 month, at least 2 months, at least 3 months, at least 6 months, or at least 1 year.

In some embodiments, the arthritis affects a knee, an elbow, a finger, a wrist, a shoulder, an ankle, the spine, or a hip.

For treatment of arthritis or joint pain, such as knee pain, in some embodiments the person being treated has OARSI Grade 0, or Kellgren and Lawrence Grades 0 or 1, joint space narrowing.

In some embodiments, the person has lesions, such as bone marrow lesions. In some embodiments the person being treated for bone marrow lesions has normal joint space knee pain, OARSI Grade 0, or Kellgren and Lawrence Grades 0 or 1, joint space narrowing.

In some embodiments, the person has baseline pain intensity of 5 or greater measured using the 0-10 numerical rating scale (NRS), or 50 mm or greater using the 100 mm visual analog scale (VAS). In some embodiments the person being treated for pain has normal joint space knee pain, OARSI Grade 0, or Kellgren and Lawrence Grades 0 or 1, joint space narrowing.

Bone marrow lesions (BMLs) include regional bone marrow signal intensity alterations on magnetic resonance imaging (MRI). BMLs can be present in the knee and can be an important feature of osteoarthritis of the knee. BMLs have also been described in other rheumatic conditions such as rheumatoid arthritis, osteonecrosis, ankylosing spondylitis, and transient osteoporosis of the hip and are often referred to as bone marrow edema (BME).

In some embodiments, a person being treated for arthritis, such as with zoledronic acid, has osteoarthritis of the knee associated with bone marrow lesions.

In some embodiments, an inhibitor of osteoclast activity can be used to treat bone marrow lesions.

In some embodiments, an inhibitor of osteoclast activity can be used to treat bone marrow lesions of the knee, shoulder, ankle, wrist, hand, fingers, spine, or hip.

Commonly used measures of pain intensity include the visual analog scale (VAS) and the numerical rating scale (NRS). With the VAS approach, patients rate the severity of their pain by marking a point on a 10-cm (or 100 mm) VAS (0=no pain and 10=worst possible pain). With the NRS approach, patients rate the severity of their pain by verbally responding to a 10-point NRS (0=no pain and 10=worst possible pain). VAS and NRS scores have been shown to be strongly correlated (slope of regression line, 1.01), indicating that a score on the 10-cm VAS is equivalent to the same score on 10-point NRS (Bijur P E et al. *Acad Emerg Med* 2003; 10:390-392). For example, a VAS score of 5 cm (or 50 mm) is equivalent to an NRS score of 5. Knee pain in a person with a VAS score of 5 cm or 50 mm or higher, or an NRS score of 5 or higher, may be referred to herein as moderate to severe knee pain.

In some embodiments, the patient suffering from pain, inflammation, a similar condition, or any of the conditions described herein, has an NRS of 5 or greater, or a VAS of 5 cm or greater. In some embodiments, the patient has an NRS of 4 or greater, or a VAS of 4 cm or greater. In some embodiments, the patient has an NRS of 6 or greater, or a VAS of 6 cm or greater. In some embodiments, the patient has an NRS of 7 or greater, or a VAS of 7 cm or greater. In some embodiments, the patient has an NRS of about 1, about 2, about 3, about 4, about 5, about 6, about 7, about 8, about 9, or about 10. In some embodiments, the patient has a VAS of about 1 cm, about 2 cm, about 3 cm, about 4 cm, about 5 cm, about 6 cm, about 7 cm, about 8 cm, about 9 cm, or about 10 cm.

For knee pain or pain associated with bone marrow lesions, in some embodiments, treatment with a nitrogen-containing bisphosphonate such as zoledronic acid may decrease the visual analog (VAS) pain score measured using a 100 mm scale, by at least about 5 mm, at least about 8 mm, at least about 10 mm, at least about 15 mm, up to about 50 mm, or up to about 100 mm. In some embodiments, the VAS score, may be decreased by at least about 5 mm, at least about 8 mm, at least about 10 mm, at least about 15 mm, up to about 50 mm, or up to about 100 mm, as compared to a placebo.

Treatment with a nitrogen-containing bisphosphonate such as zoledronic acid may decrease the numerical rating scale (NRS) pain score measured using a 0-10 scale, by at least about 0.1, at least about 0.5, at least about 0.8, at least about 1, at least about 1.5, up to about 5, or up to about 10. In some embodiments, the NRS score may be decreased by at least about 0.1, at least about 0.5, at least about 0.8, at least about 1, at least about 1.5, up to about 5, or up to about 10, as compared to a placebo.

In some embodiments, an inhibitor of osteoclast activity can be used to reduce the size of bone marrow lesions. The area of the lesions may be measured as the total area of all lesions or as the area of any one lesion. In some embodiments, the total area includes the medial tibial area, the medial femoral area, the lateral tibial area, and the lateral femoral area. In some embodiments the bone marrow lesion in located in the patella.

In some embodiments, the use of an inhibitor of osteoclast activity achieves a reduction in the total area of the bone marrow lesions of at least about 240 mm$^2$. In some embodiments, the reduction in total area is at least about 220 mm$^2$, at least about 200 mm$^2$, at least about 150 mm$^2$, at least about 100 mm$^2$, or at least about 50 mm$^2$. In some embodiments, the reduction in size of bone marrow lesions represents a reduction relative to baseline of at least about 10%, at least about 20%, at least about 30%, at least about 40%, at least about 50%, at least about 60%, at least about 70% at least about 80%, at least about 90%, or about 100%. In some embodiments, the reduction in area of bone marrow lesions represents an improvement relative to placebo of at least about 10%, at least about 20%, at least about 30%, at least about 40%, at least about 50%, at least about 60%, at least about 70%, at least about 80%, at least about 90%, at least about 100%, at least about 120%, at least about 150%, at least about 170%, at least about 200%, at least about 250%, at least about 300%, at least about 350%, at least about 400%, or at least about 450%. In some embodiments, the use of an inhibitor of osteoclast activity inhibits an increase in the size of the bone marrow lesions over time.

Joint space narrowing (JSN) is typically graded using the Osteoarthritis Research Society International (OARSI) atlas criteria, or the Kellgren and Lawrence (K/L) system. The OARSI atlas criteria grades JSN using a 0-3 scale with Grade 0 indicating an absence of JSN, and Grades 1, 2 and 3 indicating mild, moderate, and severe JSN, respectively (Altman and Gold, *Osteoarthritis Cartilage* 2007; 15(Suppl A):A1-A56). The K/L system grades JSN using a 0-4 scale with Grade 0 indicating an absence of JSN, Grade 1 indicating doubtful JSN, and grades 2, 3 and 4 indicating minimal, moderate, and severe JSN, respectively (Kellgren and Lawrence, *Ann Rheum Dis* 1957; 16:494-502). Based on these criteria, OARSI Grade 0 (absence of JSN), approximates K/L Grades 0-1 (absence of, or doubtful presence of JSN). Knee pain in a person having OARSI Grade 0 or K/L Grade or 1 JSN in the knee where the pain occurs may be referred to herein as a "normal joint space knee pain."

In some embodiments for patients having OARSI Grade 0 or K/L Grades 0-1 JSN, the use of an inhibitor of osteoclast activity achieves a reduction in the total area of the bone marrow lesions of at least about 240 mm$^2$. In some embodiments, the reduction in total area is at least about 220 mm$^2$, at least about 200 mm$^2$, at least about 150 mm$^2$, at least about 100 mm$^2$, or at least about 50 mm$^2$. In some embodiments, the reduction in size of bone marrow lesions represents a reduction relative to baseline of at least about 10%, at least about 15%, at least about 20%, at least about 25%, at least about 30%, at least about 35%, at least about 40%, at least about 45%, at least about 50%, at least about 60%, at least about 70% at least about 80%, at least about 90%, or about 100%. In some embodiments, the reduction in area of bone marrow lesions represents an improvement relative to placebo of at least about 10%, at least about 20%, at least about 30%, at least about 40%, at least about 50%, at least about 60%, at least about 70%, at least about 80%, at least about 90%, at least about 100%, at least about 120%, at least about 150%, at least about 170%, at least about 200%, at least about 250%, at least about 300%, at least about 350%, at least about 400%, or at least about 450%. In some embodiments, the use of an inhibitor of osteoclast activity inhibits an increase in the size of bone marrow lesions over time.

In some embodiments for patients having OARSI Grades 1-2 or K/L Grades 2-4 JSN, the use of an inhibitor of osteoclast activity achieves a reduction in the total area of the bone marrow lesions of at least about 100 mm$^2$. In some embodiments, the reduction in total area is at least about 50 mm$^2$, at least about 60 mm$^2$, at least about 80 mm$^2$, at least about 85 mm$^2$, at least about 90 mm$^2$, at least about 100 mm$^2$, at least about 105 mm$^2$, at least about 110 mm$^2$, or at least about 115 mm$^2$. In some embodiments, the reduction in size of bone marrow lesions represents a reduction relative to baseline of at least about 10%, at least about 20%, at least about 30%, at least about 40%, at least about 50%, at least about 60%, at least about 70% at least about 80%, at least about 90%, or about 100%. In some embodiments, the reduction in area of bone marrow lesions represents an improvement relative to placebo of at least about 10%, at least about 20%, at least about 30%, at least about 40%, at least about 50%, at least about 60%, at least about 70%, at least about 80%, at least about 90%, at least about 100%, at least about 115%, at least about 125%, at least about 135%, at least about 150%, at least about 170%, at least about 200%, at least about 250%, at least about 300%, at least about 350%, at least about 400%, or at least about 450%. In some embodiments, the use of an inhibitor of osteoclast activity inhibits an increase in the size of bone marrow lesions over time.

In some embodiments, an inhibitor of osteoclast activity, such as a nitrogen-containing bisphosphonate, including e.g. zoledronic acid, minodronic acid, etc., is used to treat fibromyalgia.

According to some embodiments, administration of an inhibitor of osteoclast activity achieves a reduction in pain that lasts at least about one month, two months, three months, four months, six months, or even at least about twelve months. According some embodiments, administration of an inhibitor of osteoclast activity achieves a reduction in pain that is observed at greater than three hours, at about one day, at about two to about five days, at about one week, at about two weeks, at about three weeks, at about one month, at about five weeks, at about six weeks, at about seven weeks, at about two months, at about nine weeks, at about ten weeks, at about eleven weeks, at about three months, at about four months, at about six months, or at about twelve months after administration of the inhibitor of osteoclast activity.

According some embodiments, administration of an inhibitor of osteoclast activity achieves a reduction in pain that is observed at greater than three hours, but at or before one week, two weeks, three weeks, four weeks, five weeks, six weeks, seven weeks, eight weeks, nine weeks, ten weeks, eleven weeks, twelve weeks, four months, five months, or six months.

According some embodiments, administration of an inhibitor of osteoclast activity achieves a reduction in pain that is observed at greater than three hours with a duration of no more than about three months, no more than about four months, no more than about five months, or no more than about six months.

According to some embodiments, after the administration of an inhibitor of osteoclast activity, the area of bone marrow lesions relative to the size prior to administration remains reduced for up to three months, four months, five months, six months, or even up to twelve months or more. According to some embodiments, after the administration of an inhibitor of osteoclast activity, the area of bone marrow lesions relative to the size prior to administration is reduced at about three months, at about four months, at about five months, at about six months, or at about twelve months.

According to some embodiments, after administration of an inhibitor of osteoclast activity, the size of Modic changes or VESCs relative to the size prior to administration remains reduced for up to three months, four months, five months, six months, or even up to twelve months or more. According to some embodiments, after the administration of an inhibitor of osteoclast activity, the size of Modic changes or VESCs relative to the size prior to administration is reduced at about three months, at about four months, at about five months, at about six months, or at about twelve months.

In some embodiments, an osteoclast inhibitor, such as a nitrogen-containing bisphosphonate, e.g. zoledronic acid, ibandronic acid or minodronic acid, may be administered to relieve complex regional pain syndrome, such as complex regional pain syndrome type I (CRPS-I), complex regional pain syndrome type II (CRPS-II), CRPS-NOS, or another type of CRPS.

In some embodiments, zoledronic acid or another bisphosphonate may be administered orally to relieve complex regional pain syndrome, such as complex regional pain syndrome type I (CRPS-I), complex regional pain syndrome type II (CRPS-II), CRPS-NOS, or another type of CRPS. CRPS is a type of inflammatory pain. CRPS can also have a neuropathic component.

Complex regional pain syndrome is a debilitating pain syndrome. It is characterized by severe pain in a limb that can be accompanied by edema, and autonomic, motor and sensory changes.

In some embodiments, an osteoclast inhibitor, such as a nitrogen-containing bisphosphonate, e.g. zoledronic acid or minodronic acid, may be used to reduce the use of non-steroidal anti-inflammatory drug (NSAIDs), opioids, or other pain medications, for a patient suffering from pain, inflammation, a similar condition, or any condition described herein. For example, use of NSAIDs, opioids, or other pain medications may be reduced by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, up to about 100%, as compared to the use of NSAIDs, opioids or other pain medications without administration of the osteoclast inhibitor. Use of the opioids, NSAIDs, or other pain medications may be reduced by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, up to about 100%, as compared to the use of NSAIDS, opioids, or other pain medications at baseline.

The reduction in the use of NSAIDs, opioids, or other pain medications may be observed at about one week, about two weeks, about three weeks, about one month, about two months, about three months, about four months, about five months, about six months, about seven months, about eight months, about nine months, about 10 months, about 11 months, or about one year or more, after the administration of osteoclast inhibitor.

With respect to use of oral zoledronic acid in a disodium salt form or in an acid form for relieving pain associated with an inflammatory condition or Paget's disease of bone, relief of pain can be short-term, e.g. for a period of hours after administration of the dosage form, and/or relief of pain can be long-term, e.g. lasting for days, weeks, or even months after oral administration of zoledronic acid. In some embodiments, a mammal, such as a human being, experiences significant pain relief at least about 3 hours, at least about 6 hours, at least about 12 hours, at least about 24 hours, at least about 48 hours, at least about one week, at least about 2 weeks, or at least about 3 weeks after administration of an oral dosage form comprising zoledronic acid. In some embodiments, a mammal, such as a human being, experiences significant pain relief during at least part of the time from about 3 hours to about 2 weeks, about 3 hours to about 3 weeks, about 3 hours to about 24 hours, about 6 hours to about 2 weeks, or about 6 hours to about 24 hours, about 3 days to about 2 weeks, about 6 days to about 2 weeks, after administration of an oral dosage form comprising zoledronic acid. In some embodiments, a human being treated has significant pain relief at one month, three months, six months, nine months, one year, 5 years, or longer, after administration of the most recent dose of an osteoclast inhibitor such as zoledronic acid.

With respect to the treatment of any condition recited herein, in some embodiments a first oral dosage form comprising zoledronic acid is administered and a second oral dosage form comprising oral zoledronic acid is administered. The timing of the administration of the two dosage forms may be such that, with respect to the first oral dosage form, the second oral dosage with respect to the first oral dosage form, the second oral dosage form is administered at $5 \times T_{max}$ or greater (e.g., if $T_{max}$ is 1 hour, at 5 hours or later), at least $10 \times T_{max}$ or greater, at least about $15 \times T_{max}$ or greater, at least about $20 \times T_{max}$ or greater, at least about $50 \times T_{max}$ or greater, or at least about $200 \times T_{max}$ or greater, wherein $T_{max}$ is the time of maximum plasma concentration for the first oral dosage form.

Some embodiments include treatment of a condition recited herein, such as inflammatory pain, arthritis, or complex regional pain syndrome, wherein the treatment comprises either: administering only one dosage form to a mammal to treat the condition, or administering a first dosage form to the mammal, followed by administering a second dosage form to the mammal. If two or more dosage forms are administered, the second oral dosage form is administered before the maximum pain relieving effect of the first oral dosage form is achieved, or before a peak in the pain relieving effect of the first oral dosage form is experienced by a mammal, receiving the dosage form. In some embodiments, the second oral dosage form is administered before an observable pain relieving effect is achieved. In some embodiments, the second dosage form is administered about 12 hours to about 60 days, about 24 hours to about 28 days, about 24 hours to about 7 days, about 24 hours to about 14 days, or about 24 hours to about 21 days, after the first dosage form is administered.

Some embodiments include treatment of a condition recited herein, such as inflammatory pain, arthritis, or complex regional pain syndrome, wherein the treatment comprises administering a first dosage form to the mammal, followed by administering a second dosage form to the mammal, wherein the second dosage form is administered after the maximum pain relieving effect of the first oral dosage form is achieved, and the second oral dosage form is administered while the mammal is still experiencing pain relief from the first oral dosage form, or while the pain relieving effect from the first oral dosage form is observable. In some embodiments, the second dosage form is administered about 12 hours to about 60 days, about 24 hours to about 28 days, about 24 hours to about 7 days, about 24 hours to about 14 days, or about 24 hours to about 21 days, after the first dosage form is administered.

Zoledronic acid or another bisphosphonate may also be administered orally to relieve cancer-related pain, including pain associated with multiple myeloma and bone metastases from solid tumors. In some embodiments, zoledronic acid is used to treat pain that is not cancer-related pain. For example, zoledronic acid may be used to treat pain that is not associated with multiple myeloma, bone metastasis from solid tumors, hypercalcemia of malignancy, giant cell tumor of bone, blood cancers or leukemias, or solid tumors or cancers. In some embodiments, enhanced bioavailability of the zoledronic acid may be achieved in treating one of these conditions by administering a dosage form comprising zoledronic acid in the form of a disodium salt. This may allow a reduced molar amount of the disodium salt to be used as compared to what would be used with the diacid form.

In addition to relieving pain, oral administration of zoledronic acid or another bisphosphonate may also be useful to treat diseases or conditions that may or may not include a pain component. For example, zoledronic acid or another bisphosphonate may be useful to treat any of the pain conditions or types of conditions listed above, including treatment that does not simply relieve the pain of those conditions, and treatment that is carried out in such a way that the condition is treated without pain relief occurring. In addition to any pain relief zoledronic acid or another bisphosphonate may or may not provide, zoledronic acid or another bisphosphonate may be used to treat a disease or condition such as a metabolic disease or condition; an inflammatory disease or condition, including an inflammatory disease or condition that is not associated with pain; a cancer disease or condition; a neurological disease or condition; etc. In some embodiments, enhanced bioavailability of the zoledronic acid may be achieved in treating one of these conditions by administering a dosage form comprising zoledronic acid in the form of a disodium salt. This may allow a reduced molar amount of the disodium salt to be used as compared to what would be used with the diacid form.

In some embodiments, oral administration of zoledronic acid or another bisphosphonate may also be useful to treat complex regional pain syndrome, rheumatoid arthritis, osteoarthritis, erosive osteoarthritis, axial spondyloarthritis including ankylosing spondylitis, acute vertebral crush fracture, fibrous dysplasia, SAPHO syndrome, osteoporosis, transient osteoporosis, or transient osteoporosis of the hip. In some embodiments, enhanced bioavailability of the zoledronic acid may be achieved in treating one of these conditions by administering a dosage form comprising zoledronic acid in the form of a disodium salt. This may allow a reduced molar amount of the disodium salt to be used as compared to what would be used with the diacid form.

In some embodiments, oral administration of zoledronic acid or another bisphosphonate may also be useful to treat hypercalcemia of malignancy, multiple myeloma, bone metastases from solid tumors, Paget's disease of bone, giant cell tumor of bone, blood cancers or leukemias, or solid tumors or cancers. In some embodiments, enhanced bioavailability of the zoledronic acid may be achieved in treating one of these conditions by administering a dosage form comprising zoledronic acid in the form of a disodium salt. This may allow a reduced molar amount of the disodium salt to be used as compared to what would be used with the diacid form.

Some nitrogen-containing bisphosphonates may be represented by Formula A:

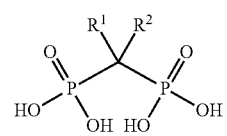

Formula A

With respect to Formula A, $R^1$ is F, Cl, Br, H, or OH. In some embodiments, $R^1$ is OH.

With respect to Formula A, $R^2$ is aminoalkyl, such as aminoethyl, aminopropyl, aminopentyl, dimethylaminoethyl, methylpentylaminoethyl, etc; or optionally substituted heterocyclyl alkyl, such as optionally substituted imidazolylmethyl, optionally substituted pyridinymethyl, etc. In some embodiments $R^2$ is optionally substituted imidazolylalkyl.

Unless otherwise indicated, when a compound or chemical structural feature such as heterocyclyl alkyl is referred to as being "optionally substituted," it includes a feature that has no substituents (i.e. unsubstituted), or a feature that is substituted, meaning that the feature has one or more substituents. The term "substituent" has the broadest meaning known to one of ordinary skill in the art, and includes a moiety that replaces one or more hydrogen atoms in a parent compound or structural feature. The term "replaces" is merely used herein for convenience, and does not require that the compound be formed by replacing one atom with another. In some embodiments, a substituent may be any ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, a substituent comprises, or consists of: 0-30, 0-20, 0-10, or 0-5 carbon atoms; and 0-30, 0-20, 0-10, or 0-5 heteroatoms, wherein each heteroatom may independently be: N, O, P, S, Si, F, Cl, Br, or I; provided that the substituent includes one C, N, O, P, S, Si, F, Cl, Br, or I atom. In some embodiments, substituents can independently have a molecular weight of about 15 Da to about 600 Da and can consist of 2 to 5 chemical elements, wherein the chemical elements are independently C, H, O, N, P, S, Si, F, Cl, or Br. In some embodiments, a substituent is optionally substituted alkyl, —O-alkyl (e.g. —OCH$_3$, —OC$_2$H5, —OC$_3$H$_7$, —OC$_4$H$_9$, etc.), —S-alkyl (e.g. —SCH$_3$, —SC$_3$H$_7$, —SC$_4$H$_9$, etc.), —NR'R", —OH, —SH, —CN, —CF$_3$, —NO$_2$, perfluoroalkyl, optionally substituted aryl, optionally substituted heteroaryl, optionally substituted amine or a halogen, wherein R' and R" are independently H or optionally substituted alkyl. Wherever a substituent is described as "optionally substituted," that substituent can be substituted with the above substituents.

For convenience, the term "molecular weight" is used with respect to a moiety or part of a molecule to indicate the sum of the atomic masses of the atoms in the moiety or part of a molecule, even though it may not be a complete molecule.

Examples of nitrogen-containing bisphosphonates include but are not limited to pamidronic acid, incadronic acid, ibandronic acid, risedronic acid, minodronic acid, cimadronic acid, neridronic acid, alendronic acid, olpadronic acid, zoledronic acid, etc.

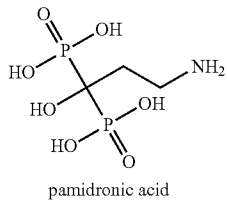

pamidronic acid

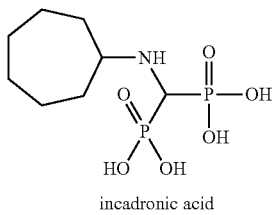

incadronic acid

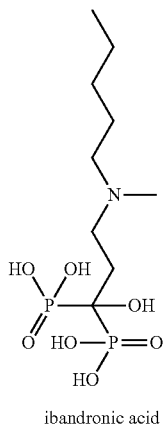

ibandronic acid

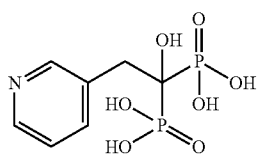

risedronic acid

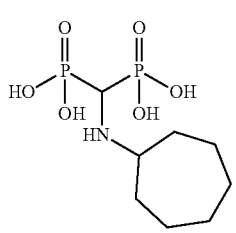

cimadronic acid

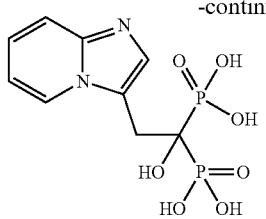

minodronic acid

Zoledronic acid has the structure shown below, and is also referred to as zoledronate.

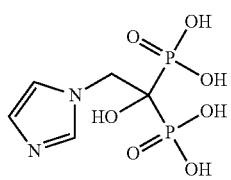

Zoledronic acid

Unless otherwise indicated, any reference to a compound herein, such as zoledronic acid, by structure, name, or any other means, includes pharmaceutically acceptable salts, such as the disodium salt; alternate solid forms, such as polymorphs, solvates, hydrates, etc.; tautomers; or any other chemical species that may rapidly convert to a compound described herein under conditions in which the compounds are used as described herein. Unless otherwise indicated, a phrase such as "administering a bisphosphonate," "administering an osteoclast inhibitor," "administering zoledronic acid," includes administering any form of the bisphosphonate, osteoclast inhibitor, zoledronic acid, etc., such as those recited above.

In some embodiments, zoledronic acid is administered in a dosage form comprising a salt form, such as a salt of a dianion of zoledronic acid. In some embodiments, zoledronic acid is administered in a dosage form comprising a disodium salt form of zoledronic acid. In some embodiments, zoledronic acid is administered in a sodium salt form, such as a monosodium salt, a disodium salt, a trisodium salt, etc. In some circumstances, use of the disodium salt may be desirable. For example, the disodium salt is much more soluble in water than the diacid form. As a result, in some processes, the disodium salt can be easier to work with than the diacid form. Additionally, the sodium salt may be more bioavailable and/or more rapidly absorbed when taken orally as compared to the diacid form.

In some embodiments, a RANK/RANKL antagonists or an osteoclast inhibitor, such as zoledronic acid or neridronic acid may be in the form of a molecular complex. For example, molecular complexes of zoledronic acid include cocrystals, salts, solvates such as hydrates and mixed solvates of an acid or a salt form, and mixtures containing such materials. Molecular complexes of zoledronic acid may be in amorphous forms or polymorphs.

Of particular interest are compositions, or complexes comprising zoledronic acid or neridronic acid and the standard amino acids or natural existing amino acids, such as alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, etc. Some examples of useful molecular complexes include, but are not limited to, complexes of zoledronic acid or neridronic acid with sodium cation, ammonium, ammonia, L-lysine, DL-lysine, nicotinamide, adenine, glycine, and Selenocysteine.

Zoledronic acid may also be in a form represented by one of the structural depictions below.

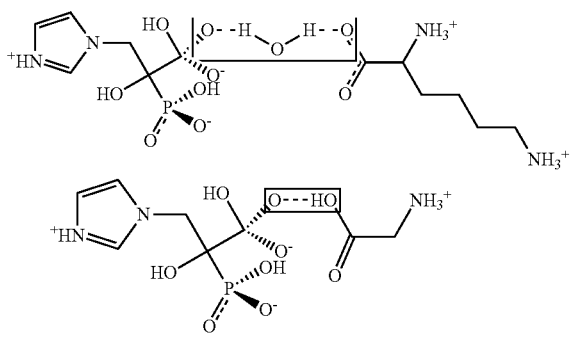

Zoledronic acid in a salt or an acid form may be present in a molecular complex having strong X-ray powder diffraction peaks in one of the following positions:

| Form | strong X-ray powder diffraction peaks (°2θ ± 0.2) |
| --- | --- |
| zoledronic acid, sodium zoledronate and water complex | about 8.1, about 13.3, about 21.5, about 24.6, and about 25.6 |
| ammonium zoledronate salt and water complex | about 11.0, about 14.6, about 15.4, about 19.9, and about 29.4 |
| zoledronic acid, L-lysine, and water complex | about 9.0, about 14.4, about 18.1, about 26.0, and about 29.6 |
| zoledronic acid, DL-lysine, and water complex | about 9.1, about 14.7, about 18.0, about 21.2, and about 26.0 |
| zoledronic acid, DL-lysine, ethanol, and water complex | about 8.8, about 9.7, about 17.6, about 23.1, and about 26.5 |
| zoledronic acid, nicotinamide, and water complex | 13.1, about 15.2, about 21.0, about 23.9, and about 26.5 |
| zoledronic acid, adenine, and water complex | about 13.6, about 15.9, about 19.7, about 27.9, and about 29.5 |
| zoledronic acid and glycine complex | about 10.2, about 17.8, about 19.9, about 22.9, and about 28.1 |
| zoledronic acid diammonia, and water complex | about 12.2, about 13.0, about 14.1, about 17.1, and about 19.3 |
| zoledronic acid, DL-lysine, and water complex | about 8.3, about 11.8, about 12.3, about 15.8, and about 20.8 |
| zoledronic acid, L-lysine, and water complex | about 9.6, about 10.7, about 14.3, about 21.4, and about 23.5 |
| zoledronic acid, DL-lysine, and water complex | about 9.7, about 10.8, about 14.4, about 18.9, and about 21.4 |
| zoledronic acid, DL-lysine complex | 7.2, about 14.0, about 18.3, about 19.1, about 20.7, about 24.6, and about 34.4 |
| zoledronic acid, DL-lysine complex | 6.6, about 11.0, about 14.2, about 18.3, about 19.7, about 22.7, and about 27.6 |

Solid forms of zoledronic acid such as complexes of zoledronic acid with sodium, ammonium, ammonia, L-lysine, DL-lysine, nicotinamide, adenine and glycine may be prepared by methods such as dry or solvent-drop grinding (liquid assisted grinding), heating or solvent evaporation of their solution in single or mixed solvent systems, slurry suspension, supercritical fluids or other techniques known to a person skilled in the art.

For example, zoledronic acid and nicotinamide may be complexed by dissolving both compounds in water:ethyl acetate (1:1 v/v) and allowing the solvents in the mixture to evaporate to form crystalline material.

In some embodiments, a zoledronic acid complex may have an excess at least one coformer (e.g. the component other than zoledronic acid) to the zoledronic acid complexes, which may be the same as the coformer in the complex, a different coformer, or a mixture thereof. In some embodiments, the excess coformer may be a standard or natural amino acid. Examples of compounds in salt forms containing Ion 1 are shown below:

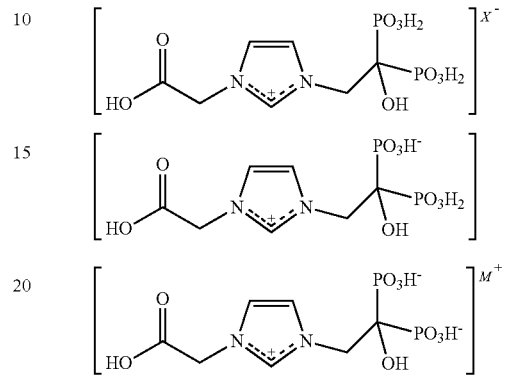

-continued

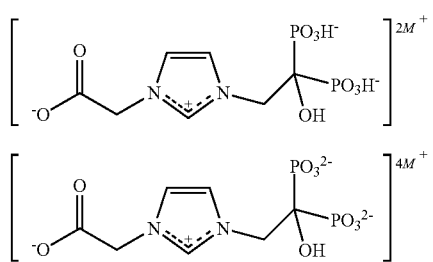

wherein X⁻ is any suitable anion, e.g. F⁻, Br⁻, Cl⁻, I⁻, OH⁻, acetate, etc.; and M⁺ is any suitable cation, e.g. Na⁺, K⁺, NH₄⁺, etc. Many other salt forms are also possible.

In some embodiments, a compound containing Ion 1 may be further represented by a formula,

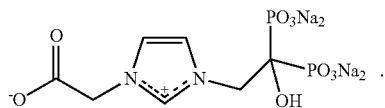

In some embodiments, a compound containing Ion 1 may be in a hydrate form.

In some embodiments, a compound containing Ion 1 is administered in a dosage form comprising a salt form, such as a zwitterionic form, or a salt of a cation, a monoanion, a dianion, a trianion, etc.

A compound containing Ion 1 can be present in any amount, such as less than about 100% w/w, less than about 50% w/w, less than about 20% w/w, less than about 10% w/w, less than about 1% w/w, less than 0.1% w/w, less than about 0.07% w/w, less than about 0.05% w/w, less than about 0.04% w/w, less than about 0.03% w/w, less than about 0.02% w/w; and/or greater than 0% w/w, at least about 0.00000001% w/w, at least about 0.000001% w/w, or at least about 0.00001% w/w, based upon the total amount of zoledronic acid, a compound containing Ion 1, and a compound containing Ion 2 present in the composition.

Examples of salts of compounds containing Ion 2 are shown below:

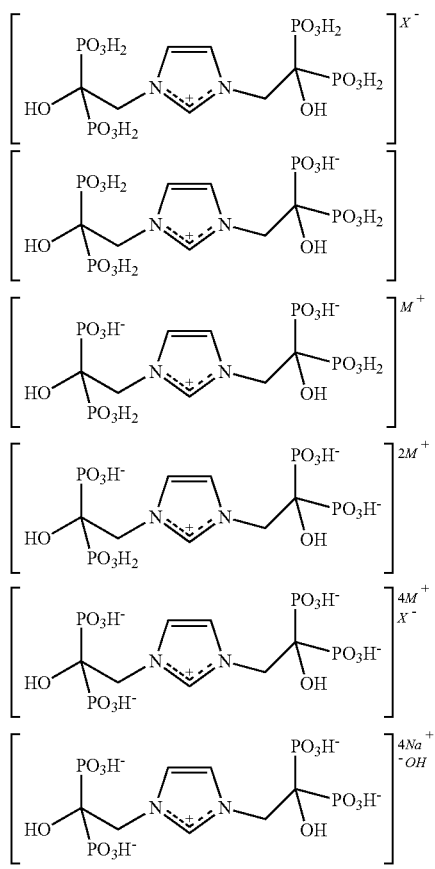

wherein X⁻ is any suitable anion, e.g. F⁻, Br⁻, Cl⁻, I⁻, OH⁻, acetate, etc.; and M⁺ is any suitable cation, e.g. Na⁺, K⁺, NH₄⁺, etc. Many other salt forms are also possible.

In some embodiments, a salt of a compound containing Ion 2 may be further represented by a formula,

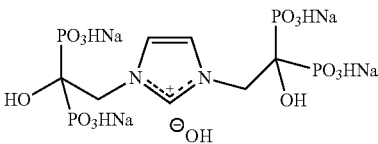

In some embodiments, a compound containing Ion 2 may be in a hydrate form.

In some embodiments, a compound containing Ion 2 is administered in a dosage form comprising a salt form, such as a zwitterionic form, or a salt of a cation, a monoanion, a dianion, a trianion, etc.

A compound containing Ion 2 can be present in any amount, such as less than about 100% w/w, less than about 50% w/w, less than about 20% w/w, less than about 10% w/w, less than about 1% w/w, less than about 0.3% w/w, less than about 0.2%, less than 0.1% w/w, less than about 0.08% w/w, less than about 0.07% w/w, less than about 0.05% w/w, less than about 0.04% w/w, less than about 0.03% w/w, less than about 0.02% w/w; and/or greater than 0% w/w, at least about 0.00000001% w/w, at least about 0.000001% w/w, or at least about 0.00001% w/w, based upon the total amount of zoledronic acid, a compound containing Ion 1, and a compound containing Ion 2 present in the composition.

In some embodiments, a compound containing Ion 1 and a compound containing Ion 2 are present in an amount that is less than 0.1% w/w.

In some embodiments, the administration of an osteoclast inhibitor, such as a nitrogen-containing bisphosphonate, including, e.g. zoledronic acid, minodronic acid, etc., to a patient or mammal in need thereof affects Modic changes (MCs). For example, any of the above compounds could be used to treat Modic changes, or vertebral endplate signal changes (VESC) and bone marrow changes visible using magnetic resonance imaging (MRI), or neck pain or back pain associated with Modic changes.

Modic changes, as used herein, includes its ordinary meaning in the art and refers to pathological vertebral endplate and bone marrow changes visible using magnetic resonance imaging (MRI). Modic changes may also be referred to as vertebral endplate signal changes (VESC). Modic changes, can be classified into various types including type 1 (M1), type 2 (M2), and type 3 (M3) lesions or changes, any of which may be treated using an osteoclast inhibitor, such as a nitrogen-bisphosphonate, including, e.g. zoledronic acid, minodronic acid, etc. Different types of Modic changes may occur in the same patient, for example type 1 and type 2 Modic changes (M1/2). In some cases, M1 changes are related to lower back pain than other types of Modic change.

VESCs may be found in patients with different types of low back pain including but not limited to spondylitis, trauma, spondyloarthropathies including ankylosing spondylitis, Schmorl's nodes, fracture, tumor, and spinal cord infarction. Lesions in ankylosing spondylitis include osteitis and spondylodiscitis, which can be detected using MRI or another medical imaging instrument.

Modic changes may be found in the cervical, thoracic, lumbar, and sacral spine. Modic changes may be found at various spinal levels such as at C1/2, C2/3, C3/4, C4/5, C5/6, C6/7, C7/T1, T1/2, T2/3, T3/4, T4/5, T5/6, T6/7, T7/8, T8/9, T9/10, T10/11, T11/12, T12/L1, L1/2, L2/3, L3/4, L4/5, L5/S1, etc., any of which may be treated using an osteoclast inhibitor, such as a nitrogen-bisphosphonate, including, e.g. zoledronic acid, minodronic acid, etc.

In some embodiments, the Modic change being treated is located at L2/3. In some embodiments, the Modic change being treated is located at L3/4. In some embodiments, the Modic change being treated is located at L4/5. In some embodiments, the Modic change being treated is located at L5/S1.

In some embodiments, the Modic change being treated is located at C3/4. In some embodiments, the Modic change being treated is located in at C4/5. In some embodiments, the Modic change being treated is located in at C5/6. In some embodiments, the Modic change being treated is located in at C6/7.

In some embodiments, the Modic change being treated is located at T5/6. In some embodiments, the Modic change being treated is located in at T6/7. In some embodiments, the Modic change being treated is located in at T7/8. In some embodiments, the Modic change being treated is located in at T8/9. In some embodiments, the Modic change being treated is located at T9/10.

In some embodiments, the patient being treated has predominantly M1. In some embodiments, the patient being treated has predominantly M1/M2. In some embodiments, the patient being treated has predominantly M2. In some embodiments, the patient being treated has predominantly M3.

In some embodiments, the worst type of lesion that the patient being treated has is M1. In some embodiments, the worst type of lesion that the patient being treated has is M1/2. In some embodiments, the worst type of lesion that the patient being treated has is M2.

In some embodiments, the patient being treated has Modic changes at more two or more levels. In some embodiments the patient being treated has Modic changes at three or more levels. In some embodiments greater pain relief is obtained when treating a patient with Modic changes at two levels, or three or more levels, than is obtained when treating a patient with Modic changes at a single level or at two levels.

In some embodiments greater pain relief is obtained when treating a patient with Modic changes at two levels than is obtained when treating a patient with Modic changes at a single level.

In some embodiments greater pain relief is obtained when treating a patient with Modic changes at three or more levels than is obtained when treating a patient with Modic changes at a single level.

In some embodiments greater pain relief is obtained when treating a patient with Modic changes three or more levels than is obtained when treating a patient with Modic changes at two levels.

In some embodiments, the inhibitor of osteoclast activity may be used to effect a reduction in the levels of pro-inflammatory cytokines in the patient with low back pain or any other type of pain or condition recited herein. In some embodiments greater pain relief may be obtained in patients with greater baseline levels of pro-inflammatory cytokines when treated with an inhibitor of osteoclast activity, such as a nitrogen-containing bisphosphonate, including e.g. zoledronic acid, minodronic acid, etc. In some embodiments, greater pain relief may be obtained in patients who experience a reduction or a greater reduction in the levels of pro-inflammatory cytokines when treated with an inhibitor of osteoclast activity, such as a nitrogen-containing bisphosphonate, including e.g. zoledronic acid, minodronic acid, etc. Pro-inflammatory cytokines include but are not limited to IL-1, IL-2, IL-3, IL-6, IL-8, IL-10, IL-12, tumor necrosis alpha (TNF-alpha), interferon gamma, etc.

In some embodiments, the use of an inhibitor of osteoclast activity, such as a nitrogen-containing bisphosphonate, including e.g. zoledronic acid, minodronic acid, etc., to a patient or mammal in need thereof, achieves a reduction relative to baseline in the size of Modic changes or VESCs of at least about 5%, at least about 10%, at least about 15%, at least about 20%, at least about 25%, at least about 30%, at least about 40%, at least about 50%, at least about 60%, at least about 70% at least about 80%, at least about 90%, or about 100%. In some embodiments, the reduction the size of Modic changes or VESCs represents an improvement relative to placebo of at least about 10%, at least about 15%, at least about 20%, at least about 25%, at least about 30%, at least about 40%, at least about 50%, at least about 60%, at least about 70%, at least about 80%, at least about 90%, at least about 100%, at least about 120%, at least about 150%, at least about 170%, at least about 200%, at least about 250%, at least about 300%, at least about 350%, at least about 400%, or at least about 450%. In some embodiments, the use of an inhibitor of osteoclast activity inhibits an increase in the size of Modic changes or VESCs over time.

The oral bioavailability of zoledronic acid may be enhanced by orally administering the zoledronic acid in the disodium salt form. For example, the bioavailability of zoledronic acid may be improved by at least about 10%, at least about 20%, at least about 30%, at least about 50%, and/or up to about 100%, or up to about 200%, as compared to administration of zoledronic acid in the diacid form.

Because of the improved bioavailability of the disodium salt a dosage form may contain, or a mammal, such as a human being, may receive, on a molar basis, less of the disodium salt form of zoledronic acid than would otherwise be administered of the diacid form of zoledronic acid. For example, a dosage form may contain, or a mammal may receive, at least about 10 mole % less, at least about 20 mole % less, at least about 40 mole % less, at least about 50 mole % less, and/or up to about 90 mole % less or 95 mole % less, of the disodium salt form as compared the amount of the diacid form of zoledronic acid that would otherwise be administered, such as a molar amount that would be administered of zoledronic acid in the diacid form in order to achieve the same plasma levels of zoledronic acid.

In some embodiments, a dosage form contains, or a mammal (such as a human being) is administered, an amount of the disodium salt form, on a molar basis, that has a value of about $0.8n_d$ to about $1.2n_d$ or about $0.9n_d$ to about $1.1n_d$, wherein:

$$n_d = (b_d/b_d)(n_a)$$

wherein $b_a$ is the bioavailability of the diacid form, $b_d$ is the bioavailability of the disodium salt form, and $n_a$ is the number of moles of the diacid that would be administered in a dosage form containing the diacid form of zoledronic acid. For example, if the diacid form has a bioavailability ($b_a$) of 0.01 and the disodium salt form has a bioavailability ($b_d$) of 0.015, and a dosage form would normally contain 0.001 moles of the diacid, $n_d$ would be (0.01/0.015)(0.001 moles), or about 0.00067 moles. In some embodiments, the disodium salt is administered in an amount that has a value of about $n_d$.

With respect to oral dosage forms comprising a reduced molar amount of the disodium salt of zoledronic acid as compared to the diacid form of zoledronic acid, in some embodiments, the bioavailability of the zoledronic acid in the disodium salt form is sufficiently high that, if the drug is administered to a mammal, at least as much zoledronic acid is present in the blood of the mammal as would be present if zoledronic acid were administered in the diacid form.

With respect to oral dosage forms comprising the disodium salt form of zoledronic acid, in some embodiments, the disodium salt form is present in a lower molar amount than would be present if the zoledronic acid were in the diacid form; and the zoledronic acid in the disodium salt form has an improved bioavailability as compared to the zoledronic acid in the diacid form to the extent that the lower molar amount of the disodium salt in the dosage form does not reduce the amount of zoledronic acid delivered to the plasma of a mammal.

Some oral dosage forms comprising zoledronic acid have a dose of zoledronic acid and a configuration suitable for a particular species of mammal, e.g. dog, rat, human, etc. Such a dosage form may have zoledronic acid present in an amount that results in a desired range for an area under the plasma concentration curve (AUC) of zoledronic acid in that particular species of mammal. For example the dose of zoledronic acid and a configuration of the oral dosage form may result in an AUC of zoledronic acid of about 1 ng·h/mL to about 700 ng·h/mL, about 3 ng·h/mL to about 30 ng·h/mL, about 3 ng·h/mL to about 10 ng·h/mL, about 50 ng·h/mL to about 700 ng·h/mL, about 130 ng·h/mL to about 180 ng·h/mL, about 300 ng·h/mL to about 450 ng·h/mL, about 300 ng·h/mL to about 350 ng·h/mL, about 300 ng·h/mL to about 310 ng·h/mL, about 340 ng·h/mL to about 350 ng·h/mL, about 370 ng·h/mL to about 420 ng·h/mL, about 380 ng·h/mL to about 390 ng·h/mL, about 405 ng·h/mL to about 415 ng·h/mL, about 140 ng·h/mL to about 160 ng·h/mL, about 140 ng·h/mL to about 150 ng·h/mL, about 150 ng·h/mL to about 160 ng·h/mL, about 140 ng·h/mL, 142 ng·h/mL, about 155 ng·h/mL, about 305 ng·h/mL, 304 ng·h/mL, about 345 ng·h/mL, 343 ng·h/mL, about 385 ng·h/mL, 384 ng·h/mL, about 410 ng·h/mL, or any AUC in a range bounded by, or between, any of these values, upon administration of the oral dosage form to a mammal.

Unless otherwise indicated, the AUC refers to the AUC calculated to the last measured concentration ($AUC_{(0-t)}$) and extrapolated to infinity ($AUC_{(0-inf)}$).

An oral dosage form comprising zoledronic acid having a dose of zoledronic acid and a configuration suitable for a particular species of mammal may have zoledronic acid present in an amount that results in a $C_{max}$ of zoledronic acid of about 0.2 ng/mL to about 300 ng/mL, about 0.5 ng/mL to about 5 ng/mL, about 5 ng/mL to about 300 ng/mL, about 5 ng/mL to about 50 ng/mL, about 20 ng/mL to about 50 ng/mL, about 30 ng/mL to about 50 ng/mL, about 50 ng/mL to about 200 ng/mL, about 50 ng/mL to about 150 ng/mL, about 80 ng/mL to about 120 ng/mL, about 90 ng/mL to about 100 ng/mL, about 50 ng/mL to about 200 ng/mL, about 40 ng/mL, about 95 ng/mL, about 97 ng/mL, or any $C_{max}$ in a range bounded by, or between, any of these values, upon administration of the oral dosage form to a mammal.

An oral dosage form comprising zoledronic acid having a dose of zoledronic acid and a configuration suitable for a particular species of mammal may be configured so that administration of the oral dosage form to the particular species of mammal results in a $T_{max}$ of zoledronic acid of about 0.4 hr to about 1 hr, about 0.5 hr, or about 0.75 hr, or any $T_{max}$ in a range bounded by, or between, any of these values.

In some embodiments, the zoledronic acid in the disodium salt form is present in an amount such that the oral dosage form provides an area under the plasma concentration curve of zoledronic acid of about 4 ng·h/mL to about 2000 ng·h/mL to the mammal each time the zoledronic acid in the disodium salt is administered.

In some embodiments, the zoledronic acid, including zoledronic acid in an acid or a salt form, e.g the disodium salt form, is present in an amount such that the oral dosage form provides an area under the plasma concentration curve of zoledronic acid of about 100 ng·h/mL to about 2000 ng·h/mL, about 100 ng·h/mL to about 1000 ng·h/mL, about 500 ng·h/mL to about 1000 ng·h/mL, or about 500 ng·h/mL to about 700 ng·h/mL in the mammal to which the dosage form is administered. This amount may be suitable for administration of the oral dosage form about every 3 to 4 weeks.

In some embodiments, the zoledronic acid, such as zoledronic acid in an acid form or a salt form, such as the disodium salt form, is present in an amount such that the oral dosage form provides an area under the plasma concentration curve (AUC) of zoledronic acid of about 20 ng·h/mL to about 700 ng·h/mL, about 50 ng·h/mL to about 500 ng·h/mL, about 50 ng·h/mL to about 400 ng·h/mL, about 50 ng·h/mL to about 300 ng·h/mL, about 50 ng·h/mL to about 200 ng·h/mL, about 50 ng·h/mL to about 100 ng·h/mL, about 130 ng·h/mL to about 150 ng·h/mL, about 130 ng·h/mL to about 140 ng·h/mL, about 150 ng·h/mL to about 200 ng·h/mL, about 200 ng·h/mL to about 300 ng·h/mL, about 250 ng·h/mL to about 300 ng·h/mL, about 300 ng·h/mL to about 400 ng·h/mL, about 400 ng·h/mL to about 500 ng·h/mL, about 350 ng·h/mL to about 400 ng·h/mL, about 450 ng·h/mL to about 500 ng·h/mL, about 130 ng·h/mL to about 160 ng·h/mL, about 405 ng·h/mL to about 450 ng·h/mL, about 100 ng·h/mL to about 500 ng·h/mL, about 100 ng·h/mL to about 400 ng·h/mL, about 100 ng·h/mL to about 300 ng·h/mL, about 100 ng·h/mL to about 200 ng·h/mL, about 125 ng·h/mL to about 500 ng·h/mL, about 125 ng·h/mL to about 400 ng·h/mL, about 125 ng·h/mL to about 300 ng·h/mL, about 125 ng·h/mL to about 200 ng·h/mL, or about 200 ng·h/mL to about 300 ng·h/mL, in the mammal to which the dosage form is administered. This amount may be suitable for weekly administration of the oral dosage, or for administration of 3 to 5 individual dosages during a month. The individual dosages could be given at regular intervals, given during the first week, or at any other schedule that provides 3 to 5 dosages during the month.

In some embodiments, the zoledronic acid is present in an amount such that the oral dosage form provides an area under the plasma concentration curve of zoledronic acid of about 4 ng·h/mL to about 100 ng·h/mL, about 10 ng·h/mL to about 50 ng·h/mL, about 10 ng·h/mL to about 30 ng·h/mL, 20 ng·h/mL to about 700 ng·h/mL, about 50 ng·h/mL to about 500 ng·h/mL, about 50 ng·h/mL to about 400 ng·h/mL, about 50 ng·h/mL to about 300 ng·h/mL, about 50 ng·h/mL to about 200 ng·h/mL, about 100 ng·h/mL to about 500 ng·h/mL, about 100 ng·h/mL to about 400 ng·h/mL, about 100 ng·h/mL to about 300 ng·h/mL, about 100 ng·h/mL to about 200 ng·h/mL, about 125 ng·h/mL to about 500 ng·h/mL, about 125 ng·h/mL to about 400 ng·h/mL, about 125 ng·h/mL to about 300 ng·h/mL, about 125 ng·h/mL to about 200 ng·h/mL, or about 200 ng·h/mL to about 300 ng·h/mL in the mammal to which the dosage form is administered. This amount may be suitable for daily administration of the oral dosage form. In some embodiments, the dosage form may be administered for 2, 3, 4, 5, 6, 7, 8, 9, or 10, 5 to 10, or 6 to 10 consecutive days.

In some embodiments, the zoledronic acid, such as zoledronic acid in an acid form or a salt form, such as the disodium salt form, is present in an amount such that the oral administration of the dosage form in a fasted state results in an area under the plasma concentration curve (AUC) of zoledronic acid of about 50 ng·h/mL to about 500 ng·h/mL, about 50 ng·h/mL to about 100 ng·h/mL, about 100 ng·h/mL to about 200 ng·h/mL, about 130 ng·h/mL to about 180 ng·h/mL, about 130 ng·h/mL to about 150 ng·h/mL, about 130 ng·h/mL to about 140 ng·h/mL, about 140 ng·h/mL to about 150 ng·h/mL, about 150 ng·h/mL to about 200 ng·h/mL, about 200 ng·h/mL to about 300 ng·h/mL, about 250 ng·h/mL to about 300 ng·h/mL, about 300 ng·h/mL to about 400 ng·h/mL, about 300 ng·h/mL to about 350 ng·h/mL, about 400 ng·h/mL to about 500 ng·h/mL, about 350 ng·h/mL to about 400 ng·h/mL, about 450 ng·h/mL to about 500 ng·h/mL, about 130 ng·h/mL to about 160 ng·h/mL, about 405 ng·h/mL to about 450 ng·h/mL, measured over a 24 hour period.

In some embodiments, molecular complex comprising neridronic acid is administered in an amount that results in an AUC of neridronic acid, measured over the entire course of treatment, of about 10,000-30,000 ng·h/mL about 30,000-100,000 ng·h/mL about 30,000-50,000 ng·h/mL, about 30,000-40,000 ng·h/mL, about 40,000-50,000 ng·h/mL, about 50,000-60,000 ng·h/mL, about 60,000-70,000 ng·h/mL, about 50,000-70,000 ng·h/mL, about 70,000-80,000 ng·h/mL, about 80,000-90,000 ng·h/mL, about 90,000-100,000 ng·h/mL, about 70,000-100,000 ng·h/mL, about 100,000-200,0000 ng·h/mL, about 200,000-300,0000 ng·h/mL, about 300,000-400,0000 ng·h/mL, about 400,000-500,0000 ng·h/mL, or any AUC in a range bounded by any of these values.

In some embodiments, an osteoclast inhibitor, a bisphosphonate, or a RANK/RANKL antagonist, such as zoledronic acid, etc., is administered at an interval of about once, twice, or thrice daily, or every 1, 2, 3, 4, 5, 6, 7, 8, 9, 10, 11, 12, 13, or 14 days; or 15, 16, 17, 18, 19, 20, or 21 days; or 22, 23, 24, 25, 26, 27, 28, 29, 30, or 31 days; or 32, 33, 34, 35, 36, 37, 38, 39, 40, 41, 42, 43, 44, or 45; or 46, 47, 48, 49, 50, 51, 52, 53, 54, 55, 56, 57, 58, 59, or 60 days; or 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 days; or 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 days.

Oral administration of zoledronic acid, particularly oral administration of the disodium salt form of zoledronic acid, can result in more sustained plasma levels of the drug as compared to parenteral modes of administration, such intravenous or subcutaneous. For example, the amount of zoledronic acid in the plasma can be significantly higher for oral administration of the disodium salt about 24 hours or 48 hours, or longer, after administration. In some embodiments, oral zoledronic acid has a 24 hour sustained plasma level factor of about 1 or higher, such as about 1 to about 10, about 1 to about 5, about 3 to about 5, or about 3 to about 4. In some embodiments, an orally administered dosage form of zoledronic acid has a 24 hour sustained plasma level factor or a 48 hour sustained plasma level factor that is higher, such as at least 1.2 times, at least about 2 times, at least about 5 times, about 1.2 times to about 20 times, about 2 times to about 15 times, about 5 times to about 10 times, or about 8 to about 15 times that of intravenously administered zoledronic acid. A "sustained plasma level factor," $p_f$, is determined by the equation:

$$p_f = 1000(C_t/C_{max})$$

wherein $C_{max}$ is the maximum plasma concentration of zoledronic acid after it is administered and $C_t$ is the plasma concentration of zoledronic acid at the time of interest, such as 24 hours. For parenteral administration, the $C_{max}$ can be about the $C_0$, or the concentration right after injection of the entire amount of the drug into the body. Sustained plasma level factors can also be obtained for other times, such as 48 hours, by using the plasma concentration of zoledronic acid for $C_t$ in the equation above. For example, if the maximum plasma level of zoledronic acid after administration is 1000 ng/mL and the plasma level of zoledronic acid at 24 hours is 1 ng/mL, the 24 hour sustained plasma level factor is 1.

An oral dosage form comprising zoledronic acid having a dose of zoledronic acid and a configuration suitable for a particular species of mammal may be configured so that the zoledronic acid has a 12 hour sustained plasma level factor of about 12 to about 50, about 20 to about 40, about 25 to about 30, about 30 to about 35, about 35 to about 40, about 33, about 30, about 35, or any 12 hour sustained plasma level factor in a range bounded by, or between, any of these values, for the particular species of mammal.

An oral dosage form comprising zoledronic acid having a dose of zoledronic acid and a configuration suitable for a particular species of mammal may be configured so that the zoledronic acid has a 24 hour sustained plasma level factor of about 10 to about 30, about 10 to about 20, about 10 to about 15, about 12 to about 15 or 16, about 15 to about 20, about 14, about 12, about 15, or any 24 hour sustained plasma level factor in a range bounded by, or between, any of these values, for the particular species of mammal.

An oral dosage form comprising zoledronic acid having a dose of zoledronic acid and a configuration suitable for a particular species of mammal may be configured so that the zoledronic acid has a 36 hour sustained plasma level factor of about 6 to about 20, about 8 to about 15, about 9 to about 12 or 13, about 8 to about 10, about 11 to about 13, about 9, about 13, or any 24 hour sustained plasma level factor in a range bounded by, or between, any of these values, for the particular species of mammal.

An oral dosage form comprising zoledronic acid having a dose of zoledronic acid and a configuration suitable for a particular species of mammal may be configured so that the zoledronic acid has a 48 hour sustained plasma level factor of about 5 to about 20, about 6 to about 15, about 7 or 8 to about 12 or 13, about 8 to about 10, about 11 to about 13, about 8, about 12, or any 48 hour sustained plasma level factor in a range bounded by, or between, any of these values, for the particular species of mammal.

An oral dosage form comprising zoledronic acid having a dose of zoledronic acid and a configuration suitable for a particular species of mammal may be configured so that the zoledronic acid has a 72 hour sustained plasma level factor of about 4 to about 20, about 5 to about 10, about 5 or 6 to about 10 or 11, about 5 to about 6, about 9 to about 10, about 6, about 10, or any 72 hour sustained plasma level factor in a range bounded by, or between, any of these values, for the particular species of mammal.

An oral dosage form comprising zoledronic acid having a dose of zoledronic acid and a configuration suitable for a particular species of mammal may be configured so that the particular species of mammal has a plasma concentration of zoledronic acid at 12 hours that is about 0.5 ng/mL to about 5 ng/mL, about 1 ng/mL to about 3 ng/mL, about 1 ng/mL to about 2 ng/mL, about 2 ng/mL to about 3 ng/mL, about 3 ng/mL to about 4 ng/mL, about 1.2 ng/mL, about 2.6 ng/mL, about 3.2 ng/mL, or any plasma concentration in a range bounded by, or between, any of these values.

An oral dosage form comprising zoledronic acid having a dose of zoledronic acid and a configuration suitable for a particular species of mammal may be configured so that the particular species of mammal has a plasma concentration of zoledronic acid at 24 hours that is about 0.2 ng/mL to about 2 ng/mL, about 0.5 ng/mL to about 1.5 ng/mL, about 0.5 ng/mL to about 1 ng/mL, about 1 ng/mL to about 1.5 ng/mL, about 0.5 ng/mL, about 1.0 ng/mL, about 1.4 ng/mL, or any plasma concentration in a range bounded by, or between, any of these values.

An oral dosage form comprising zoledronic acid having a dose of zoledronic acid and a configuration suitable for a particular species of mammal may be configured so that the particular species of mammal has a plasma concentration of zoledronic acid at 36 hours that is about 0.1 ng/mL to about 2 ng/mL, about 0.2 ng/mL to about 1.5 ng/mL, about 0.2 ng/mL to about 0.5 ng/mL, about 0.5 ng/mL to about 1 ng/mL, about 1 ng/mL to about 1.3 ng/mL, about 0.3 ng/mL, about 0.8 ng/mL, about 1.1 ng/mL, or any plasma concentration in a range bounded by, or between, any of these values.

An oral dosage form comprising zoledronic acid having a dose of zoledronic acid and a configuration suitable for a particular species of mammal may be configured so that the particular species of mammal has a plasma concentration of zoledronic acid at 48 hours that is about 0.1 ng/mL to about 2 ng/mL, about 0.2 ng/mL to about 1.5 ng/mL, about 0.2 ng/mL to about 0.5 ng/mL, about 0.5 ng/mL to about 0.9 ng/mL, about 0.9 ng/mL to about 1.3 ng/mL, about 0.3 ng/mL, about 0.7 ng/mL, about 1.1 ng/mL, or any plasma concentration in a range bounded by, or between, any of these values.

An oral dosage form comprising zoledronic acid having a dose of zoledronic acid and a configuration suitable for a particular species of mammal may be configured so that the particular species of mammal has a plasma concentration of zoledronic acid at 72 hours that is about 0.2 ng/mL to about 1 ng/mL, about 0.2 ng/mL to about 1.5 ng/mL, about 0.1 ng/mL to about 0.3 ng/mL, about 0.3 ng/mL to about 0.6 ng/mL, about 0.6 ng/mL to about 1 ng/mL, about 0.2 ng/mL, about 0.5 ng/mL, about 0.9 ng/mL, or any plasma concentration in a range bounded by, or between, any of these values.

An oral dosage form comprising zoledronic acid having a dose of zoledronic acid and a configuration suitable for a particular species of mammal may be configured so that the elimination half-life of zoledronic acid in the particular species of mammal is about 30 hours to about 100 hours, about 40 hours to about 60 hours, about 40 hours to about 50 hours, about 50 hours to about 60 hours, about 42 hours, about 51 hours, about 59 hours, or any half-life in a range bounded by, or between, any of these values.

As used herein, the "elimination half-life" refers to the apparent first-order terminal plasma elimination half-life, obtained by non-compartmental analysis using Win-Nonlin. A terminal plasma elimination half-life is the time required to reduce the plasma concentration to half after reaching pseudo-equilibrium, and not the time required to eliminate half the administered dose. For orally administered drugs, terminal plasma elimination half-life can be affected by absorption of the drug, as well as plasma clearance and extent of distribution.

In some embodiments, the disodium salt form of zoledronic acid provides an enhancement to bioavailability, as compared to the diacid form of zoledronic acid, which adds to any enhancement to bioavailability provided by any bioavailability-enhancing agents in the dosage form. In some embodiments, the disodium salt form of zoledronic acid provides an enhancement to bioavailability, as compared to the diacid form of zoledronic acid, which is greater than any enhancement to bioavailability provided by any bioavailability-enhancing agents in the dosage form. In some embodiments, the disodium salt form of zoledronic acid may be administered in a dosage form that is substantially free of bioavailability-enhancing agents.

The C-terminal telopeptide (CTX) is one of the products from type I collagen degradation by osteoclasts during bone resorption. Thus, CTX serum levels may be used as a biomarker to indicate and monitor bone breakdown, resorption, and loss. In some embodiments, zoledronic acid and other bisphosphonates may be used to inhibit osteoclast activity and/or lower CTX serum levels, for example, by at least about 5%, at least about 10%, at least about 15%, at least about 20%, at least about 25%, at least about 30%, at least about 35%, at least about 40%, at least about 45%, at least about 50%, at least about 55%, at least about 60%, at least about 70%, at least about 75%, at least about 80%, at least about 85%, at least about 90%, at least about 95%, at least about 99%, at least about 100%, about 60%-70%, about 70%-80%, about 80%-90%, about 85-95%, about 80%-85%, about 85%-90%, about 90%-95%, or any other reduction in osteoclast activity or CTX serum levels in a range bounded by, or between, any of these values.

In some embodiments, zoledronic acid in a disodium salt or an acid form and other bisphosphonates including salt or acid form may be used to treat Paget's disease of Bone or treat pain associated with Paget's disease of bone and/or lower serum alkaline phosphatase (ALP) levels. For example, the reduction of ALP levels by at least about 20%, at least about 40%, at least about 50%, at least about 60%, at least about 80%, about 50-60%, about 60-80%, about 80-90%, about 90-95%, or any other reduction in ALP levels in a range bounded by, or between, any of these values from baseline, within 12 months, 18 months, or up to at least 5 years from the time of the last oral administration of zoledronic acid or other bisphosphonates. In some embodiments, when zoledronic acid in a disodium salt or an acid form, or other bisphosphonate is administered to treat the Paget's disease of bone or pain associated with the Paget's disease of bone, the Paget's disease or the pain associated with the Paget's disease has recurrence rate of less than 20%, less than 10%, less than 5%, less than 1%, or does not return within 12 months, 18 months, or 5 years, or more, from the time of the last oral administration of zoledronic acid, or other bisphosphonates.

In some embodiments, a dosage form comprising a disodium salt of zoledronic acid is a solid.

In some embodiments, a dosage form comprising a disodium salt of zoledronic acid is used to treat an inflammatory condition.

In some embodiments, a dosage form comprising a disodium salt of zoledronic acid is used to treat arthritis.

In some embodiments, a dosage form comprising a disodium salt of zoledronic acid is used to treat complex regional pain syndrome.

In some embodiments, zoledronic acid is in a form that has an aqueous solubility, meaning the solubility in water, greater than 1% (w/v), about 5% (w/v) to about 50% (w/v), about 5% (w/v) to about 20% (w/v), about 10% (w/v) to about 15% (w/v), or about 12% (w/v) to about 13% (w/v).

The disodium salt form of zoledronic acid can be more compressible than the diacid form of zoledronic acid. This can make it easier for a dosage form to have a desired hardness. It can also make it easier to increase the drug load, so that a smaller tablet can be given for a given dosage strength. In some embodiments, a solid dosage form of zoledronic acid, such as the diacid form of zoledronic acid or the disodium salt form of zoledronic acid, can have a hardness of about 5 kPa to about 20 kPa or about 5 kPa to about 14 kPa.

Zoledronic acid or another bisphosphonate may be combined with a pharmaceutical carrier selected on the basis of the chosen route of administration and standard pharmaceutical practice as described, for example, in Remington's Pharmaceutical Sciences, 2005, the disclosure of which is hereby incorporated herein by reference, in its entirety. The relative proportions of active ingredient and carrier may be determined, for example, by the solubility and chemical nature of the compounds, chosen route of administration and standard pharmaceutical practice.

Zoledronic acid or another bisphosphonate may be administered by any means that may result in the contact of the active agent(s) with the desired site or site(s) of action in the body of a patient. The compounds may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients.

In some embodiments, an osteoclast inhibitor is co-administered with a steroid. Suitable steroids include, for example, hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, acleometasone dipropionate, betamethasone valerate, betamethasone dippropionate, prednicarbate, clobetasone-17-butyrate, clobetasol-17-propionate, fluocortilone caproate, fluocortolone pivalate, and fluprednidene acetate, hydrocortisone-17-butyrate, 17-aceponate, 17-buteprate, and prednicarbate.

Any effective dose of steroid can be administered to a person. In some embodiment, the dose of a steroid may be about 1-500 mg, 5-25 mg, about 1-3 mg, about 2-4 mg, about 3-5 mg, about 4-6 mg, about 5-7 mg, about 6-8 mg, about 7-9 mg, about 8-10 mg, about 10-15 mg, about 10-20 mg, about 20-50 mg, about 50-100 mg, about 100-200 mg, about 200-300 mg, about 300-400 mg, 400-500 mg 1-20 mg, about 10-30 mg, about 20-40 mg, about 30-50 mg, about 40-60 mg, about 50-70 mg, about 60-80 mg, about 70-90 mg, about 80-100 mg, about 90-110 mg, about 100-120 mg, about 110-130 mg, about 120-140 mg, about 130-150 mg, about 140-160 mg, about 150-170 mg, about 160-180 mg, about 170-190 mg, about 180-200 mg, about 190-210 mg, about 200-220 mg, about 210-230 mg, about 220-240 mg, about 230-250 mg, about 240-260 mg, about 250-270 mg, about 260-280 mg, about 270-290 mg, about 280-300 mg, about 290-310 mg, about 300-320 mg, about 310-330 mg, about 320-340 mg, about 330-350 mg, about 340-360 mg, about 350-370 mg, about 360-380 mg, about 370-390 mg, about 380-300 mg, about 390-410 mg, about 400-420 mg, about 410-430 mg, about 420-440 mg, about 430-450 mg, about 440-460 mg, about 450-470 mg, about 460-480 mg, about 470-490 mg, about 480-300 mg, about 490-510 mg of the steroid, or any amount in a range bounded by any of these values.

The steroid can be given orally (for example, 7.5 mg of prednisone), by a separate infusion (for example, 7.5 mg of methyl prednisolone), mixed in with zoledronic acid in the same infusion, or be administered intramuscularly, subcutaneously, by rectal suppository, by inhalation, or injected directly into a joint.

Zoledronic acid or another bisphosphonate may be administered to a human patient in a variety of forms adapted to the chosen route of administration, e.g., orally, rectally, or parenterally. Parenteral administration in this respect includes, but is not limited to, administration by the following routes: pulmonary, intrathecal, intravenous, intramuscular, subcutaneous, intraocular, intrasynovial, transepithelial including transdermal, sublingual and buccal; topically; nasal inhalation via insufflation; and rectal systemic.

The effective amount of zoledronic acid or another bisphosphonate will vary depending on various factors known to the treating physicians, such as the severity of the condition to be treated, route of administration, formulation and dosage forms, physical characteristics of the bisphosphonate compound used, and age, weight and response of the individual patients.

In some embodiments, the daily oral dose of pamidronate is about 10 mg to about 1,000 mg, about 50 mg to about 500 mg, about 100 mg to about 500 mg, or about 150 mg to about 300 mg. In some embodiments, the parenteral dose of pamidronate is about 5 mg to about 500 mg, about 5 mg to about 200 mg, or about 10 mg to about 150 mg.

In some embodiments, the daily oral dose of neridronate is about 10 mg to about 1,000 mg, about 50 mg to about 500 mg, about 100 mg to about 500 mg, or about 150 mg to about 300 mg. In some embodiments, the parenteral dose of neridronate is about 5 mg to about 500 mg, about 5 mg to about 200 mg, or about 10 mg to about 150 mg.

In some embodiments, the daily oral dose of alendronate is about 0.5 mg to about 200 mg, about 1 mg to about 100 mg, about 5 mg to about 100 mg, or about 2 mg to about 50 mg. In some embodiments, the parenteral dose of alendronate is about 1 mg to about 100 mg, about 1 mg to about 40 mg, or about 2 mg to about 30 mg.

In some embodiments, the daily oral dose of olpadronate is about 0.5 mg to about 200 mg, about 1 mg to about 100 mg, about 5 mg to about 100 mg, or about 2 mg to about 50 mg. In some embodiments, the parenteral dose of olpadronate is about 1 mg to about 100 mg, about 1 mg to about 40 mg, or about 2 mg to about 30 mg.

In some embodiments, the daily oral dose of ibandronate is about 0.25 mg to about 100 mg, about 0.5 mg to about 50 mg, about 2.5 mg to about 50 mg, or about 1 mg to about 25 mg. In some embodiments, the parenteral dose of ibandronate is about 0.5 mg to about 50 mg, about 0.5 mg to about 20 mg, or about 1 mg to about 15 mg.

In some embodiments, the daily oral dose of risedronate is about 0.25 mg to about 100 mg, about 0.5 mg to about 50 mg, about 2.5 mg to about 50 mg, or about 1 mg to about 25 mg. In some embodiments, the parenteral dose of risedronate is about 0.25 mg to about 25 mg, about 0.25 mg to about 10 mg, or about 0.5 mg to about 7.5 mg.

In some embodiments, the daily oral dose of zoledronate is about 0.005 mg to about 20 mg, about 0.1 mg to about 10 mg, about 0.5 mg to about 10 mg, or about 0.2 mg to about 5 mg. In some embodiments, the parenteral dose of zoledronate is about 0.25 mg to about 25 mg, about 0.25 mg to about 10 mg, or about 0.5 mg to about 7.5 mg.

The dose of pamidronate, neridronate, olpadronate, alendronate, ibandronate, risedronate, zoledronate or another bisphosphonate compound may be administered in a single or divided dose.

The amount of zoledronic acid or another bisphosphonate in a therapeutic composition may vary. For example, some liquid compositions may comprise about 0.0001% (w/v) to about 50% (w/v), about 0.01% (w/v) to about 20% (w/v), about 0.01% to about 10% (w/v), about 0.001% (w/v) to about 1% (w/v), about 0.1% (w/v) to about 0.5% (w/v), about 1% (w/v) to about 3% (w/v), about 3% (w/v) to about 5% (w/v), about 5% (w/v) to about 7% (w/v), about 7% (w/v) to about 10% (w/v), about 10% (w/v) to about 15% (w/v), about 15% (w/v) to about 20% (w/v), about 20% (w/v) to about 30% (w/v), about 30% (w/v) to about 40% (w/v), or about 40% (w/v) to about 50% (w/v) of zoledronic acid.

Some solid compositions may comprise at least about 5% (w/w), at least about 10% (w/w), at least about 20% (w/w), at least about 50% (w/w), at least about 70% (w/w), at least about 80%, about 10% (w/w) to about 30% (w/w), about 10% (w/w) to about 20% (w/w), about 20% (w/w) to about 30% (w/w), about 30% (w/w) to about 50% (w/w), about 30% (w/w) to about 40% (w/w), about 40% (w/w) to about 50% (w/w), about 50% (w/w) to about 80% (w/w), about 50% (w/w) to about 60% (w/w), about 70% (w/w) to about 75% (w/w), about 70% (w/w) to about 80% (w/w), or about 80% (w/w) to about 90% (w/w) of zoledronic acid.

Any suitable amount of an osteoclast inhibitor, including a bisphosphonate, such as a nitrogen-containing bisphosphonate, e.g. zoledronic acid, minodronic acid, or ibandronic acid, may be used. Some solid or liquid oral dosage forms, or units of oral dosage forms (referred to collectively herein as "oral dosage form(s)") may contain about 0.005 mg to about 20 mg, about 0.1 mg to about 10 mg, about 0.5 mg to about 10 mg, about 0.2 mg to about 5 mg, about 1 mg to about 500 mg, about 1 mg to about 50 mg, about 10 mg to about 250 mg, about 100 mg to about 300 mg, about 20 mg to about 200 mg, about 20 mg to about 150 mg, about 30 mg to about 100 mg, about 50 mg to about 200 mg, about 1 mg to about 1,000 mg, about 10 mg to about 50 mg, about 40 mg to about 60 mg, about 50 mg to about 60 mg, about 55 mg, about 10 mg to about 300 mg, about 10 mg to about 150 mg, about 10 mg to about 100 mg, about 40 mg to about 150 mg, about 10 mg to about 600 mg, about 40 mg to about 600 mg, about 40 mg to about 2000 mg, about 40 mg to about 800 mg, about 25 mg to about 800 mg, about 30 mg to about 800 mg, about 10 mg to about 500 mg, about 50 mg to about 150 mg, about 50 mg, about 100 mg, about 50 mg to about 500 mg, about 150 mg to about 200 mg, about 100 mg to about 2000 mg, about 300 mg to about 1500 mg, about 200 mg to about 1000 mg, about 100 mg to about 500 mg, about 160 mg, or about 150 mg of zoledronic acid in an acid form or in a salt form such as disodium salt form, or any amount of osteoclast inhibitor in a range bounded by, or between, any of these values. In some embodiments, the oral osteoclast inhibitor is administered daily, weekly, biweekly, monthly, every two or three months, once a year, or twice a year.

Some oral dosage forms may contain about 0.005 mg to about 20 mg, about 0.1 mg to about 10 mg, about 0.5 mg to about 10 mg, about 0.2 mg to about 5 mg, about 1 mg to about 500 mg, about 1 mg to about 50 mg, about 10 mg to about 250 mg, about 100 mg to about 300 mg, about 20 mg to about 200 mg, about 20 mg to about 150 mg, about 30 mg to about 100 mg, about 1 mg to about 1,000 mg, about 10 mg to about 50 mg, about 40 mg to about 60 mg, about 50 mg to about 60 mg, about 55 mg, about 10 mg to about 300 mg, about 10 mg to about 150 mg, about 10 mg to about 100 mg, about 40 mg to about 150 mg, about 10 mg to about 600 mg, about 40 mg to about 600 mg, about 40 mg to about 2000 mg, about 40 mg to about 800 mg, about 25 mg to about 800 mg, about 30 mg to about 800 mg, about 10 mg to about 500 mg, about 50 mg to about 200 mg, about 50 mg, about 100 mg, about 50 mg to about 500 mg, about 150 mg to about 200 mg, about 100 mg to about 2000 mg, about 300 mg to about 1500 mg, about 200 mg to about 1000 mg, about 100 mg to about 500 mg, about 160 mg, or about 150 mg of osteoclast inhibitor, or any amount of osteoclast inhibitor in a range bounded by, or between, any of these values. In some embodiments, the oral osteoclast inhibitor is administered daily, weekly, bi-weekly, monthly, every two or three months, once a year, or twice a year.

Any suitable amount of an osteoclast inhibitor, including a bisphosphonate, such as a nitrogen-containing bisphosphonate, e.g. zoledronic acid, neridronate (neridronic acid), pamidronate, olpadronate, alendronate, risedronate, minodronic acid, or ibandronic acid, may be used. Some solid or liquid dosage forms, or units of dosage forms may contain about 0.005 mg to about 20 mg, about 0.1 mg to about 10 mg, about 0.5 mg to about 10 mg, about 0.2 mg to about 5 mg, about 1 mg to about 500 mg, about 1 mg to about 50 mg, about 10 mg to about 250 mg, about 100 mg to about 300 mg, about 20 mg to about 200 mg, about 20 mg to about 150 mg, about 30 mg to about 100 mg, about 50 mg to about 200 mg, about 1 mg to about 1,000 mg, about 10 mg to about 50 mg, about 40 mg to about 60 mg, about 50 mg to about 60 mg, about 55 mg, about 10 mg to about 300 mg, about 10 mg to about 150 mg, about 10 mg to about 100 mg, about 40 mg to about 150 mg, about 10 mg to about 600 mg, about 40 mg to about 600 mg, about 40 mg to about 2000 mg, about 40 mg to about 800 mg, about 25 mg to about 800 mg, about 30 mg to about 800 mg, about 10 mg to about 500 mg, about 50 mg to about 150 mg, about 50 mg, about 100 mg, about 50 mg to about 500 mg, about 150 mg to about 200 mg, about 100 mg to about 2000 mg, about 300 mg to about 1500 mg, about 200 mg to about 1000 mg, about 100 mg to about 500 mg, about 160 mg, or about 150 mg of zoledronic acid in an acid form or in a salt form such as disodium salt form, or any amount of osteoclast inhibitor in a range bounded by, or between, any of these values. In some embodiments, the oral or IV osteoclast inhibitor is administered daily, every other day, every third day, weekly, biweekly, monthly, every two or three months, every six months, once a year, or twice a year from day 1.

Some dosage forms may contain about 0.005 mg to about 20 mg, about 0.1 mg to about 10 mg, about 0.5 mg to about 10 mg, about 0.2 mg to about 5 mg, about 1 mg to about 500 mg, about 1 mg to about 50 mg, about 10 mg to about 250 mg, about 100 mg to about 300 mg, about 20 mg to about 200 mg, about 20 mg to about 150 mg, about 30 mg to about 100 mg, about 1 mg to about 1,000 mg, about 10 mg to about 50 mg, about 40 mg to about 60 mg, about 50 mg to about 65 mg, about 65 mg to about 70 mg, about 50 mg to about 60 mg, about 55 mg, about 10 mg to about 300 mg, about 10 mg to about 150 mg, about 10 mg to about 100 mg, about 40 mg to about 150 mg, about 10 mg to about 600 mg, about 40 mg to about 600 mg, about 100 mg to about 600 mg, about 40 mg to about 2000 mg, about 40 mg to about 800 mg, about 25 mg to about 800 mg, about 30 mg to about 800 mg, about 10 mg to about 500 mg, about 50 mg to about 150 mg, about 50 mg, about 100 mg, about 50 mg to about 200 mg, about 50 mg to about 500 mg, about 150 mg to about 200 mg, about 100 mg to about 2000 mg, about 300 mg to about 1500 mg, about 200 mg to about 1000 mg, about 100 mg to about 500 mg, about 160 mg, or about 150 mg of osteoclast inhibitor, or any amount of osteoclast inhibitor in a range bounded by, or between, any of these values. In some embodiments, the oral or IV osteoclast inhibitor is administered daily, every other day, every third day, weekly, bi-weekly, monthly, every two or three months, every 6 months, once a year, or twice a year from day 1.

In some embodiments, an oral dosage form may contain about 10 mg/m$^2$ to about 20 mg/m$^2$, about 15 mg/m$^2$ to about 20 mg/m$^2$, about 18 mg/m$^2$, about 80 mg/m$^2$ to about 150 mg/m$^2$, about 90 mg/m$^2$ to about 150 mg/m$^2$, about 100 mg/m$^2$ to about 150 mg/m$^2$ of zoledronic acid, or any amount of zoledronic in a range bounded by, or between, any of these values. All dosage ranges or amounts expressed in mg/m$^2$ are based upon the body surface area of the mammal.

In some embodiments, the daily oral dose of an osteoclast inhibitor, including a bisphosphonate, such as a nitrogen-containing bisphosphonate, e.g. zoledronic acid, minodronic acid, or ibandronic acid, is about 0.005 mg to about 20 mg, about 0.1 mg to about 10 mg, about 0.5 mg to about 10 mg, about 0.2 mg to about 5 mg, or any amount in a range bounded by, or between, any of these values. In some embodiments, the daily oral dose of osteoclast inhibitor is less than about 35 mg/m$^2$, less than about 30 mg/m$^2$, less than about 25 mg/m$^2$, about 1 mg/m$^2$ to about 35 mg/m$^2$, about 1 mg/m$^2$ to about 30 mg/m$^2$, about 1.5 mg/m$^2$ to about 25 mg/m$^2$, about 1.8 mg/m$^2$ to about 20 mg/m$^2$, about 10 mg/m$^2$ to about 20 mg/m$^2$, about 10 mg/m$^2$ to about 30 mg/m$^2$, about 15 mg/m$^2$ to about 20 mg/m$^2$, about 18 mg/m$^2$, or any amount of zoledronic acid in a range bounded by, or between, any of these values.

In some embodiments, the daily oral dose of an osteoclast inhibitor, including a bisphosphonate, such as a nitrogen-containing bisphosphonate, e.g. zoledronic acid, minodronic acid, or ibandronic acid, is about 0.005 mg to about 20 mg, about 0.1 mg to about 10 mg, about 0.5 mg to about 10 mg, about 0.2 mg to about 5 mg, or any amount of osteoclast inhibitor in a range bounded by, or between, any of these values. In some embodiments, the daily oral dose of osteoclast inhibitor is less than about 35 mg/m$^2$, less than about 30 mg/m$^2$, less than about 25 mg/m$^2$, about 1 mg/m$^2$ to about 35 mg/m$^2$, about 1 mg/m$^2$ to about 30 mg/m$^2$, about 1.5 mg/m$^2$ to about 25 mg/m$^2$, about 1.8 mg/m$^2$ to about 20 mg/m$^2$, about 10 mg/m$^2$ to about 20 mg/m$^2$, about 10 mg/m$^2$ to about 30 mg/m$^2$, about 15 mg/m$^2$ to about 20 mg/m$^2$, about 18 mg/m$^2$, or any amount of osteoclast inhibitor in a range bounded by, or between, any of these values.

In some embodiments the daily oral dose of zoledronic acid is about 0.005 mg to about 20 mg, about 0.1 mg to about 10 mg, about 0.5 mg to about 10 mg, about 0.2 mg to about 5 mg, or any amount of zoledronic acid in a range bounded by, or between, any of these values. In some embodiments, the daily oral dose of zoledronic acid is less than about 35 mg/m$^2$, less than about 30 mg/m$^2$, less than about 25 mg/m$^2$, about 1 mg/m$^2$ to about 35 mg/m$^2$, about 1 mg/m$^2$ to about 30 mg/m$^2$, about 1.5 mg/m$^2$ to about 25 mg/m$^2$, about 1.8 mg/m$^2$ to about 20 mg/m$^2$, about 10 mg/m$^2$ to about 20 mg/m$^2$, about 10 mg/m$^2$ to about 30 mg/m$^2$, about 15 mg/m$^2$ to about 20 mg/m$^2$, about 18 mg/m$^2$, or any amount of zoledronic acid in a range bounded by, or between, any of these values.

In some embodiments, the weekly oral dose of the osteoclast inhibitor, including a bisphosphonate, such as a nitrogen-containing bisphosphonate, e.g. zoledronic acid, minodronic acid, ibandronic acid, is about 1 mg to about 1000 mg, about 1 mg to about 500 mg, about 10 mg to about 250 mg, about 100 mg to about 300 mg, about 10 mg to about 100 mg, about 10 mg to about 150 mg, about 10 mg to about 100 mg, about 10 mg to about 300 mg, about 20 mg to about 150 mg, about 20 mg to about 60 mg, about 30 mg to about 70 mg, about 40 mg to about 60 mg, about 50 mg to about 70 mg, about 50 mg, about 55 mg, about 100 mg to about 150 mg, or about 30 mg to about 100 mg. In some embodiments, the weekly oral dose of the osteoclast inhibitor is less than about 250 mg/m$^2$, less than about 200 mg/m$^2$, less than about 175 mg/m$^2$, about 6 mg/m$^2$ to about 250 mg/m$^2$, about 10 mg/m$^2$ to about 210 mg/m$^2$, about 10 mg/m$^2$ to about 170 mg/m$^2$, about 4 mg/m$^2$ to about 140 mg/m$^2$, about 100 mg/m$^2$ to about 140 mg/m$^2$, about 126 mg/m$^2$, or any amount in a range bounded by, or between, any of these values. The weekly oral dose may be given as a single dose, given once during the week, or may be given in 2, 3, 4, 5, 6, or 7 individual doses during the week.

In some embodiments the weekly oral dose of zoledronic acid is about 1 mg to about 1000 mg, about 1 mg to about 500 mg, about 10 mg to about 250 mg, about 100 mg to about 300 mg, about 10 mg to about 100 mg, about 10 mg to about 150 mg, about 10 mg to about 100 mg, about 10 mg to about 300 mg, about 20 mg to about 150 mg, about 20 mg to about 60 mg, about 30 mg to about 70 mg, about 40 mg to about 60 mg, about 50 mg to about 70 mg, about 50 mg, about 55 mg, about 100 mg to about 150 mg, or about 30 mg to about 100 mg. In some embodiments, the weekly oral dose of zoledronic acid is less than about 250 mg/m$^2$, less than about 200 mg/m$^2$, less than about 175 mg/m$^2$, about 6 mg/m$^2$ to about 250 mg/m$^2$, about 10 mg/m$^2$ to about 210 mg/m$^2$, about 10 mg/m$^2$ to about 170 mg/m$^2$, about 4 mg/m$^2$ to about 140 mg/m$^2$, about 100 mg/m$^2$ to about 140 mg/m$^2$, about 126 mg/m$^2$, or any amount of zoledronic acid in a range bounded by, or between, any of these values. The weekly oral dose may be given as a single dose, given once during the week, or may be given in 2, 3, 4, 5, 6, or 7 individual doses during the week.

In some embodiments, the monthly dose of the osteoclast inhibitor, including a bisphosphonate, such as a nitrogen-containing bisphosphonate, e.g. zoledronic acid, minodronic acid, or ibandronic acid, or the amount of the osteoclast inhibitor that is administered over a period of a month, is about 5000 mg or less, about 4000 mg or less, about 3000 mg or less, about 2000 mg or less, about 1000 mg or less, about 700 mg or less, about 600 mg or less, about 1 mg to about 4,000 mg, about 1 mg to about 1,000 mg, about 10 mg to about 1000 mg, about 50 mg to about 1000 mg, about 10 mg to about 600 mg, about 40 mg to about 600 mg, about 50 mg to about 600 mg, about 40 mg to about 400 mg, about 50 mg to about 200 mg, about 200 mg to about 300 mg, about 250 mg to about 350 mg, or about 100 mg to about 600 mg, about 40 mg to about 2000 mg, about 40 mg to about 800 mg, about 50 mg to about 800 mg, or about 100 mg to about 800 mg, about 40 mg to about 1000 mg, about 50 mg to about 1000 mg, or about 100 mg to about 1000 mg, or any monthly dose in a range bounded by, or between, any of these values. In some embodiments, the monthly oral dose of the osteoclast inhibitor is less than about 1000 mg/m$^2$, less than about 800 mg/m$^2$, less than about 600 mg/m$^2$, about 10 mg/m$^2$ to about 1000 mg/m$^2$, about 50 mg/m$^2$ to about 800 mg/m$^2$, about 70 mg/m$^2$ to about 700 mg/m$^2$, about 100 mg/m$^2$ to about 700 mg/m$^2$, about 100 mg/m$^2$ to about 600 mg/m$^2$, about 50 mg/m$^2$ to about 200 mg/m$^2$, about 300 mg/m$^2$ to about 600 mg/m$^2$, about 450 mg/m$^2$ to about 600 mg/m², about 300 mg/m² to about 1000 mg/m², about 400 mg/m² to about 1000 mg/m², about 500 mg/m² to about 1000 mg/m², about 400 mg/m² to about 700 mg/m², about 500 mg/m² to about 600 mg/m², about 540 mg/m², or any amount in a range bounded by, or between, any of these values. A monthly dose may be given as a single dose, or as two or more individual doses administered during the month. In some embodiments, the monthly dose is administered in 2 or 3 weekly doses. In some embodiments, the monthly dose is administered in 4 or 5 weekly doses. In some embodiments, the monthly dose is administered in 28 to 31 daily doses. In some embodiments, the monthly dose is administered in 5 to 10 individual doses during the month. The monthly dose may be administered for only 1 month, or may be repeatedly administered for 2 or more months.

In some embodiments, the monthly dose of zoledronic acid, or the amount of zoledronic acid that is administered over a period of a month, is about 5000 mg or less, about 4000 mg or less, about 3000 mg or less, about 2000 mg or less, about 1000 mg or less, about 700 mg or less, about 600 mg or less, about 1 mg to about 4,000 mg, about 1 mg to about 1,000 mg, about 10 mg to about 1000 mg, about 50 mg to about 1000 mg, about 10 mg to about 600 mg, about 40 mg to about 600 mg, about 50 mg to about 600 mg, about 40 mg to about 400 mg, about 50 mg to about 200 mg, about 200 mg to about 300 mg, about 250 mg to about 350 mg, or about 100 mg to about 600 mg, about 40 mg to about 2000 mg, about 40 mg to about 800 mg, about 50 mg to about 800 mg, or about 100 mg to about 800 mg, about 40 mg to about 1000 mg, about 50 mg to about 1000 mg, or about 100 mg to about 1000 mg, or any monthly dose in a range bounded by, or between, any of these values. In some embodiments, the monthly oral dose of zoledronic acid is less than about 1000 mg/m², less than about 800 mg/m², less than about 600 mg/m², about 10 mg/m² to about 1000 mg/m², about 50 mg/m² to about 800 mg/m², about 70 mg/m² to about 700 mg/m², about 100 mg/m² to about 700 mg/m², about 100 mg/m² to about 600 mg/m², about 50 mg/m² to about 200 mg/m², about 300 mg/m² to about 600 mg/m², about 450 mg/m² to about 600 mg/m², about 300 mg/m² to about 1000 mg/m², about 400 mg/m² to about 1000 mg/m², about 500 mg/m² to about 1000 mg/m², about 400 mg/m² to about 700 mg/m², about 500 mg/m² to about 600 mg/m², about 540 mg/m², or any amount of zoledronic acid in a range bounded by, or between, any of these values. A monthly dose may be given as a single dose, or as two or more individual doses administered during the month. In some embodiments, the monthly dose is administered in 2 or 3 weekly doses. In some embodiments, the monthly dose is administered in 4 or 5 weekly doses. In some embodiments, the monthly dose is administered in 28 to 31 daily doses. In some embodiments, the monthly dose is administered in 5 to 10 individual doses during the month. The monthly dose may be administered for only 1 month, or may be repeatedly administered for 2 or more months.

With respect to orally administering zoledronic acid to a mammal, such as a dog, a rat, a rabbit, a monkey, an ape, or a human being, doses of about 0.03 mg/kg to about 10 mg/kg, or any smaller range within this range, such as about 0.4 mg/kg to about 3 mg/kg, about 0.4 mg/kg to about 1.5 mg/kg, mg/kg, about 0.4 mg/kg to about 0.5 mg/kg, about 0.5 mg/kg to about 0.6 mg/kg, about 0.6 mg/kg to about 0.7 mg/kg, about 0.7 mg/kg to about 0.8 mg/kg, about 0.8 mg/kg to about 0.9 mg/kg, about 0.9 mg/kg to about 1 mg/kg, about 1 mg/kg to about 1.1 mg/kg, about 1.1 mg/kg to about 1.2 mg/kg, about 1.2 mg/kg to about 1.3 mg/kg, about 1.3 mg/kg to about 1.4 mg/kg, about 1.4 mg/kg to about 1.5 mg/kg, about 1.5 mg/kg to about 1.6 mg/kg, about 1.6 mg/kg to about 1.7 mg/kg, about 1.7 mg/kg to about 1.8 mg/kg, about 1.8 mg/kg to about 1.9 mg/kg, about 1.9 mg/kg to about 2 mg/kg, about 2 mg/kg to about 2.1 mg/kg, about 2.1 mg/kg to about 2.2 mg/kg, about 2.2 mg/kg to about 2.3 mg/kg, about 2.3 mg/kg to about 2.4 mg/kg, about 2.4 mg/kg to about 2.5 mg/kg, about 2.5 mg/kg to about 2.6 mg/kg, about 2.6 mg/kg to about 2.7 mg/kg, about 2.7 mg/kg to about 2.8 mg/kg, about 2.8 mg/kg to about 2.9 mg/kg, about 2.9 mg/kg to about 3 mg/kg, about 3 mg/kg to about 3.1 mg/kg, about 3.1 mg/kg to about 3.2 mg/kg, about 3.2 mg/kg to about 3.3 mg/kg, about 3.3 mg/kg to about 3.4 mg/kg, about 3.4 mg/kg to about 3.5 mg/kg, about 3.5 mg/kg to about 3.6 mg/kg, about 3.6 mg/kg to about 3.7 mg/kg, about 3.7 mg/kg to about 3.8 mg/kg, about 3.8 mg/kg to about 3.9 mg/kg, about 3.9 mg/kg to about 4 mg/kg, about 0.4 mg/kg to about 0.6 mg/kg, about 0.6 mg/kg to about 0.8 mg/kg, about 0.8 mg/kg to about 1 mg/kg, about 1 mg/kg to about 1.2 mg/kg, about 1.2 mg/kg to about 1.4 mg/kg, about 1.4 mg/kg to about 1.6 mg/kg, about 1.6 mg/kg to about 1.8 mg/kg, about 1.8 mg/kg to about 2 mg/kg, about 2 mg/kg to about 2.2 mg/kg, about 2.2 mg/kg to about 2.4 mg/kg, about 2.4 mg/kg to about 2.6 mg/kg, about 2.6 mg/kg to about 2.8 mg/kg, about 2.8 mg/kg to about 3 mg/kg, about 3 mg/kg to about 3.2 mg/kg, about 3.2 mg/kg to about 3.4 mg/kg, about 3.4 mg/kg to about 3.6 mg/kg, about 3.6 mg/kg to about 3.8 mg/kg, about 3.8 mg/kg to about 4 mg/kg, about 0.4 mg/kg to about 0.7 mg/kg, about 0.7 mg/kg to about 1 mg/kg, about 1 mg/kg to about 1.3 mg/kg, about 1.3 mg/kg to about 1.6 mg/kg, about 1.6 mg/kg to about 1.9 mg/kg, about 1.9 mg/kg to about 2.2 mg/kg, about 2.2 mg/kg to about 2.5 mg/kg, about 2.5 mg/kg to about 2.8 mg/kg, about 2.8 mg/kg to about 3 mg/kg, about 3.3 mg/kg to about 3.6 mg/kg, about 3.6 mg/kg to about 4 mg/kg, about 0.4 mg/kg to about 1 mg/kg, or about 0.5 mg/kg to about 1 mg/kg, may be a safe dose for repeated oral administration, such as once daily dosing to once yearly dosing, once daily dosing to twice yearly dosing, once daily dosing to thrice yearly dosing, once daily dosing to dosing every three months, once daily dosing to dosing every two months, once daily dosing to dosing every two months, once daily dosing to dosing every month, once daily dosing to dosing every 2-4 weeks, once daily dosing to once weekly dosing, etc.

The doses referred to in the paragraph above for administration of zoledronic acid to a mammal may be safely administered 2, 3, 4, 5, 6, 7, 8, 9, 10, 11, 12, 13, 14, or 15 times, or about 3 to about 10 times, once a day, or less frequently, such as once week, once every two weeks, once a month, etc.

For once daily to once weekly oral administration of zoledronic acid to a mammal such as a mouse, rat, dog, primate, or a human being, in some embodiments, a safely repeated dose may be about 0.03 mg/kg to about 4 mg/kg, or any smaller range within this range, such as about 0.01 mg/kg to about 0.02 mg/kg, about 0.02 mg/kg to about 0.03 mg/kg, about 0.03 mg/kg to about 0.04 mg/kg, about 0.04 mg/kg to about 0.05 mg/kg, about 0.05 mg/kg to about 0.06 mg/kg, about 0.06 mg/kg to about 0.07 mg/kg, about 0.07 mg/kg to about 0.08 mg/kg, about 0.08 mg/kg to about 0.09 mg/kg, about 0.09 mg/kg to about 0.1 mg/kg, about 0.1 mg/kg to about 0.11 mg/kg, about 0.11 mg/kg to about 0.12 mg/kg, about 0.12 mg/kg to about 0.13 mg/kg, about 0.13 mg/kg to about 0.14 mg/kg, about 0.14 mg/kg to about 0.15 mg/kg, about 0.15 mg/kg to about 0.16 mg/kg, about 0.16 mg/kg to about 0.17 mg/kg, about 0.17 mg/kg to about 0.18 mg/kg, about 0.18 mg/kg to about 0.19 mg/kg, about 0.19 mg/kg to about 0.2 mg/kg, about 0.2 mg/kg to about 0.21 mg/kg, about 0.21 mg/kg to about 0.22 mg/kg, about 0.22 mg/kg to about 0.23 mg/kg, about 0.23 mg/kg to about 0.24 mg/kg, about 0.24 mg/kg to about 0.25 mg/kg, about 0.25 mg/kg to about 0.26 mg/kg, about 0.26 mg/kg to about 0.27 mg/kg, about 0.27 mg/kg to about 0.28 mg/kg, about 0.28 mg/kg to about 0.29 mg/kg, about 0.29 mg/kg to about 0.3 mg/kg, about 0.3 mg/kg to about 0.31 mg/kg, about 0.31 mg/kg to about 0.32 mg/kg, about 0.32 mg/kg to about 0.33 mg/kg, about 0.33 mg/kg to about 0.34 mg/kg, about 0.34 mg/kg to about 0.35 mg/kg, about 0.35 mg/kg to about 0.36 mg/kg, about 0.36 mg/kg to about 0.37 mg/kg, about 0.37 mg/kg to about 0.38 mg/kg, about 0.38 mg/kg to about 0.39 mg/kg, about 0.39 mg/kg to about 0.4 mg/kg, about 0.05 mg/kg to about 0.2 mg/kg, about 0.05 mg/kg to about 0.15 mg/kg, about 0.06 mg/kg to about 0.15 mg/kg, about 0.07 mg/kg to about 0.15 mg/kg, about 0.08 mg/kg to about 0.15 mg/kg, about 0.09 mg/kg to about 0.15 mg/kg, about 0.1 mg/kg to about 0.15 mg/kg, about 0.03 mg/kg to about 0.5 mg/kg, about 0.06 mg/kg to about 0.2 mg/kg, about 0.07 mg/kg to about 0.2 mg/kg, about 0.08 mg/kg to about 0.2 mg/kg, about 0.09 mg/kg to about 0.2 mg/kg, about 0.1 mg/kg to about 0.2 mg/kg, about 0.4 mg to about 4 mg, about 0.4 mg/kg to about 0.6 mg/kg, about 0.6 mg/kg to about 0.8 mg/kg, about 0.8 mg/kg to about 1 mg/kg, about 1 mg/kg to about 1.2 mg/kg, about 1.2 mg/kg to about 1.4 mg/kg, about 1.4 mg/kg to about 1.6 mg/kg, about 1.6 mg/kg to about 1.8 mg/kg, about 1.8 mg/kg to about 2 mg/kg, about 2 mg/kg to about 2.2 mg/kg, about 2.2 mg/kg to about 2.4 mg/kg, about 2.4 mg/kg to about 2.6 mg/kg, about 2.6 mg/kg to about 2.8 mg/kg, about 2.8 mg/kg to about 3 mg/kg, about 3 mg/kg to about 3.2 mg/kg, about 3.2 mg/kg to about 3.4 mg/kg, about 3.4 mg/kg to about 3.6 mg/kg, about 3.6 mg/kg to about 3.8 mg/kg, about 3.8 mg/kg to about 4 mg/kg, about 0.5 mg/kg to about 2 mg/kg, about 0.6 mg/kg to about 2 mg/kg, about 0.7 mg/kg to about 2 mg/kg, about 0.8 mg/kg to about 2 mg/kg, about 0.5 mg/kg to about 1.5 mg/kg, about 0.6 mg/kg to about 1.5 mg/kg, about 0.7 mg/kg to about 1.5 mg/kg, about 0.8 mg/kg to about 1.5 mg/kg, about 0.5 mg/kg to about 0.9 mg/kg, about 0.6 mg/kg to about 0.9 mg/kg, about 0.7 mg/kg to about 0.9 mg/kg, about 0.5 mg/kg to about 1 mg/kg, about 0.6 mg/kg to about 1 mg/kg, about 0.7 mg/kg to about 1 mg/kg, about 0.8 mg/kg to about 1 mg/kg, or about 0.8 mg/kg to about 0.9 mg/kg.

For once weekly or less frequent oral administration of zoledronic acid to a mammal such as a mouse, rat, dog, primate, or a human being, in some embodiments, a safely repeated dose may be about 0.4 mg to about 10 mg, or any smaller range within this range, such as about 0.4 mg/kg to about 0.6 mg/kg, about 0.6 mg/kg to about 0.8 mg/kg, about 0.8 mg/kg to about 1 mg/kg, about 1 mg/kg to about 1.2 mg/kg, about 1.2 mg/kg to about 1.4 mg/kg, about 1.4 mg/kg to about 1.6 mg/kg, about 1.6 mg/kg to about 1.8 mg/kg, about 1.8 mg/kg to about 2 mg/kg, about 2 mg/kg to about 2.2 mg/kg, about 2.2 mg/kg to about 2.4 mg/kg, about 2.4 mg/kg to about 2.6 mg/kg, about 2.6 mg/kg to about 2.8 mg/kg, about 2.8 mg/kg to about 3 mg/kg, about 3 mg/kg to about 3.2 mg/kg, about 3.2 mg/kg to about 3.4 mg/kg, about 3.4 mg/kg to about 3.6 mg/kg, about 3.6 mg/kg to about 3.8 mg/kg, about 3.8 mg/kg to about 4 mg/kg, about 4 mg/kg to about 4.2 mg/kg, about 4.2 mg/kg to about 4.4 mg/kg, about 4.4 mg/kg to about 4.6 mg/kg, about 4.6 mg/kg to about 4.8 mg/kg, about 4.8 mg/kg to about 5 mg/kg, about 5 mg/kg to about 5.2 mg/kg, about 5.2 mg/kg to about 5.4 mg/kg, about 5.4 mg/kg to about 5.6 mg/kg, about 5.6 mg/kg to about 5.8 mg/kg, about 5.8 mg/kg to about 6 mg/kg, about 6 mg/kg to about 6.2 mg/kg, about 6.2 mg/kg to about 6.4 mg/kg, about 6.4 mg/kg to about 6.6 mg/kg, about 6.6 mg/kg to about 6.8 mg/kg, about 6.8 mg/kg to about 7 mg/kg, about 7 mg/kg to about 7.2 mg/kg, about 7.2 mg/kg to about 7.4 mg/kg, about 7.4 mg/kg to about 7.6 mg/kg, about 7.6 mg/kg to about 7.8 mg/kg, about 7.8 mg/kg to about 8 mg/kg, about 8 mg/kg to about 8.2 mg/kg, about 8.2 mg/kg to about 8.4 mg/kg, about 8.4 mg/kg to about 8.6 mg/kg, about 8.6 mg/kg to about 8.8 mg/kg, about 8.8 mg/kg to about 9 mg/kg, about 9 mg/kg to about 9.2 mg/kg, about 9.2 mg/kg to about 9.4 mg/kg, about 9.4 mg/kg to about 9.6 mg/kg, about 9.6 mg/kg to about 9.8 mg/kg, about 9.8 mg/kg to about 10 mg/kg, about 0.5 mg/kg to about 2 mg/kg, about 0.6 mg/kg to about 2 mg/kg, about 0.7 mg/kg to about 2 mg/kg, about 0.8 mg/kg to about 2 mg/kg, about 0.5 mg/kg to about 1.5 mg/kg, about 0.6 mg/kg to about 1.5 mg/kg, about 0.7 mg/kg to about 1.5 mg/kg, about 0.8 mg/kg to about 1.5 mg/kg, about 0.5 mg/kg to about 1 mg/kg, about 0.6 mg/kg to about 1 mg/kg, about 0.7 mg/kg to about 1 mg/kg, about 0.8 mg/kg to about 1 mg/kg, or about 0.8 mg/kg to about 0.9 mg/kg, In some embodiments, the osteoclast inhibitor comprises zoledronic acid, and the oral zoledronic acid, or disodium salt thereof, may be administered in combination with about 0.1 mg to about 10 mg of zoledronic acid, or a salt thereof, administered parenterally, such as intravenously. In some embodiments, about 50 mg, about 100 mg, or about 150 mg of the disodium salt of zoledronic acid is administered orally in combination with 1 mg parenteral, such as intravenous, zoledronic acid. In some embodiments the parenteral dose of zoledronic acid is about 0.25 mg to about 25 mg, about 0.25 mg to about 10 mg, or about 0.5 mg to about 7.5 mg.

With respect to oral administration of an osteoclast inhibitor, such as zoledronic acid, minodronic acid, ibandronic acid, or another bisphosphonate, for the treatment of pain associated with inflammation, arthritis, CRPS, or any other condition recited herein, it may helpful if the mammal or human being to which the osteoclast inhibitor is administered does not eat food or drink beverage, (other than any water required to swallow the oral dosage form) for at least about 1 hour, at least about 2 hours, at least about 4 hours, at least about 6 hours, at least about 8 hours, at least about 10 hours, or at least about 12 hours before the osteoclast inhibitor is administered. It may also be helpful if the mammal or human being to which the osteoclast inhibitor is administered does not eat food or drink beverage for at least about 30 minutes, at least about 1 hour, at least about 2 hours, at least about 3 hours, or at least about 4 hours after the osteoclast inhibitor is administered. In some embodiments, a human being to which the zoledronic acid is administered avoids lying down, or remains upright or sits upright, for at least about 30 minutes or about 1 hour after receiving a dosage form containing the osteoclast inhibitor. Avoiding food or beverage before or after oral administration of the osteoclast inhibitor can improve the bioavailability of the osteoclast inhibitor.

The oral bioavailability of osteoclast inhibitor in a dosage form can vary. Some dosage forms may have ingredients added to enhance the bioavailability. However, bioavailability enhancement is not necessary for an oral dosage form to be effective. In some embodiments, the dosage form is substantially free of bioavailability-enhancing agents, such as amino acids or large quantities (e.g. at least about 5%, 10%, 20%, 50%, 70%, or more) of carboxylic acid salts. In some embodiments, an oral dosage form may have an oral bioavailability of the osteoclast inhibitor—such as zoledronic acid, minodronic acid, ibandronic acid—of about 0.01% to about 10%, about 0.1% to about 7%, about 0.1% to about 5%, etc. Without ingredients or other methods to enhance bioavailability, bisphosphonates such as zoledronic acid typically have a low bioavailability in an oral dosage form. In some embodiments, the oral bioavailability of zoledronic acid is unenhanced or substantially unenhanced. For example, the oral bioavailability of zoledronic acid can be about 0.01% to about 5%, about 0.01% to about 4%, about 0.1% to about 3%, about 0.1% to about 2%, about 0.2% to about 2%, about 0.2% to about 1.5%, about 0.3% to about 1.5%, about 0.3% to about 1%, about 1% to about 3%, about 1.2% to about 3.5%, about 1.2% to about 3%, about 1% to about 4%, about 1.5% to about 4.5%, about 0.1% to about 0.5%, about 0.3% to about 0.5%, about 0.5% to about 1%, about 0.6% to about 0.7%, about 0.7% to about 0.8%, about 0.8% to about 0.9%, about 0.9% to about 1% to about 1.1%, about 1.1% to about 1.2%, about 1.2% to about 1.3%, about 1.3% to about 1.4%, about 1.4% to about 1.5%, about 1.5% to about 1.6%, about 1.6% to about 1.8%, about 1.8% to about 2%, about 2% to about 2.2%, about 2.2% to about 2.4%, about 2.4% to about 2.6%, about 2.6% to about 2.8%, about 2.8% to about 3.0%, about 3% to about 3.2%, about 3.2% to about 3.4%, about 3.4% to about 3.6%, about 3.6% to about 3.8%, about 3.8% to about 4%, about 2% to about 2.5%, or any bioavailability of zoledronic acid in a range bounded by, or between, any of these values.

One embodiment is a pharmaceutical composition comprising an osteoclast inhibitor such as zoledronic acid, minodronic acid, or ibandronic acid wherein the oral bioavailability of zoledronic acid in the dosage form is from about 0.01% to about 10%.

In some embodiments, the oral bioavailability of the osteoclast inhibitor in the dosage form is about 0.01% to about 5%, about 0.1% to about 7%, about 0.1% to about 5%, about 0.1% to about 3%, about 0.1% to about 2%, about 0.2% to about 2%, about 0.2% to about 1.5%, about 0.3% to about 1.5%, or about 0.3% to about 1.0%.

In some embodiments, the oral bioavailability of zoledronic acid in the dosage form is about 0.01% to about 5%.

In some embodiments, the oral bioavailability of zoledronic acid in the dosage form is about 0.1% to about 7%.

In some embodiments, the oral bioavailability of zoledronic acid in the dosage form is about 0.1% to about 5%.

In some embodiments, the oral bioavailability of zoledronic acid in the dosage form is about 0.1% to about 3%.

In some embodiments, the oral bioavailability of zoledronic acid in the dosage form is about 0.1% to about 2%.

In some embodiments, the oral bioavailability of zoledronic acid in the dosage form is about 0.2% to about 2%.

In some embodiments, the oral bioavailability of zoledronic acid in the dosage form is about 0.2% to about 1.5%.

In some embodiments, the oral bioavailability of zoledronic acid in the dosage form is about 0.3% to about 1.5%.

In some embodiments, the oral bioavailability of zoledronic acid in the dosage form is about 0.3% to about 1.0%.

In some embodiments, an oral dosage form comprises about 10 mg to about 300 mg of zoledronic acid, minodronic acid, or ibandronic acid and is administered daily for about 2 to about 15 consecutive days. This regimen may be repeated once monthly, once every two months, once every three months, once every four months, once every five months, once every six months, once yearly, or once every two years.

In some embodiments, an oral dosage form comprises about 10 mg to about 150 mg or about 10 mg to about 100 mg of zoledronic acid, minodronic acid, or ibandronic acid and is administered daily for about 2 to about 15 consecutive days. This regimen may be repeated once monthly, once every two months, once every three months, once every four months, once every five months, once every six months, once yearly, or once every two years.

In some embodiments, an oral dosage form comprises about 10 mg to about 150 mg or about 10 mg to about 100 mg of zoledronic acid, minodronic acid, or ibandronic acid and is administered daily for about 5 to about 10 consecutive days. This regimen may be repeated once monthly, once every two months, once every three months, once every four months, once every five months, once every six months, once yearly, or once every two years.

In some embodiments, an oral dosage form comprises about 40 mg to about 150 mg of zoledronic acid, minodronic acid, or ibandronic acid and is administered daily for about 5 to about 10 consecutive days. This regimen may be repeated once monthly, once every two months, once every three months, once every four months, once every five months, once every six months, once yearly, or once every two years.

In some embodiments, the oral zoledronic acid, minodronic acid, or ibandronic acid may be administered as one dose of about 100 mg to about 2000 mg. In some embodiments, the oral zoledronic acid, minodronic acid, or ibandronic acid may be administered as one dose of about 300 mg to about 1500 mg. In some embodiments, the oral zoledronic acid, minodronic acid, or ibandronic acid may be administered as one dose of about 200 mg to about 1000 mg. The dose of zoledronic acid, minodronic acid, or ibandronic acid may be administered in a single or divided dose.

An osteoclast inhibitor, such as zoledronic acid, minodronic acid, or ibandronic acid, may be formulated for oral administration, for example, with an inert diluent or with an edible carrier, or it may be enclosed in hard or soft shell gelatin capsules, compressed into tablets, or incorporated directly with the food of the diet. For oral therapeutic administration, the active compound may be incorporated with an excipient and used in the form of ingestible tablets, buccal tablets, coated tablets, troches, capsules, elixirs, dispersions, suspensions, solutions, syrups, wafers, patches, and the like.

Tablets, troches, pills, capsules and the like may also contain one or more of the following: a binder such as gum tragacanth, acacia, corn starch or gelatin; an excipient, such as dicalcium phosphate; a disintegrating agent such as corn starch, potato starch, alginic acid and the like; a lubricant such as magnesium stearate; a sweetening agent such as sucrose, lactose or saccharin; or a flavoring agent such as peppermint, oil of wintergreen or cherry flavoring. When the unit dosage form is a capsule, it may contain, in addition to materials of the above type, a liquid carrier. Various other materials may be present as coating, for instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. It may be desirable for material in a dosage form or pharmaceutical composition to be pharmaceutically pure and substantially non toxic in the amounts employed.

In some embodiments, an osteoclast inhibitor, including a bisphosphonate, such as zoledronic acid, neridronic acid, etc., is in a dosage form containing one of, or a combination of, the ingredients in the Table E below.

TABLE E

Iron
Methyl Paraben
Propyl Paraben
Sorbitol
Carob Bean Gum
Mannitol
Gum Tragacanth
Guar Gum

TABLE E-continued

Benzoic Acid
Sodium Benzoate
Garlic and Oil of Garlic
Oil of Rue
Propyl Gallate
Gum Ghatti
Gum Arabic
*Sterculia* Gum (karaya gum)
Indian Dill Seed
Pulps
Clove Bud Extract
Clove Bud Oil
Clove Bud Oleoresin
Clove Leaf Oil
Clove Stem Oil
Cholic acid
Desoxycholic acid
Glycocholic acid
Ox bile extract
Taurocholic acid
Sorbose
Sodium thiosulfate
Gelatin
Mustard or Oil of Mustard (Brown and Yellow)
Glycyrrhiza
Ammoniated Glycyrrhizin
Licorice
Caprylic Acid
Stannous Chloride
Ammonium bicarbonate
Ammonium carbonate
Ammonium chloride
Ammonium hydroxide
Ammonium phosphate, such as ammonium phosphate dibasic or Ammonium phosphate monobasic
Ammonium sulfate
Calcium iodate
Potassium iodate
Potassium iodide
Aconitic Acid
Calcium carbonate
Potassium bicarbonate
Sodium bicarbonate
Sodium carbonate
Sodium sesquicarbonate
Glycerin and Glycerides
Dextran
Dextrins
Corn dextrins
Calcium acetate
Calcium chloride
Calcium gluconate
Calcium phytate
Calcium hydroxide
Calcium oxide
Succinic acid
Butylated Hydroxytoluene (BHT)
Calcium hexametaphosphate
Calcium phosphate dibasic
Calcium phosphate monobasic
Calcium phosphate tribasic
Calcium pyrophosphate
Phosphoric acid
Potassium phosphate dibasic
Potassium phosphate monobasic
Potassium phosphate tribasic
Potassium polymetaphosphate
Potassium pyrophosphate
Potassium tripolyphosphate
Sodium acid pyrophosphate
Sodium hexametaphosphate
Sodium metaphosphate
Sodium phosphate dibasic
Sodium phosphate monobasic
Sodium phosphate tribasic
Sodium pyrophosphate, tetrabasic
Sodium tetrametaphosphate
Sodium tetraphosphate
Sodium trimetaphosphate
Sodium tripolyphosphate
Sulfuric Acid
alpha-Tocopherol acetate
Tocopherols
Choline Bitartrate
Choline Chloride
Aluminum ammonium sulfate
Aluminum hydroxide
Aluminum oleate
Aluminum palmitate
Aluminum potassium sulfate
Aluminum sodium sulfate
Aluminum sulfate
Sodium aluminate
Sodium aluminum phosphate, acidic
Sodium aluminum phosphate, basic
Sodium phosphoaluminate
Beeswax (yellow or white)
Japan wax
Carnauba wax
Corn Sugar (Dextrose)
Corn Syrup
Invert Sugar
Inositol
Calcium stearate
Hydrogenated tallow
Stearic acid
Tallow
Malic acid
L-Malic acid
Calcium sorbate
Potassium sorbate
Sodium sorbate
Sorbic acid
Sulfamic acid
Sodium hydrosulfite
Zinc hydrosulfite
Tall oil
Fish oil, hydrogenated
Sucrose
Agar-agar
Ammonium alginate
Calcium alginate
Potassium alginate
Propylene glycol alginate
Sodium alginate
Propylene Glycol
Propylene glycol monostearate
Brown algae
Red algae
Calcium glycerophosphate
Manganese glycerophosphate
Magnesium glycerophosphate
Potassium glycerophosphate
Potassium hydroxide
Sodium hydroxide
Potassium metabisulfite
Sodium bisulfite
Sodium metabisulfite
Sodium sulfite
Sulfur dioxide
Magnesium phosphate, dibasic
Magnesium carbonate
Magnesium chloride
Magnesium hydroxide
Magnesium oxide
Magnesium stearate
Magnesium sulfate
Magnesium phosphate, tribasic
Adipic acid
Hydrogenated soybean oil
Ethyl formate
Formic acid
Sodium formate
Carrageenan
Nutmeg and Mace
Zinc acetate
Zinc carbonate
Zinc chloride
Zinc oxide
Zinc sulfate TABLE E-continued

- Caramel
- Lard
- Lard oil
- Papain
- Gum guaiac
- Coconut oil
- Linoleic acid
- Oleic acid
- Peanut oil
- Calcium hypophosphite
- Manganous hypophosphite
- Potassium hypophosphite
- Sodium hypophosphite
- Pectin, amidated
- Pectin, high ester
- Pectin, low acid
- Pectinates
- Pectinic acid
- Carboxymethyl cellulose
- Cellulose acetate
- Ethyl cellulose
- Hydroxypropylmethyl cellulose
- Methylcellulose
- Sodium Carboxymethyl cellulose
- Rennet
- Tannic acid (hydrolyzable gallotannins)
- Acetic acid
- Sodium acetate
- Sodium diacetate
- Pyridoxine
- Pyridoxine hydrochloride
- Sodium oleate
- Sodium palmitate
- Ethyl acrylate, monomeric
- Methyl acrylate, monomeric
- Ethyl acrylate, polymeric
- Methyl acrylate, polymeric
- Bentonite
- Clay (kaolin)
- Corn silk
- Ammonium citrate
- Calcium citrate
- Citric acid
- Isopropyl citrate
- Potassium citrate
- Sodium citrate
- Stearyl citrate
- Triethyl citrate
- Biotin
- Enzymatically hydrolyzed casein
- Acid hydrolyzed proteins
- Enzymatically hydrolyzed protein
- Soy sauces
- Yeast autolyzates
- Caffeine
- L-Glutamic acid
- L-Glutamic acid hydrochloride
- Monoammonium L-glutamate
- Monopotassium L-glutamate
- Monosodium L-glutamate
- Calcium Lactate
- L(+)-calcium lactate
- D(−)-Lactic acid
- Lactic acid
- L(+)-lactic acid
- Butylated Hydroxyanisole (BHA)
- D- or DL-Calcium pantothenate
- D-Pantothenyl alcohol
- D- or DL-Sodium pantothenate
- Urea
- Thiamine hydrochloride
- Thiamine mononitrate
- Magnesium gluconate
- Potassium gluconate
- Sodium gluconate
- Zinc gluconate
- Vitamin B12 (cyanocobalamin)
- Vitamin D2 (ergocalciferol)
- Vitamin D3 (cholecalciferol)
- Potassium chloride TABLE E-continued

- Sodium chloride
- Soy protein isolate
- Hydrochloric acid
- Copper (cupric) gluconate
- Copper (cupric) sulfate
- Cuprous iodide
- Calcium caseinate
- Casein
- Sodium caseinate
- Aluminum calcium silicate
- Calcium silicate
- Diatomaceous earth (filter aid)
- Magnesium silicate
- Perlite (filter aid)
- Potassium silicate
- Silica aerogel
- Silicon dioxides
- Sodium aluminosilicate
- Sodium calcium aluminosilicate
- Sodium silicate
- Talc (basic magnesium silicate)
- Tricalcium silicate
- L(+)-potassium acid tartrate
- L(+)-sodium tartrate
- L(+)-tartaric acid
- Manganous chloride
- Manganous citrate
- Manganous gluconate
- Manganous oxide
- Manganous sulfate
- Lecithin
- Lecithin, hydrogen peroxide bleached
- Riboflavin
- Riboflavin-5'-phosphate
- Calcium propionate
- Dilauryl thiodipropionate
- Propionic acid
- Sodium propionate
- Thiodipropionic acid
- Hydrogen peroxide
- Carbon dioxide
- Nickel (elemental)
- Niacin (nicotinic acid)
- Niacinamide (nicotinamide)
- Carotene (beta-carotene)
- L-Ascorbic acid
- Ascorbyl palmitate (palmitoyl L-ascorbic)
- Calcium L-ascorbate
- Erythorbic acid (D-isoascorbic acid)
- Sodium erythorbate (sodium D-isoascorbate)
- Sodium L-ascorbate
- Acetylated Distarch Adipate
- Acetylated Distarch Glycerol
- Acetylated Distarch Phosphate
- Acetylated Distarch Oxypropanol
- Acid Modified Starch
- Arrowroot Starch
- Bleached Starch
- Cornstarch
- Distarch Glycerol
- Distarch Oxypropanol
- Distarch Phosphate
- High Amylose Cornstarch
- Hydroxypropyl Distarch Glycerol
- Hydroxypropyl Distarch Phosphate
- Hydroxypropyl Starch
- Hydroxypropyl Starch, oxidized
- Milo Starch
- Monostarch Phosphate
- Potato starch
- Pregelatinized starch
- Rice Starch
- Sodium Hydroxide Gelatinized Starch
- Starch Acetate
- Starch Aluminum Octenyl Succinate
- Starch Sodium Succinate
- Starch Sodium Octenyl Succinate
- Succinyl Distarch Glycerol
- Tapioca Starch
- Waxy Maize Starch

TABLE E-continued

Wheat Starch
Phosphated Distarch Phosphate
Starch, Sodium Hypochlorite oxidized
Vitamin A
Vitamin A acetate
Vitamin A palmitate
Diacetyl
Starter distillate
Carbonyl Iron
Carbonyl Iron
Electrolytic Iron
Electrolytic Iron
Ferric ammonium citrate
Ferric chloride
Ferric citrate
Ferric oxide
Ferric phosphate
Ferric pyrophosphate
Ferric sodium pyrophosphate
Ferric sulfate
Ferrous ascorbate
Ferrous carbonate
Ferrous citrate
Ferrous fumarate
Ferrous gluconate
Ferrous lactate
Ferrous sulfate
Ferrous sulfate
Iron caprylate
Iron linoleate
Iron naphthenate
Iron oxides
Iron peptonate
Iron polyvinylpyrrolidone
Iron tallate
Sodium ferric EDTA
Sodium ferricitropyrophosphate
Dietary Iron
Ferric oxide
Potassium carbonate
Calcium glycerophosphate
Cellulose, such as microcrystalline cellulose
Titanium dioxide Some compositions or dosage forms may be a liquid, or may comprise a solid phase dispersed in a liquid.

An osteoclast inhibitor, such as zoledronic acid, minodronic acid, or ibandronic acid may be formulated for parental or intraperitoneal administration. Solutions of the active compounds as free acids or pharmacologically acceptable salts can be prepared in water suitably mixed with a surfactant, such as hydroxypropylcellulose. A dispersion can also have an oil dispersed within, or dispersed in, glycerol, liquid polyethylene glycols, and mixtures thereof. Under ordinary conditions of storage and use, these preparations may contain a preservative to prevent the growth of microorganisms.

In some embodiments, an oral dosage form may comprise a silicified microcrystalline cellulose such as PROSLOV®. For example, about 20% (wt/wt) to about 70% (wt/wt), about 10% (wt/wt) to about 20% (wt/wt), about 20% (wt/wt) to about 40% (wt/wt), about 25% (wt/wt) to about 30% (wt/wt), about 40% (wt/wt) to about 50% (wt/wt), or about 45% (wt/wt) to about 50% (wt/wt) silicified microcrystalline cellulose may be present in an oral dosage form or a unit of an oral dosage form.

In some embodiments, an oral dosage form may comprise a crosslinked polyvinylpyrrolidone such as crospovidone. For example, about 1% (wt/wt) to about 10% (wt/wt), about 1% (wt/wt) to about 5% (wt/wt), or about 1% (wt/wt) to about 3% (wt/wt) crosslinked polyvinylpyrrolidone may be present in an oral dosage form or a unit of an oral dosage form.

In some embodiments, an oral dosage form may comprise a fumed silica such as AEROSIL®. For example, about 0.1% (wt/wt) to about 10% (wt/wt), about 0.1% (wt/wt) to about 1% (wt/wt), or about 0.4% (wt/wt) to about 0.6% (wt/wt) fumed silica may be present in an oral dosage form or a unit of an oral dosage form.

In some embodiments, an oral dosage form may comprise magnesium stearate. For example, about 0.1% (wt/wt) to about 10% (wt/wt), about 0.1% (wt/wt) to about 1% (wt/wt), or about 0.4% (wt/wt) to about 0.6% (wt/wt) magnesium stearate may be present in an oral dosage form or a unit of an oral dosage form.

An oral dosage form comprising zoledronic acid or another bisphosphonate or osteoclast inhibitor may be included in a pharmaceutical product comprising more than one unit of the oral dosage form.

A pharmaceutical product containing oral dosage forms for daily use can contain 28, 29, 30, or 31 units of the oral dosage form for a monthly supply. An approximately 6 week daily supply can contain 40 to 45 units of the oral dosage form. An approximately 3 month daily supply can contain 85 to 95 units of the oral dosage form. An approximately six month daily supply can contain 170 to 200 units of the oral dosage form. An approximately one year daily supply can contain 350 to 380 units of the oral dosage form.

A pharmaceutical product containing oral dosage forms for weekly use can contain 4 or 5 units of the oral dosage form for a monthly supply. An approximately two month weekly supply can contain 8 or 9 units of the oral dosage form. An approximately six week weekly supply can contain about 6 units of the oral dosage form. An approximately three month weekly supply can contain 12, 13 or 14 units of the oral dosage form. An approximately six month weekly supply can contain 22 to 30 units of the oral dosage form. An approximately one year weekly supply can contain 45 to 60 units of the oral dosage form.

A pharmaceutical product may accommodate other dosing regimes. For example, a pharmaceutical product may comprise 5 to 10 units of the oral dosage form, wherein each unit of the oral dosage form contains about 40 mg to about 150 mg of zoledronic acid, minodronic acid, or ibandronic acid. Some pharmaceutical products may comprise 1 to 10 units of the oral dosage form, wherein the product contains about 200 mg to about 2000 mg of zoledronic acid, minodronic acid, or ibandronic acid. For such a product, each unit of the oral dosage form may be taken daily for 1 to 10 days or 5 to 10 days during a month, such as at the beginning of a month.

Some oral dosage forms comprising an osteoclast inhibitor—such as suitable bisphosphonates like zoledronic acid, minodronic acid, or ibandronic acid or salts thereof—may have enteric coatings or film coatings. In some embodiments, an oral dosage form of an osteoclast inhibitor comprises a tablet having an enteric coating. In some embodiments, an oral dosage form of an osteoclast inhibitor comprises a capsule having an enteric coating. In some embodiments, an oral dosage form of an osteoclast inhibitor comprises a tablet having a film coating. In some embodiments, an oral dosage form of an osteoclast inhibitor comprises a capsule having a film coating.

Useful doses for an antibody against RANK or RANKL, such as denosumab, may range from about 0.1 mg/kg to about 20 mg/kg, about 0.75 mg/kg to about 7.5 mg/kg, about 0.1 mg/kg to about 5 mg/kg, about 1 mg/kg to about 2 mg/kg, about 10 mg/kg to about 20 mg/kg, about 12 to about 17 mg/kg, about 15 mg/kg to about 20 mg/kg, about 1 mg/kg, about 1 mg/kg to about 10 mg/kg, or any value bounded by or in between these ranges based on the body weight of the mammal. The chosen dose may be administered repeatedly, particularly for chronic conditions, or the amount per dose may be increased or decreased as treatment progresses. The chosen dose may be administered one or more times per week, monthly, every two months, every three months, every six months, or every year.

In some embodiments, 60 mg of denosumab is administered subcutaneously to patient in need of treatment. In some embodiments, the administration is repeated every six months.

There are a number of ways that some part of Compound 1 and/or Compound 2 may be removed from a zoledronic acid product. For example, HPLC, preparative TLC, crystallization, sublimation, or zone purification may be employed. Solvents that may be useful in HPLC, TLC, or crystallization, may include, but are not limited to, water or organic solvents, such as hexanes, diethyl ether, ethyl acetate, methyl acetate, acetone, acetic acid, acetonitrile, tetrahydrofuran, ethanol, methanol, isopropyl alcohol, chloroform, diethyl ether, toluene, dimethylformamide, benzene, etc. Gradients, or two solvent systems may be employed as well. For example, an HPLC separation may begin by elution with water, after some time eluting with water, an organic solvent, such as acetonitrile, methanol, ethanol, ethyl acetate, acetone, acetic acid, methyl acetate, or another solvent could gradually be added to the water, or may replace the water entirely. Similarly, crystallization or recrystallization may employ a single solvent, or a combination of solvents. For example, zoledronic acid or a salt thereof, such as a disodium salt, might be recrystallized from water, ethanol, methanol, diethyl ether, methyl acetate, acetic acid, etc., or a combination of these solvents or others. In some embodiments, zoledronic acid or a salt thereof, such as a disodium salt, may be dissolved in one solvent, such as water or acetic acid, and crystallized by a second solvent or solvent system, such as hexane, diethyl ether, chloroform, dichloromethane, ethyl acetate, methyl acetate, acetic acid, ethanol, methanol, or a combination thereof. In some embodiments, a disodium salt of zoledronic acid is dissolved in water, and then crystallized by adding hexane. In some embodiments, a disodium salt of zoledronic acid is dissolved in water, and then crystallized by adding diethyl ether. In some embodiments, a disodium salt of zoledronic acid is dissolved in water, and then crystallized by adding chloroform. In some embodiments, a disodium salt of zoledronic acid is dissolved in water, and then crystallized by adding dichloromethane. In some embodiments, a disodium salt of zoledronic acid is dissolved in water, and then crystallized by adding ethyl acetate. In some embodiments, a disodium salt of zoledronic acid is dissolved in water, and then crystallized by adding methyl acetate. In some embodiments, a disodium salt of zoledronic acid is dissolved in water, and then crystallized by adding acetic acid. In some embodiments, a disodium salt of zoledronic acid is dissolved in water, and then crystallized by adding ethanol. In some embodiments, a disodium salt of zoledronic acid is dissolved in water, and then crystallized by adding methanol. For embodiments employing water and a second solvent, the ratio of water to the second solvent (water:second solvent) may be about 1:100 to about 100:1, about 1:10 to about 1:5, about 1:5 to about 1:4, about 1:4 to about 1:3, about 1:3 to about 1:2, about 1:2 to about 1:1, about 1:1 to about 2:1, about 2:1 to about 3:1, about 3:1 to about 4:1, about 4:1 to about 5:1, or about 1:1 to about 10:1.

In some embodiments, a combination of two methods recited in the paragraph above may be employed, such as HPLC or TLC and crystallization. In some embodiments, a method may be repeated, such as HPLC, preparative TLC, crystallization, sublimation, or zone purification. In some embodiments, a purification method recited in the paragraph above may be performed twice. In some embodiments, a purification method recited in the paragraph above may be performed three or four times.

Some oral dosage forms comprising zoledronic acid or a salt thereof may have enteric coatings or film coatings.

In the examples below, zoledronic acid was administered in the disodium salt form as disodium zoledronate tetrahydrate. No bioavailability enhancing agents were used in the test compositions.

Example 1

Effect of Orally Administered Zoledronic Acid in Rat Model of Inflammatory Pain

Method:

The effect of orally administered zoledronic acid on inflammatory pain was examined using the rat complete Freund's adjuvant (CFA) model. Inflammatory pain was induced by injection of 100% CFA in a 75 μL volume into the left hind paws of Sprague-Dawley® rats on day 0, followed by assessments on days 1-3. Animals were orally administered vehicle (control), zoledronic acid 18 mg/m$^2$ (or 3 mg/kg), zoledronic acid 120 mg/m$^2$ (or 20 mg/kg), or zoledronic acid 900 mg/m$^2$ (or 150 mg/kg) daily on days 1-3. Drug was dissolved in distilled water and prepared fresh daily. Animals were fasted prior to dosing. Under current FDA guidelines for extrapolating starting dosages from animals to humans, dosages expressed in mg/m$^2$ are considered equivalent between mammalian species. Thus, for example, 18 mg/m$^2$ in a rat is considered equivalent to 18 mg/m$^2$ in a human being, while 3 mg/kg in a rat may not be equivalent to 3 mg/kg in a human being.

Values for inflammatory pain (mechanical hyperalgesia) in the vehicle and drug-treated animals were obtained on day 0 prior to CFA injection, and at baseline and post-treatment on days 1-3. Pain was assessed using a digital Randall-Selitto device (dRS; IITC Life Sciences, Woodland Hills, Calif.). Animals were placed in a restraint sling that suspended the animal, leaving the hind limbs available for testing. Paw compression threshold was measured by applying increasing pressure to the plantar surface of the hind paw with a dome-shaped tip placed between the 3rd and 4th metatarsus. Pressure was applied gradually over approximately 10 seconds. Measurements were taken from the first observed nocifensive behavior of vocalization, struggle or withdrawal. A cut-off value of 300 g was used to prevent injury to the animal.

Reversal of inflammatory pain was calculated according to the formula:

$$\% \text{ reversal} = (\text{Post-treatment} - \text{Post-CFA baseline})/(\text{Pre-CFA baseline} - \text{Post-CFA baseline}) \times 100.$$

The experiment was carried out using 9-10 animals per group.

Results:

Oral administration of zoledronic acid significantly improved inflammatory pain thresholds compared to vehicle. Pain threshold measurements taken at various times are shown in FIG. 1. Paw compression thresholds in the 18 mg/m$^2$ group were higher than for vehicle during the entire measurement period after 30 minutes from the start of treatment. On day three, paw compression thresholds for both the 18 mg/m$^2$ and 900 mg/m$^2$ groups were greater than for vehicle. An improvement in pain threshold of 49% and 83% from baseline was observed for the 18 mg/m$^2$ and the 900 mg/m$^2$ groups respectively.

Orally administered zoledronic acid produced a 29% reversal of inflammatory pain at the 18 mg/m$^2$, and a 48% reversal at the 900 mg/m$^2$ dose. This magnitude of effect is comparable to that obtained with clinical doses of commercially available NSAIDs when tested in a similar model of inflammatory pain. Under current FDA guidelines, the reference body surface area of a human adult is 1.62 m$^2$. Thus, a daily dose of 18 mg/m$^2$ corresponds to a monthly dose of about 500-560 mg/m$^2$ or a human dose of about 800-900 mg.

Surprisingly, the two higher doses resulted in thresholds that were lower than vehicle on the first two days of dosing. The 120 mg/m$^2$ group was approximately equal or inferior to vehicle at all time points during the assessment period. While the 900 mg/m$^2$ group showed effectiveness on day 3, this result was accompanied by significant toxicity necessitating euthanization of all the animals in this group two days after cessation of dosing.

Example 2

Effect of Orally Administered Zoledronic Acid in Rat Model of Arthritis Pain
Method:

The effect of orally administered zoledronic acid on arthritis pain was examined in the rat complete Freund's adjuvant (CFA) model of arthritis pain. In this model, injection of 100% complete Freund's adjuvant (CFA) in a 75 µL volume into the left hind paws is followed by a 10-14 day period to allow for the development of arthritis pain. Animals were orally administered vehicle (control), zoledronic acid 54 mg/m$^2$ (or 9 mg/kg), or zoledronic acid 360 mg/m$^2$ (or 60 mg/kg), divided in three equal daily doses on the first three days post CFA injection. Drug was dissolved in distilled water and prepared fresh daily. Animals were fasted prior to dosing.

Arthritis pain (mechanical hyperalgesia) in the vehicle and drug-treated animals was evaluated on day 14 post CFA injection using a digital Randall-Selitto device (dRS; IITC Life Sciences, Woodland Hills, Calif.). Animals were placed in a restraint sling that suspended the animal, leaving the hind limbs available for testing. Paw compression threshold was measured by applying increasing pressure to the plantar surface of the hind paw with a dome-shaped tip placed between the 3rd and 4th metatarsus. Pressure was applied gradually over approximately 10 seconds. Measurements were taken from the first observed nocifensive behavior of vocalization, struggle or withdrawal. A cut-off value of 300 g was used to prevent injury to the animal.

Reversal of arthritis pain in the ipsilateral (CFA-injected) paw was calculated according to the formula:

% reversal=(ipsilateral drug threshold−ipsilateral vehicle threshold)/(contralateral vehicle threshold−ipsilateral vehicle threshold)×100.

Figure 2A:
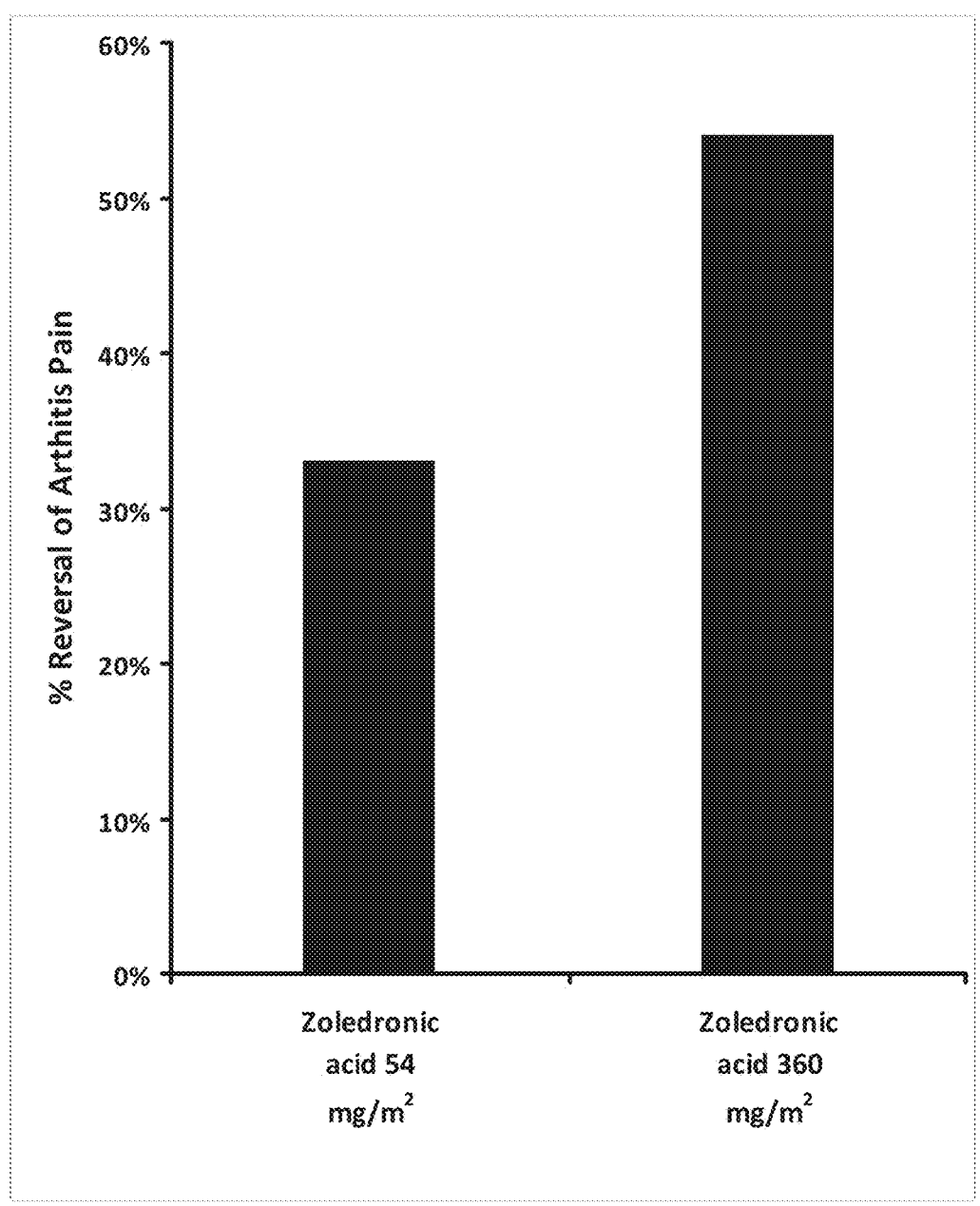
FIG. 2A is a graph depicting reversal of arthritis pain for two different doses of zoledronic acid in a rat model of arthritis pain.
Figure 2B:
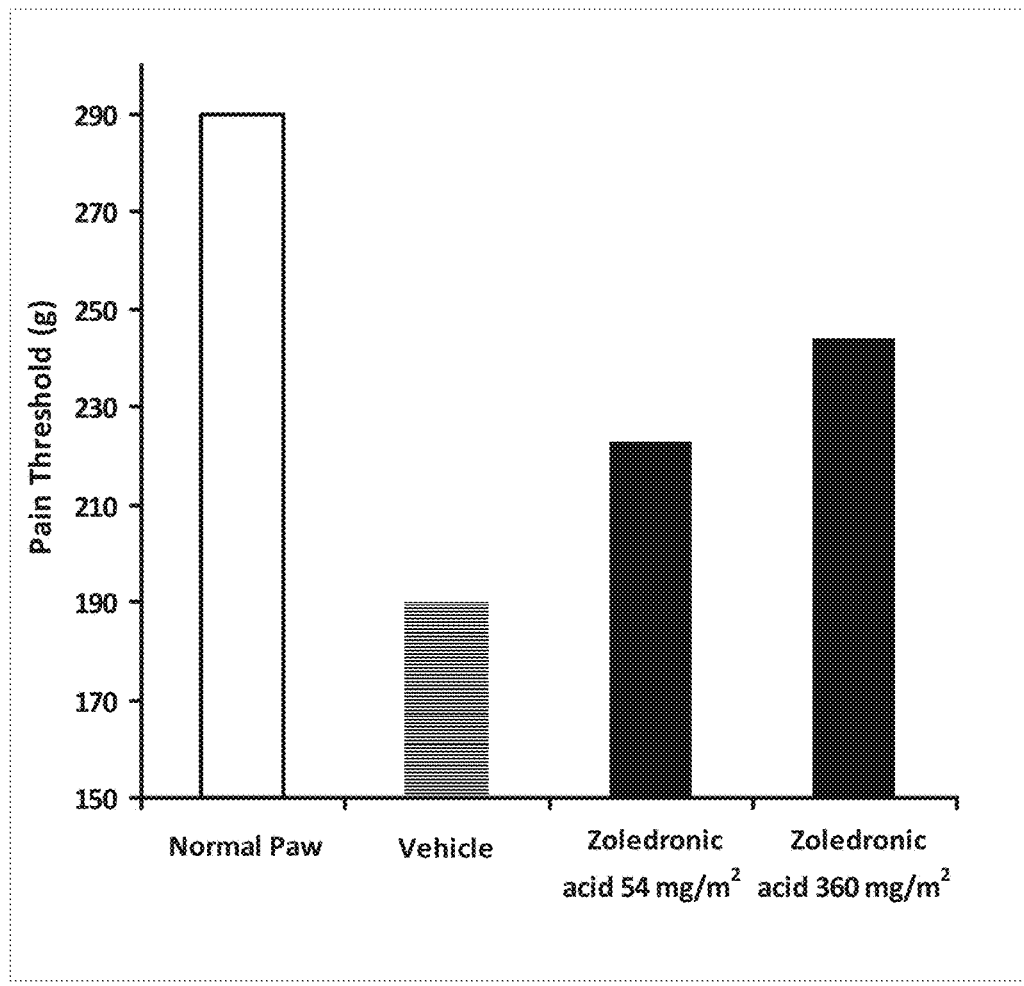
FIG. 2B is a graph depicting pain thresholds for two different doses of zoledronic acid in a rat model of arthritis pain.

The experiment was carried out using 7-10 animals per group.
Results:

Oral administration of zoledronic acid significantly improved arthritis pain thresholds compared to vehicle. As shown in FIGS. 2A and 2B, orally administered zoledronic acid produced a dose-dependent reversal of arthritis pain. A reversal of 33% was observed in the 54 mg/m$^2$ group, and reversal of 54% was observed in the 360 mg/m$^2$ group. Under current FDA guidelines, the reference body surface area of a human adult is 1.62 m$^2$. Thus, 54 mg/m$^2$ in a rat is equivalent to an implied human dose of about 87 mg, and 360 mg/m$^2$ in a rat is equivalent to an implied human dose of about 583 mg.

Example 3. Treatment of Complex Regional Pain Syndrome with Orally Administered Zoledronic Acid The effect of orally administered zoledronic acid was examined in the rat tibia fracture model of complex regional pain syndrome (CRPS). CRPS was induced in the rats by fracturing the right distal tibias of the animals and casting the fractured hindpaws for 4 weeks, as described in Guo T Z et al. (*Pain.* 2004; 108: 95-107). This animal model has been shown to replicate the inciting trauma (such as a fracture, a surgery, a crushing injury, a cutting injury, a scratch, or a puncture injury), natural history, signs, symptoms, and pathologic changes observed in human CRPS patients (Kingery W S et al., *Pain.* 2003; 104:75-84).

Animals were orally administered either vehicle (control) or zoledronic acid, in a dosage of 18 mg/m$^2$/day (3 mg/kg/day) for 28 days, starting on the day of fracture and casting. Drug was dissolved in distilled water and administered by gavage. Animals were fasted for 4 hours before and 2 hours after dosing. At the end of the 28-day period, casts were removed, and on the following day, the rats were tested for hindpaw pain, edema, and warmth.
Pain Assessments Pain was assessed by measuring hyperalgesia, and weight bearing.

To measure hyperalgesia, an up-down von Frey testing paradigm was used. Rats were placed in a clear plastic cylinder (20 cm in diameter) with a wire mesh bottom and allowed to acclimate for 15 minutes. The paw was tested with one of a series of eight von Frey hairs ranging in stiffness from 0.41 g to 15.14 g. The von Frey hair was applied against the hindpaw plantar skin at approximately midsole, taking care to avoid the tori pads. The fiber was pushed until it slightly bowed and then it was jiggled in that position for 6 seconds. Stimuli were presented at an interval of several seconds. Hindpaw withdrawal from the fiber was considered a positive response. The initial fiber presentation was 2.1 g and the fibers were presented according to the up-down method of Dixon to generate six responses in the immediate vicinity of the 50% threshold. Stimuli were presented at an interval of several seconds.

An incapacitance device (IITC Inc. Life Science, Woodland, Calif., USA) was used to measure hindpaw weight bearing, a postural effect of pain. The rats were manually held in a vertical position over the apparatus with the hindpaws resting on separate metal scale plates and the entire weight of the rat was supported on the hindpaws. The duration of each measurement was 6 seconds and 10 consecutive measurements were taken at 60-second intervals. Eight readings (excluding the highest and lowest ones) were averaged to calculate the bilateral hindpaw weight-bearing values. Weight bearing data were analyzed as the ratio between right (fracture) and left hindpaw weight bearing values ((2R/(R+L))×100%).
Edema Assessment A laser sensor technique was used to determine the dorsal-ventral thickness of the hindpaw. Before baseline testing the bilateral hindpaws were tattooed with a 2 to 3 mm spot on the dorsal skin over the midpoint of the third metatarsal. For laser measurements each rat was briefly anesthetized with isoflurane and then held vertically so the hindpaw rested on a table top below the laser. The paw was gently held flat on the table with a small metal rod applied to the top of the ankle joint. Using optical triangulation, a laser with a distance measuring sensor was used to determine the distance to the table top and to the top of the hindpaw at the tattoo site and the difference was used to calculate the dorsal-ventral paw thickness. The measurement sensor device used in these experiments (4381 Precicura, Limab, Goteborg, Sweden) has a measurement range of 200 mm with a 0.01 mm resolution.

Hindpaw Temperature Measurement

The temperature of the hindpaw was measured using a fine wire thermocouple (Omega, Stanford, Conn., USA) applied to the paw skin. Six sites were tested per hindpaw. The six measurements for each hindpaw were averaged for the mean temperature.

Results

Figure 3:
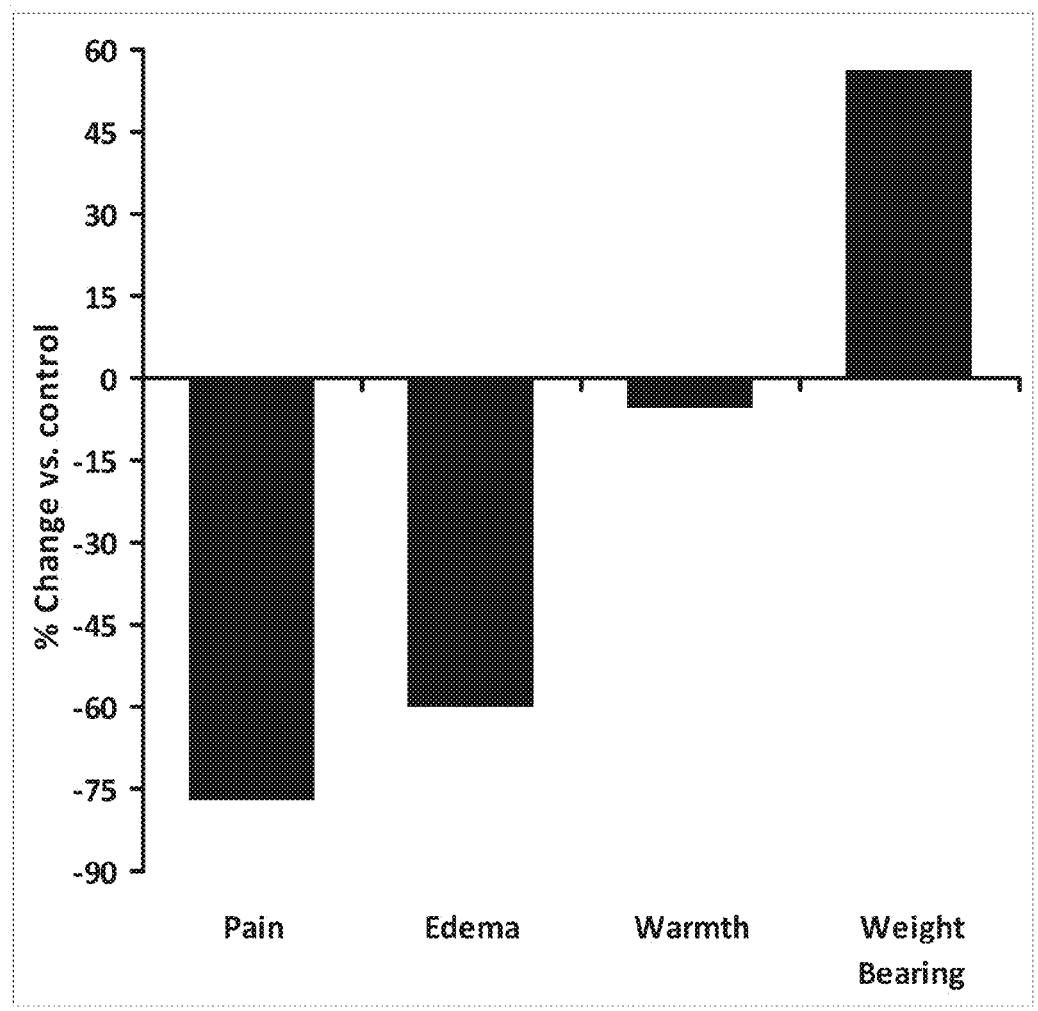
FIG. 3 is a graph summarizing the results for vehicle and zoledronic acid treated rats in a rat model of complex regional pain syndrome.

As illustrated in FIG. 3, treatment with orally administered zoledronic acid reversed pain, restored weight bearing, and prevented edema as compared to vehicle treated animals.

Figure 4:
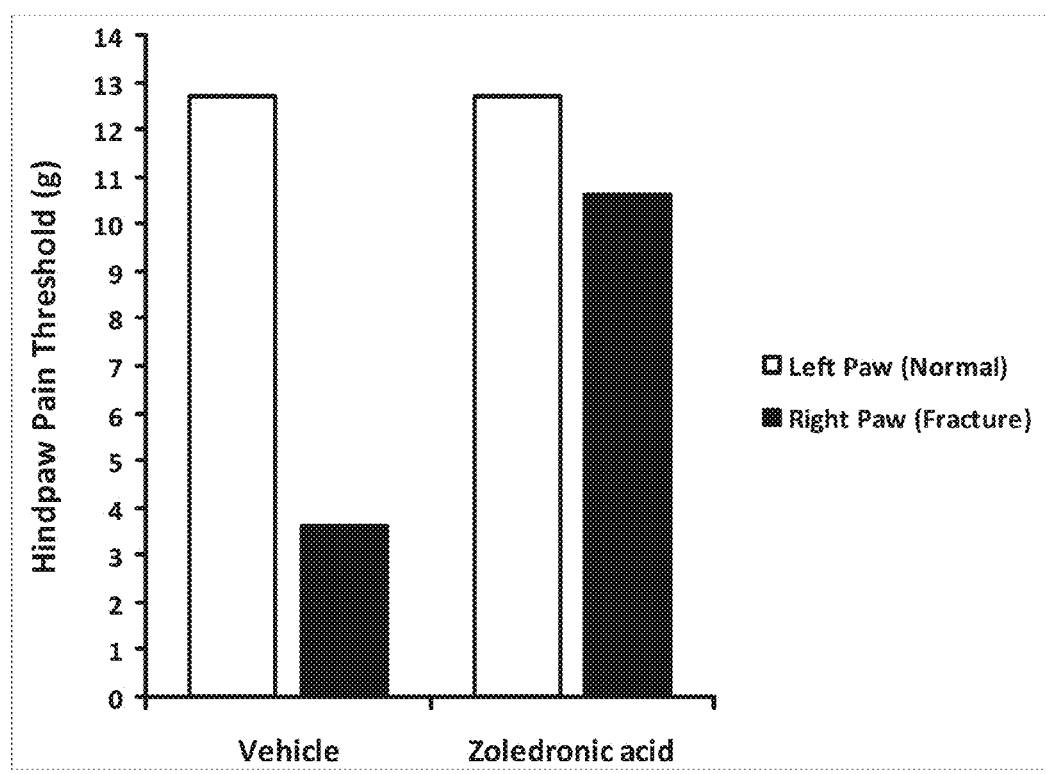
FIG. 4 depicts hindpaw pain thresholds for vehicle and zoledronic acid treated rats in a rat model of complex regional pain syndrome.

As illustrated in FIG. 4, von Frey pain thresholds for the right (fracture) hindpaw were reduced by 72% versus the contralateral (normal) hindpaw in vehicle treated animals. Zoledronate treatment reversed fracture induced pain by 77% as compared to vehicle treatment.

Figure 5:
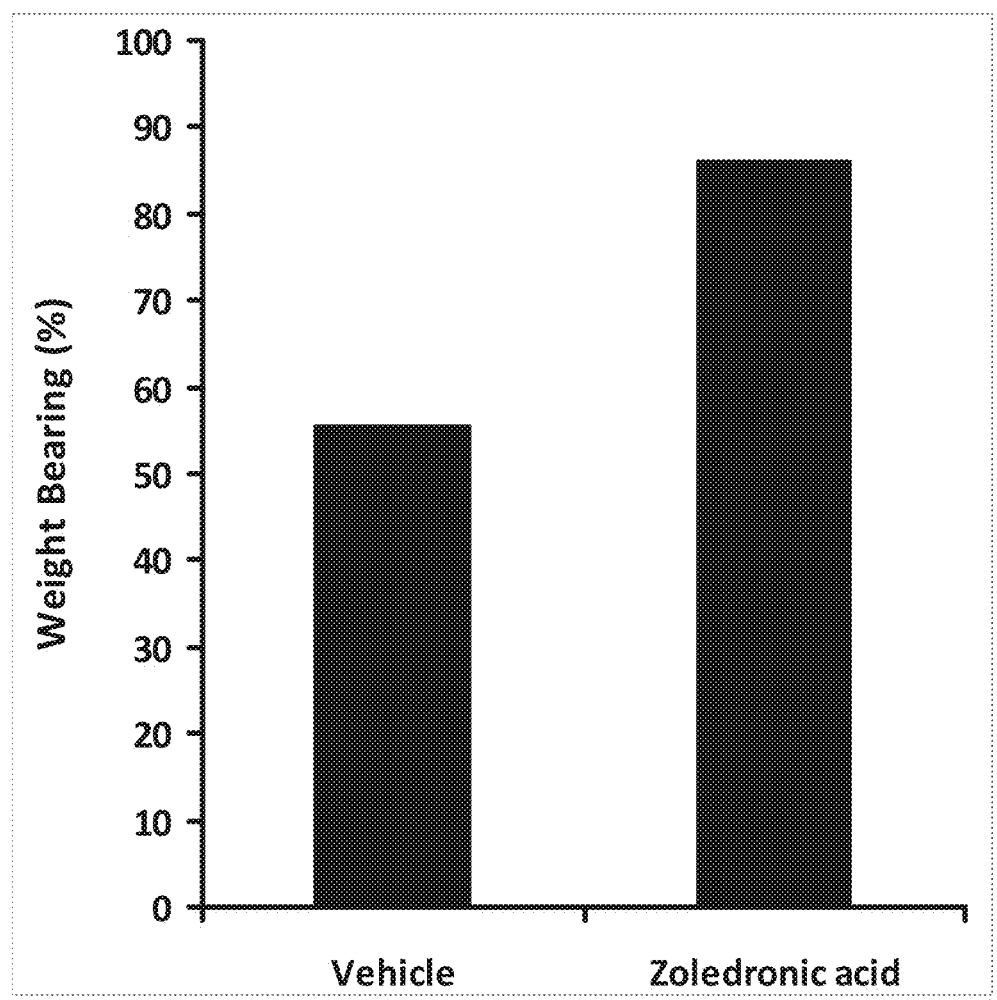
FIG. 5 depicts weight bearing for vehicle and zoledronic acid treated rats in a rat model of complex regional pain syndrome.

As illustrated in FIG. 5, reduction in weight bearing, a postural effect of pain, was significantly higher in the vehicle treated group as compared to the zoledronic acid treated group. Weight bearing on the fracture hindlimb was reduced to 55% of normal in the vehicle treated group. Zoledronate treatment significantly restored hindlimb weight bearing as compared to vehicle treatment (86% of normal).

Figure 6:
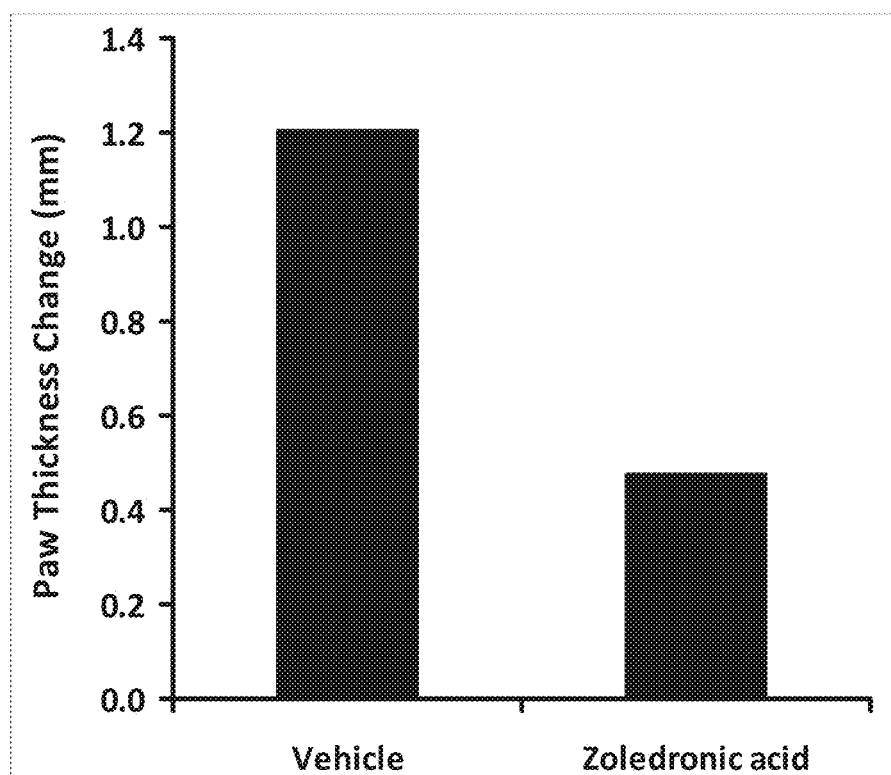
FIG. 6 depicts paw thickness change for vehicle and zoledronic acid treated rats in a rat model of complex regional pain syndrome.

As illustrated in FIG. 6, the expected increase in hindpaw thickness was greater in the vehicle treated group as compared to the zoledronic acid treated group, reflecting the development of edema. Zoledronate treatment reduced hindpaw edema by 60% versus vehicle treatment.

Zoledronic acid reduced hindpaw warmth by 5% versus vehicle treatment.

The daily dose in the above experiment was 18 mg/m$^2$/day. Under current FDA guidelines, the reference body surface area of a human adult is 1.62 m$^2$. Thus, a daily dose of 18 mg/m$^2$ corresponds to a monthly dose of about 500-560 mg/m$^2$ or a human dose of about 800-900 mg.

Example 4. Solubility of Disodium Salt of Zoledronic Acid

The aqueous solubility of zoledronic acid and disodium zoledronate tetrahydrate was determined. One gram of the test compound was measured in to a beaker. Demineralized water (pH 5.5) was then added in small increments to the test compound, and sonication was applied to the mixture. The procedure was continued until complete dissolution was achieved. Full dissolution was determined to have been reached when a clear solution was present with no visible material. The volume of water required to reach full dissolution was used to calculate a solubility value expressed in grams per 100 mL. The procedure was performed for each compound.

Results

Figure 7:
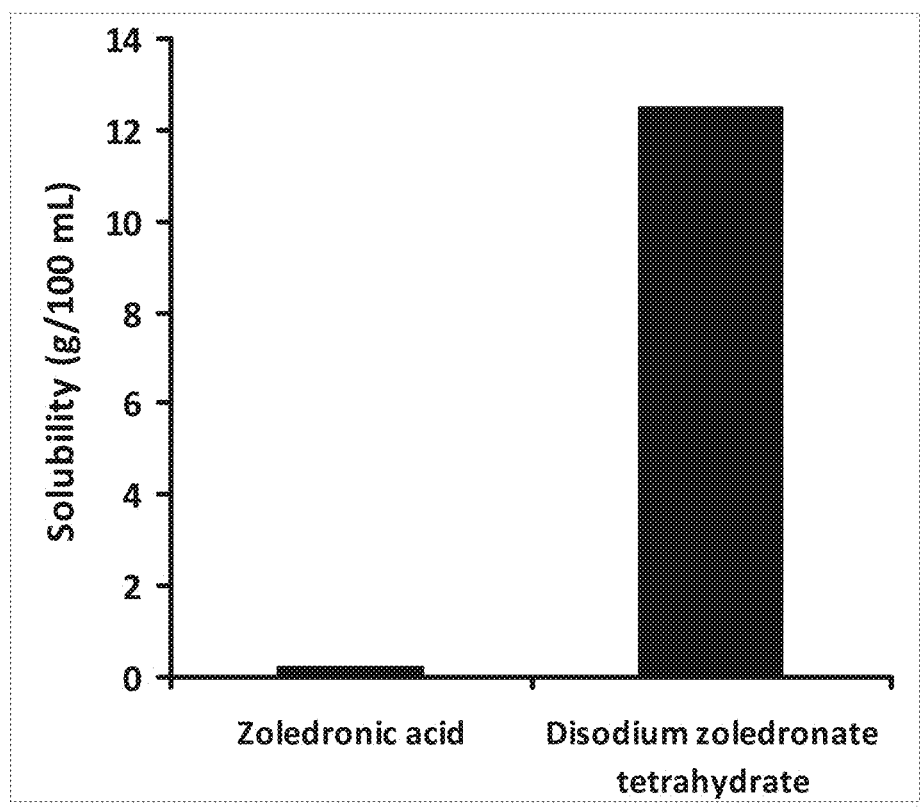
FIG. 7 depicts the aqueous solubility of disodium zoledronate tetrahydrate as compared to the diacid form of zoledronic acid.

As shown in FIG. 7, the aqueous solubility of disodium zoledronate tetrahydrate is approximately 50 times that of zoledronic acid. Disodium zoledronate tetrahydrate has a solubility of 12.5 g/100 mL compared to only 0.25 g/100 mL for zoledronic acid.

Example 5. Bioavailability of Orally Administered Zoledronic Acid and Disodium Zoledronate Tablets were manufactured containing either pure zoledronic acid or the disodium salt of zoledronic acid (disodium zoledronate tetrahydrate). Both types of tablets contained 50 mg of zoledronic acid equivalent per tablet. Identical excipients were used in both types of tablets, with amounts adjusted to account for the difference in molecular weights between the acid and the disodium salt.

Beagle dogs were orally administered tablets containing 150 mg zoledronic acid equivalent either in the form of disodium zoledronate (Group 1) or pure zoledronic acid (Group 2). Each animal was given three 50 mg equivalent tablets (150 mg total), which were administered together. The animal's oral cavity was wetted with water before placing the tablets on the back of the animal's tongue. Animals were fasted before and after dosing. Animals were 6 to 9 months of age and weighed 6 to 10 kg on the day of dosing. There were three dogs per group.

Serial blood samples were collected from each animal by venipuncture of the jugular vein at various points after dosing for measurement of plasma concentrations of zoledronic acid. Blood samples were collected into chilled tubes containing K$_2$EDTA as the anticoagulant. Samples were then centrifuged at approximately 3000 rpm at +4° C. for 10 minutes for plasma derivation. Plasma concentrations of zoledronic acid were measured using an LC/MS/MS method.

Results

Figure 8:
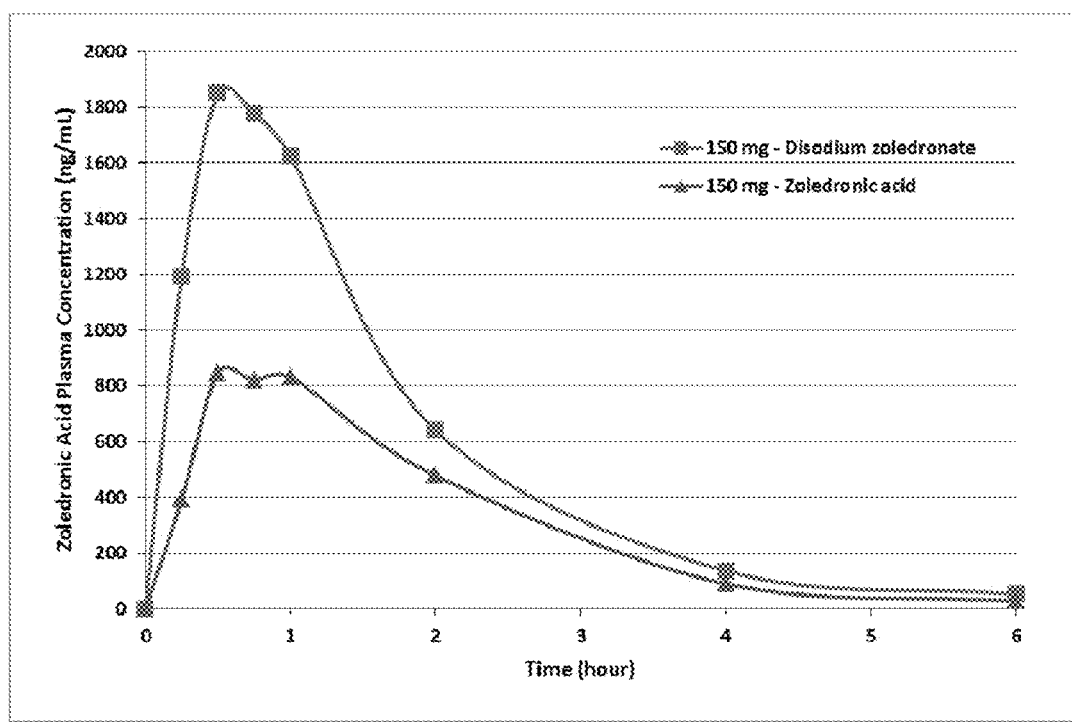
FIG. 8 depicts the plasma concentration of zoledronic acid in dogs over time after administration of 150 mg of the disodium salt form of zoledronic acid and the diacid form of zoledronic acid.

The average plasma concentrations of zoledronic acid for each group of dogs is summarized in Table 1 and illustrated in FIG. 8. Detectable plasma levels of zoledronic acid were observed for the entire 48 hours that they were measured.

TABLE 1

Zoledronic Acid plasma concentrations in beagle dogs

| | | Time (hour) | Plasma concentration (ng/mL) |
|---|---|---|---|
| Group 1 (N = 3) | Disodium Zoledronate Tablets (150 mg acid equivalent) | 0 | 0.00 |
| | | 0.25 | 1193.97 |
| | | 0.5 | 1852.12 |
| | | 0.75 | 1776.51 |
| | | 1 | 1626.56 |
| | | 2 | 640.57 |
| | | 4 | 136.93 |
| | | 6 | 53.11 |
| | | 8 | 26.97 |
| | | 12 | 13.74 |
| | | 24 | 6.78 |
| | | 48 | 5.39 |
| Group 2 (N = 3) | Zoledronic Acid Tablets (150 mg acid equivalent) | 0 | 0.00 |
| | | 0.25 | 390.92 |
| | | 0.5 | 846.19 |
| | | 0.75 | 819.15 |
| | | 1 | 831.77 |
| | | 2 | 477.76 |
| | | 4 | 90.11 |
| | | 6 | 28.22 |
| | | 8 | 15.10 |
| | | 12 | 6.13 |
| | | 24 | 3.18 |
| | | 48 | 1.84 |

Disodium zoledronate produced significantly higher plasma levels of zoledronic acid than pure zoledronic acid, indicating improved oral absorption with the salt form. Measured using peak plasma concentrations ($C_{max}$), the disodium salt resulted in a 119% actual and 74% weight-adjusted increase in bioavailability as compared to pure zoledronic acid. Measured using area under the plasma concentration curve (AUC$_{0-\infty}$), bioavailability was 84% and 46% greater with the disodium salt than with pure zoledronic acid, on an actual and weight-adjusted basis respectively. The average AUC$_{0-\infty}$ for the disodium salt was 4073 ng·h/mL and the average AUC$_{0-\infty}$ for the diacid was 2217 ng·h/mL. The $AUC_{0-\infty}$ was found to be dose proportional. Thus, for beagle dogs similar to those tested, about 3 mg to about 4 mg of the disodium salt would be expected to result in an $AUC_{0-\infty}$ of about 100 ng·h/mL, and about 7 mg to about 8 mg of the disodium salt would be expected to result in an $AUC_{0-\infty}$ of about 200 ng·h/mL.

Figure 9:
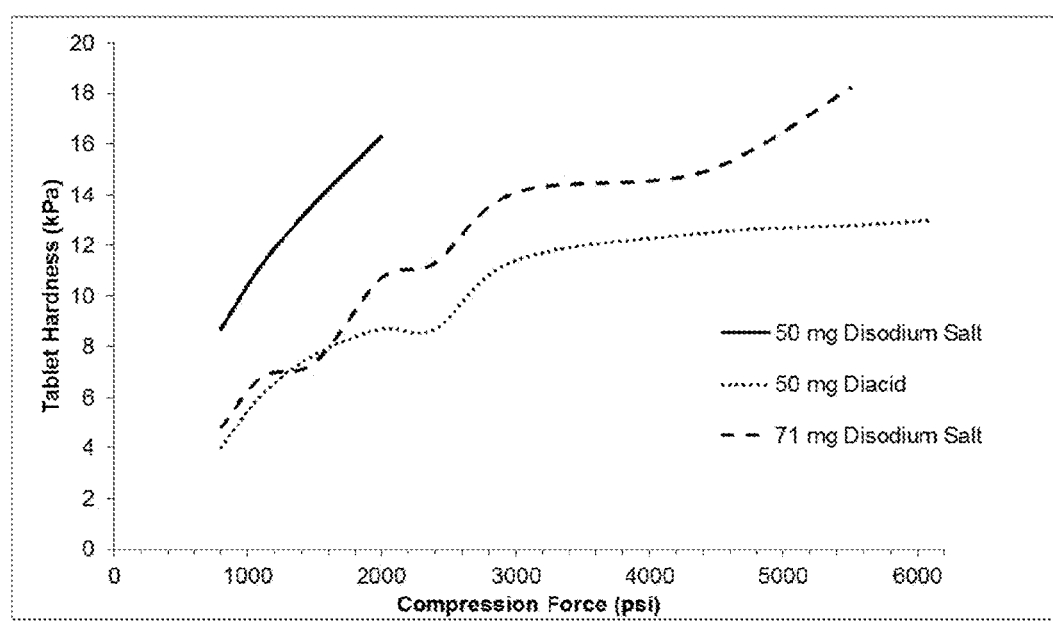
FIG. 9 depicts the compressibility of dosage forms containing zoledronic acid in the disodium salt form as compared to the diacid form.

Example 6. Hardness of Tablets Comprising Zoledronic Acid in the Free Acid and Disodium Salt Forms Tablets were prepared by blending zoledronic acid, either in the form of the free acid or the disodium salt, with identical excipients. For dosage forms with a greater amount of active, the amount of the excipients was reduced proportionally to keep the weight of the tablet at about 100 mg. After blending, the ingredients were compressed at varying pressures, followed by a film coating. The resulting tablets were then tested for hardness using a Dr. Schleuniger Pharmatron 8M Tablet Hardness Tester. The results are shown in Table 2 and FIG. 9.

TABLE 2

| Compression Force (psi) | Hardness (kPa) | | |
|---|---|---|---|
| | Diacid 50 mg | Disodium Salt 50 mg | Disodium Salt 71 mg |
| 800 | 4.0 | 8.7 | 4.8 |
| 1100 | 6.1 | 11.2 | 6.8 |
| 1500 | 7.7 | 13.7 | 7.4 |
| 2000 | 8.7 | 16.3 | 10.7 |
| 2400 | 8.7 | | 11.3 |
| 3000 | 11.4 | | 14.1 |
| 4400 | 12.5 | | 14.9 |
| 5500 | 12.8 | | 18.2 |
| 6100 | 13.0 | | |

Example 7. Effects of Zoledronic Acid on Patients with Osteoarthritis and BML

Some embodiments related to joint pain, bone marrow lesions, and osteoarthritis were conceived as a result of analyzing data from a clinical study. Some of the results of this study were reported by Laslett et al. in *Ann Rheum Dis* 2012; 71:1322-1328. Some of the description and data reported below was not published prior to filing the present application. Fifty-two (52) patients with clinical knee osteoarthritis and knee bone marrow lesions (BML) were randomized to receive either intravenous zoledronic acid (5 mg) or placebo in a double blind fashion. All patients had to have at least one bone marrow lesion (BML) in the affected knee on magnetic resonance imaging (MRI). All patients had x-ray of the knee for determination of joint space narrowing (JSN), which was graded according to the Osteoarthritis Research Society International (OARSI) atlas. Patients had either no joint space narrowing (OARSI Grade 0), or greater degrees of joint space narrowing (OARSI Grade 1 and Grade 2). Twenty six patients were treated with zoledronic acid (8, 6, and 12 with OARSI Grades 0, 1, and 2, respectively). Twenty six patients received placebo (8, 8, and 10 with OARSI Grades 0, 1 and 2, respectively).

Pain intensity was assessed, at baseline and at three months, using a 100 mm visual analog scale (VAS), with zero representing no pain and 100 representing extreme pain. The change in pain intensity from baseline to 3 months was calculated.

Figure 10:
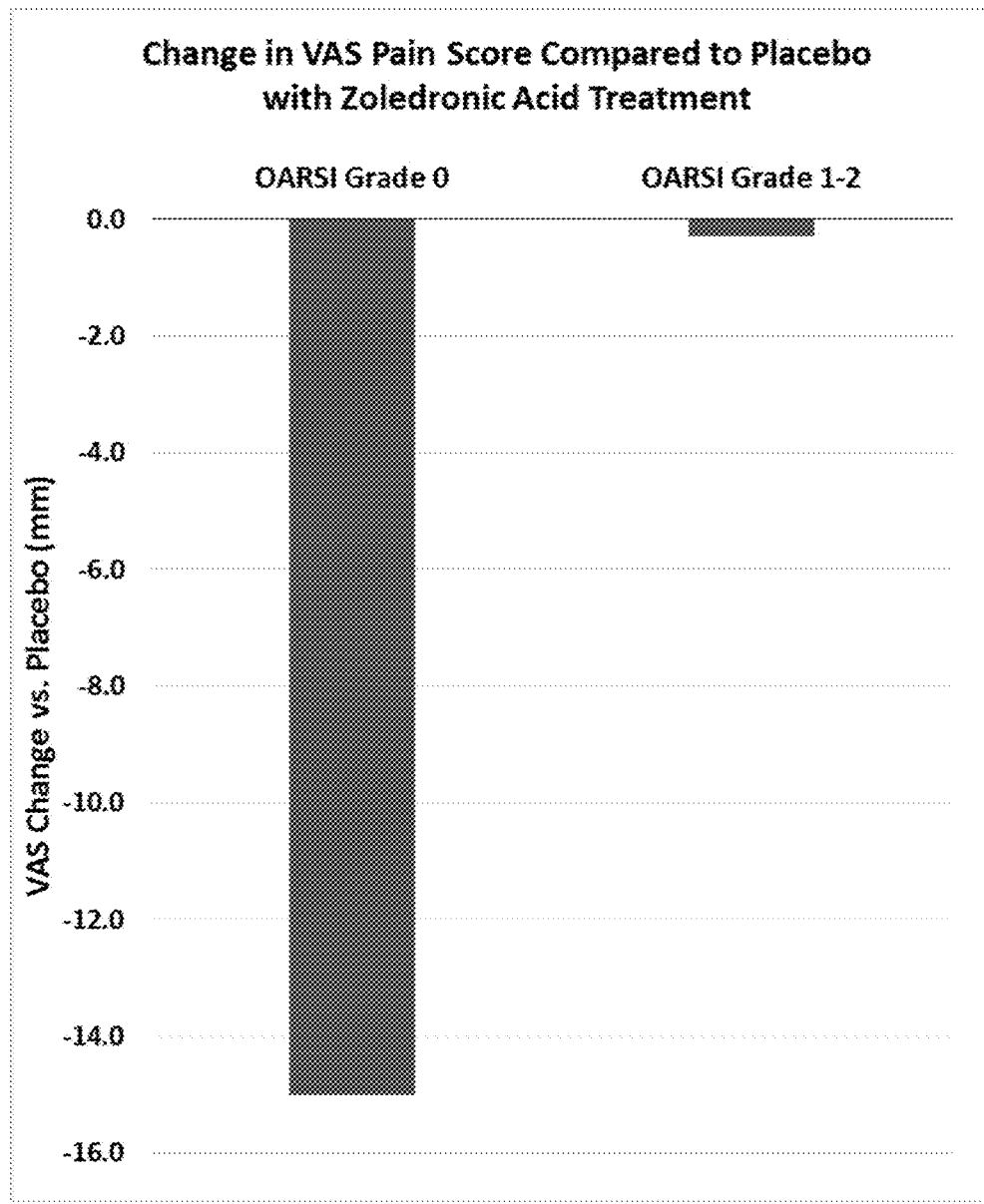
FIG. 10 depicts the change in VAS pain score compared to placebo at three months with zoledronic acid treatment in patients with osteoarthritis of the knee, bone marrow lesions, and different degrees of joint space narrowing.

With zoledronic acid treatment, pain was reduced significantly as compared to placebo in patients with no joint space narrowing (OARSI Grade 0), but not in patients with joint space narrowing (OARSI Grades 1-2). As shown in Table 3 and FIG. 10, average VAS scores were reduced by 15 mm as compared to placebo in the OARSI Grade 0 group, but only by 0.28 as compared to placebo in patients with OARSI Grades 1-2.

Figure 11:
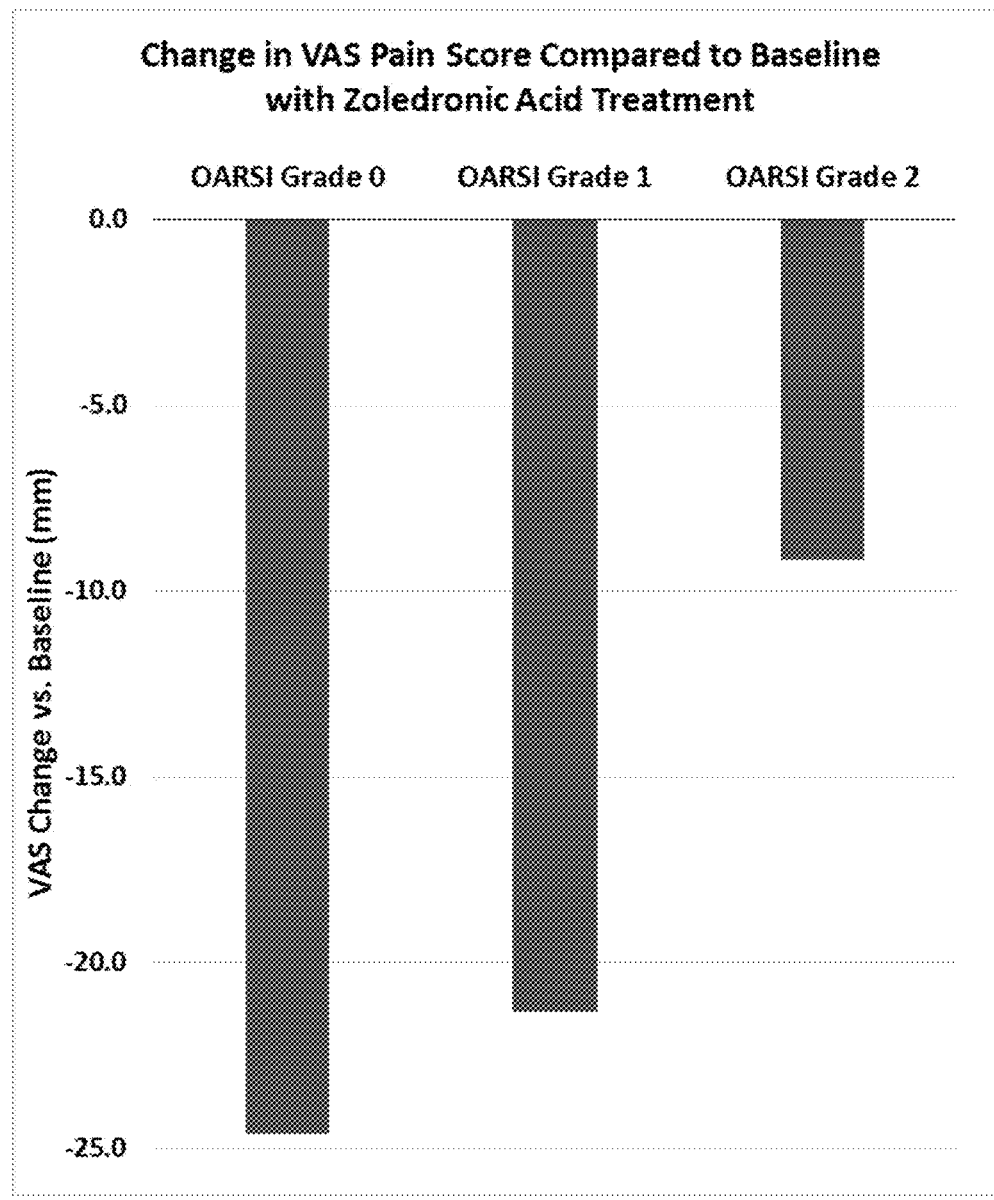
FIG. 11 depicts the change in VAS pain score compared to baseline at three months with zoledronic acid treatment in patients with osteoarthritis of the knee, bone marrow lesions, and different degrees of joint space narrowing.

In the zoledronic acid group, average VAS scores at 3 months decreased from baseline by approximately 25 mm and 21 mm in patients with OARSI Grades 0 and 1, respectively, but only by 9 mm in the OARSI Grade 2 patients (FIG. 11).

TABLE 3

Change in VAS Pain Scores at Three Months by OARSI Grade (mm)

| | OARSI Grade 0 | OARSI Grades 1-2 |
|---|---|---|
| Zoledronic Acid | −24.6 | −13.2 |
| Placebo | −9.6 | −12.9 |
| Difference from Placebo | −15.0 | −0.28 |

With zoledronic acid treatment, pain was reduced significantly as compared to placebo in patients with baseline VAS pain intensity scores of 50 mm or greater, but not in patients with baseline VAS scores less than 50 mm. As shown in Table 4, average VAS scores were reduced by 9 mm as compared to placebo in the patients with baseline VAS≥50 mm, but only by 0.6 as compared to placebo in patients with baseline VAS<50 mm.

TABLE 4

Change in VAS Pain Scores at Three Months by Baseline VAS (mm)

| | Baseline VAS ≥50 mm | Baseline VAS <50 mm |
|---|---|---|
| Zoledronic Acid | −26.2 | −7.3 |
| Placebo | −17.2 | −6.7 |
| Difference from Placebo | −9.0 | −0.6 |

Figure 12:
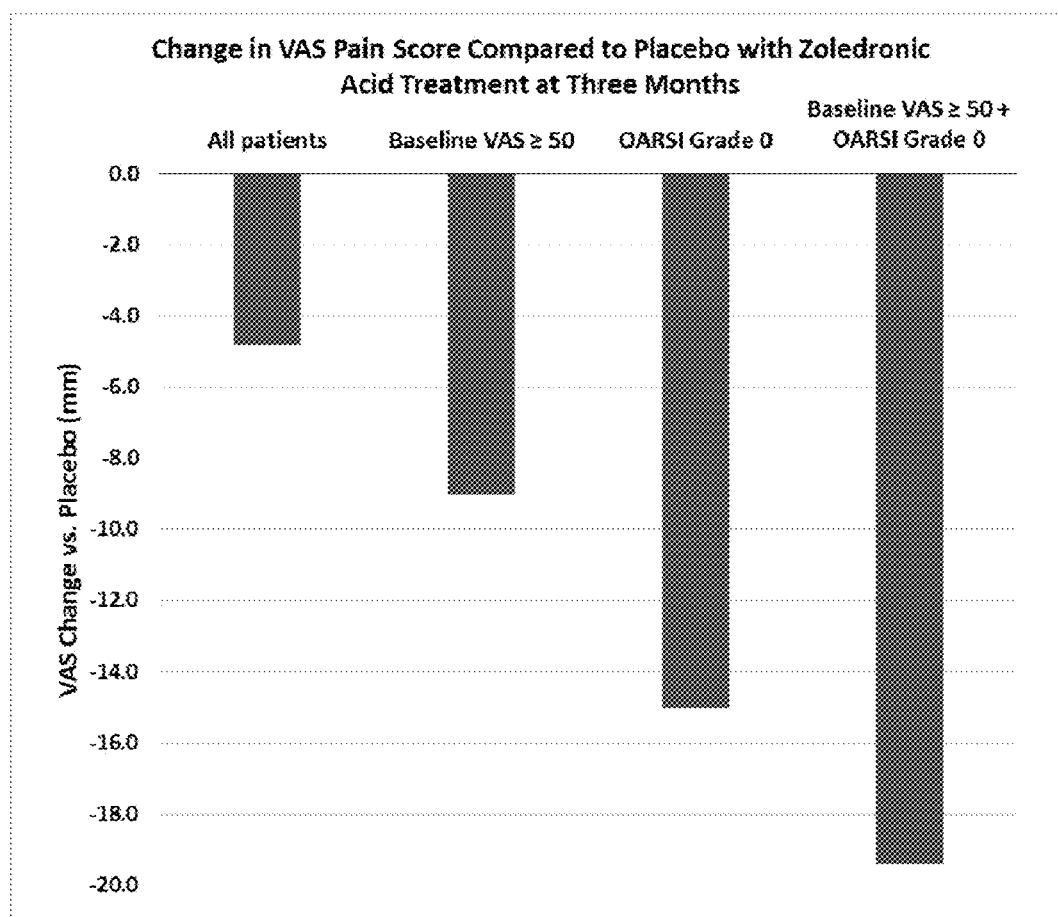
FIG. 12 depicts the change in VAS pain score compared to placebo at three months with zoledronic acid treatment in different subgroups of patients with osteoarthritis of the knee and bone marrow lesions.

As summarized in Table 5 and illustrated in FIG. 12, pain reduction was greater in patients with baseline VAS≥50 mm, greater still in patients with OARSI Grade 0 joint space narrowing, and greatest in patients with both baseline VAS≥50 mm and OARSI Grade 0 joint space narrowing.

TABLE 5

Pain Reduction Compared to Placebo at Three Months (mm)

| | VAS Change |
|---|---|
| All patients | −4.8 |
| Baseline VAS ≥50 mm | −9.0 |
| OARSI Grade 0 | −15.0 |
| Baseline VAS ≥50 mm + OARSI Grade 0 | −19.4 |

BMLs were evaluated using proton density-weighted fat saturation MR images. BMLs were scored using Osiris software (University of Geneva, Geneva, Switzerland). The maximum size was measured in $mm^2$ using software cursors applied to the greatest area of each lesion. The lesion with the highest score was used if more than one was present at the same site. Each patient was given a BML score ($mm^2$) at each of the four sites (medial tibial, medial femoral, lateral tibial, and lateral femoral sites) and these were summed to create a total BML score (mm²). The change in the total area of BMLs from baseline to 6 months was calculated.

Figure 13:
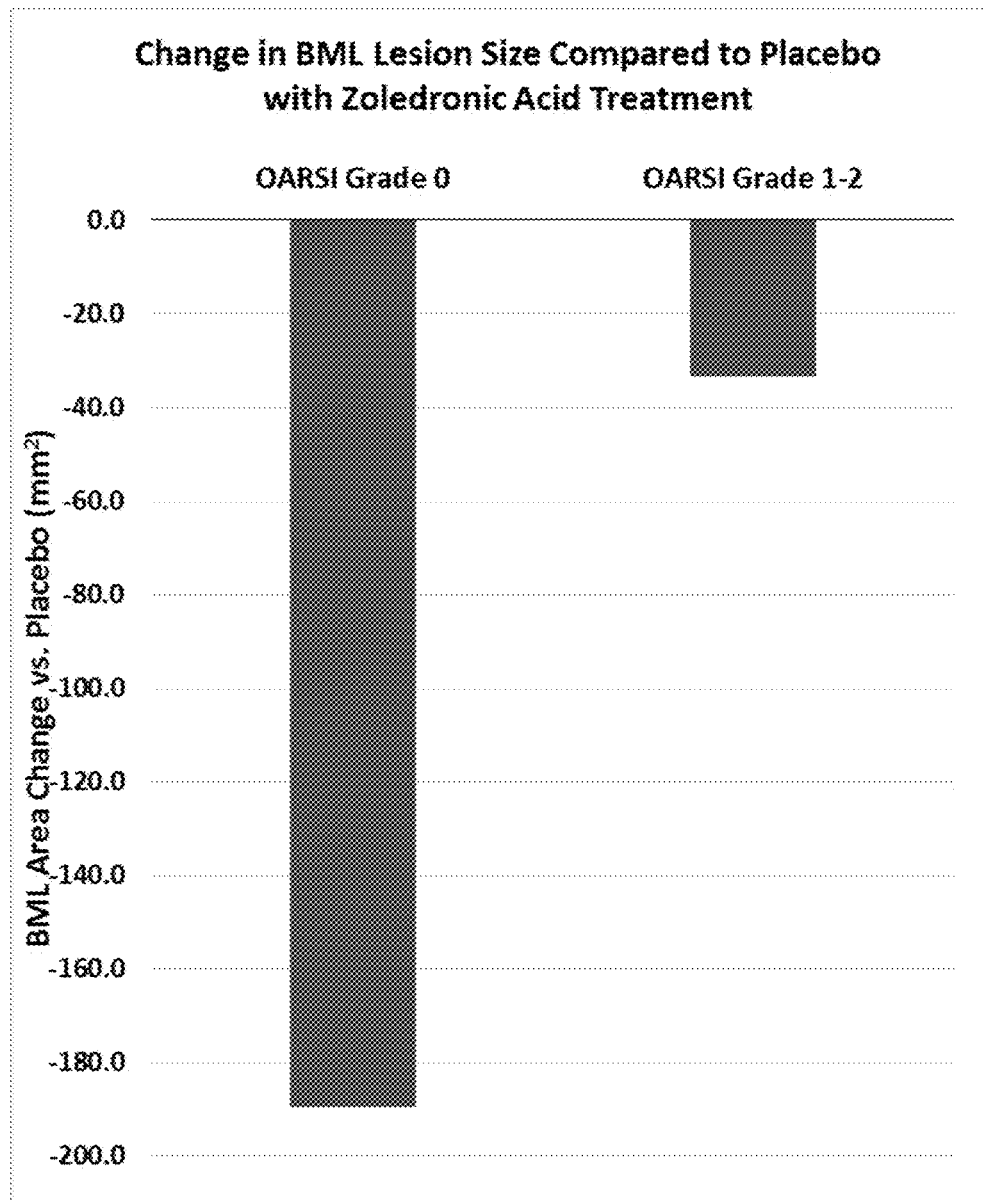
FIG. 13 depicts the change in BML lesion size compared to placebo at six months with zoledronic acid treatment in patients with osteoarthritis of the knee, bone marrow lesions, and different degrees of joint space narrowing.

The size of BMLs was reduced with zoledronic acid treatment. As shown in FIG. 13 and Table 6, average BML area decreased by approximately 190 mm² as compared to placebo in the OARSI Grade 0 group, but only by approximately 33 mm² as compared to placebo in patients with OARSI Grades 1-2.

TABLE 6

Change in BML Size (mm²)

|  | OARSI Grade 0 | OARSI Grades 1-2 |
|---|---|---|
| Zoledronic Acid | −244 | −117 |
| Placebo | −55 | −84 |
| Difference from Placebo | −190 | −33 |

Example 8

Methods

A study was performed to evaluate the efficacy of a single intravenous infusion of 5 mg ZA in comparison with intravenous placebo infusion among patients with chronic low back pain (LBP) and Modic changes on MRI. This study was a double-blinded, randomized, placebo-controlled clinical trial in patients with low back pain (LBP). Patients were included in the study if they had low back symptoms for at least three months, a LBP of at least six (6) on a 10-cm Visual Analog Scale (VAS) or an Oswestry Disability Index (ODI) of at least 30%, and an M1, mixed M1/2 or M2 type change on MRI performed within six months at most prior to enrolment.

Patients were excluded from the study if they had renal impairment with reduced creatinine clearance defined as an estimated glomerular filtration rate (eGFR) below ml/min, hypocalcemia, known hypersensitivity to zoledronic acid or other bisphosphonates or ingredients of the infusion product, the presence of red flags, nerve root entrapment or willingness for early retirement. Premenopausal women of childbearing potential were also excluded. Blood samples were taken prior to the infusion to assess the serum concentration of calcium and creatinine. The clinical examination included medical history and clinical assessment of lumbar flexibility, tendon signs, and motor and sensory testing.

After confirmation of eligibility patients were randomized to receive a single intravenous infusion of 5 mg zoledronic acid (n=20) or 100 ml saline as placebo (n=20) over a 15-minute period. Information on use of the concomitant medication and hospital admissions were recorded. Blood samples were taken for the assessment of safety, inflammatory mediators and markers of bone turnover at baseline, one month and one year.

Clinical assessments were performed 14 days before enrolment (screening visit), and follow-up visits at one month and one year after the infusion. The primary outcome was the change in the intensity of LBP on VAS. Secondary outcomes included leg pain intensity, ODI, health-related quality of life assessed with RAND-36, patient-reported sick leaves and lumbar flexibility. These outcome measures were assessed at baseline and at each follow-up. Lumbar flexibility was evaluated using the fingers-to-floor and trunk side bending measures (in cm). The percentage of patients undergoing a 20% relative improvement, the proportion of patients reaching a VAS score of 40 or less in the primary outcome, and patient acceptable symptom state (PASS) were also assessed. Pain medication use was inquired about during the follow-up visits.

Results

Zoledronic acid treatment resulted in a greater improvement in LBP intensity at one month as compared to placebo treatment. Furthermore, the patients receiving zoledronic acid reported NSAID use at one year significantly less often than those in the placebo group. Overall, the improvements in most of the evaluated parameters were greater in the zoledronic acid group throughout the follow-up period.

The clinical characteristics of study participants at baseline are displayed in Table 6. The mean LBP duration was 293 days, initial LBP intensity on VAS 6.7, leg pain on VAS 2.9 and the ODI score was 32%. Altogether 19 patients in the ZA group and 18 in the placebo group had a M1/2 lesion. Modic changes were most commonly (70%) situated at L4/5 or L5/S1. The zoledronic acid and placebo groups were similar as regards the demographic and background characteristics of all patients at baseline (Table 6).

The mean difference (MD) between the treatment groups in the primary outcome, intensity of LBP, significantly favored zoledronic acid at one month (MD 1.4; 95% CI 0.01 to 2.9) while at one year no significant difference was observed (MD 0.7; 95% CI −1.0 to 2.4; Table 7). The proportion of patients with at least 20% improvement in intensity of LBP and PASS both favored the zoledronic acid treatment at one month: zoledronic acid 55% vs. placebo 25% (p=0.105) and zoledronic acid 50% vs. placebo 20% (p=0.096), respectively.

For the patients who were treated with zoledronic acid, the reduction in pain intensity was greater in those with greater baseline pain intensity as shown in Table 9. The mean reduction in pain from baseline was 3.4 for patients with baseline pain intensity≥7, as compared to a reduction of only 0.1 for patients with a baseline pain intensity<6.

Of the secondary outcomes, the improvement in ODI, favored zoledronic acid at 1 month, the adjusted between-group difference being 6.0% (95% CI −0.6 to 13), but not at one year (Table 7). Similarly, side bending (to right and left) favored the zoledronic acid treatment at one month but not at one year (Table 7). Changes in total RAND-36, and in the physical and mental components of RAND-36 are shown in Table 8.

At baseline, there were no differences in self-reported use of non-steroidal anti-inflammatory drugs (NSAIDs) between the treatment groups, whereas at one year, only 20% of patients in the ZA group used NSAIDs versus 60% in the placebo group.

TABLE 6

Baseline characteristics of study population according to treatment group

| Characteristics | Zoledronic Acid n = 20 | Pacebo n = 20 |
|---|---|---|
| Sex, n (%) men | 15 (75) | 11 (55) |
| Age, mean (SD) years | 49 (9.3) | 51 (7.3) |

TABLE 6-continued

Baseline characteristics of study population according to treatment group

| Characteristics | Zoledronic Acid n = 20 | Pacebo n = 20 |
|---|---|---|
| Smoking, n (%) regular smokers* | 5 (25) | 6 (30) |
| BMI, mean (SD) kg/m | 26 (3.3) | 27 (3.2) |
| Workload, n (%) | | |
| Sedentary work with limited walking | 4 (20) | 4 (22) |
| Fairly light work with considerable walking but no lifting or carrying heavy objects | 4 (20) | 3 (17) |
| Fairly strenuous work with walking and lifting heaving objects or climbing stairs or uphill | 8 (40) | 6 (33) |
| Very strenuous work with lifting or carrying heaving objects such as shoveling, digging, or hammering | 4 (20) | 5 (28) |
| Type of worst MC-lesion**, n | | |
| Type I | 1 | 1 |
| Type I/II | 19 | 18 |
| Type II | 0 | 1 |
| MC at two or more levels, n (%) | 7 (3.5) | 4 (20) |
| Levels of MC, n | | |
| L2/3 | 4 | 0 |
| L3/4 | 3 | 5 |
| L4/5 | 6 | 5 |
| L5/S1 | 7 | 10 |
| Duration of LBP, median (IQ range) days | 330 (200, 365) | 315 (270, 365) |
| Intensity of LBP, mean (SD)*** | 6.6 (1.4) | 6.8 (1.6) |
| Duration of leg pain, median (IQ range) days | 50 (0, 100) | 36 (0, 160) |
| Intensity of leg pain, mean (SD)*** | 3.0 (3.1) | 2.9 (2.3) |
| Oswestry Disability Index, %, Mean (SD) | 30 (11) | 35 (10) |
| Duration of sick leave during the past year, median (IQ range) days | 14 (0, 48) | 18 (1, 181) |
| RAND-36, mean (SD) | 50 (8) | 50 (7) |
| RAND-36 physical component, mean (SD) | 51 (8) | 49 (8) |
| RAND-36 mental component, mean (SD) | 51 (8) | 49 (9) |

BMI = Body Mass Index,
MC = Modic Change,
LBP = low back pain,
SD = standard deviation,
IQ = inter-quartile.
*Smoking at least one cigarette per day.
**If different types of MC at two or more levels, classification is based on the assumed severity of the type, i.e., Type I > mixed Type I/II > Type II.
***Assessed using a 10 cm Visual Analogue Scale (VAS).

TABLE 7

Low back symptoms and lumbar flexibility at baseline, one month and 12 months according to treatment group and between group comparisons of difference from baseline to one month and 12 months

| | Mean (SD) original values | | Mean (SD) change | | Unadjusted analyses | | Adjusted analyses | |
|---|---|---|---|---|---|---|---|---|
| | ZA n = 20 | Placebo n = 20 | ZA | Placebo | Difference (95% CI) | P | Difference (95% CI) | P* |
| Intensity of LBP | | | | | | | | |
| Baseline | 6.6 (1.4) | 6.8 (1.6) | | | | | | |
| 1 mo. | 4.3 (2.3) | 5.8 (2.2) | −2.2 (2.7) | −0.9 (2.1) | 1.3 (−0.2 to 2.8) | 0.097 | 1.4 (0.01 to 2.9) | 0.049 |
| 12 mos. | 3.8 (2.5) | 4.6 (2.9) | −2.8 (2.9) | −2.2 (2.5) | 0.6 (−1.1 to 2.4) | 0.474 | 0.7 (−1.0 to 2.4) | 0.387 |
| Intensity of leg pain$^a$ | | | | | | | | |
| Baseline | 3.0 (3.1) | 2.9 (2.3) | | | | | | |
| 1 mo. | 2.0 (2.3) | 3.0 (2.4) | −0.6 (2.4) | 0.1 (2.6) | 0.8 (−0.9 to 2.4) | 0.367 | 0.8 (−0.6 to 2.2) | 0.237 |
| 12 mos. | 2.1 (2.8) | 2.7 (2.6) | −0.9 (3.4) | −0.3 (3.0) | 0.6 (−1.5 to 2.7) | 0.573 | 0.5 (−1.3 to 2.2) | 0.573 |
| Oswestry disability index, % | | | | | | | | |
| Baseline | 30 (11) | 35 (10) | | | | | | |
| 1 mo. | 24 (10) | 33 (13) | −5.9 (11) | −1.7 (9.7) | 4.3 (−2.5 to 11) | 0.212 | 6.0 (−0.6 to 13) | 0.071 |
| 12 mos. | 25 (13) | 33 (15) | −5.0 (15) | −1.9 (12) | 3.1 (−5.6 to 12) | 0.475 | 5.1 (−3.4 to 14) | 0.231 |

TABLE 7-continued

Low back symptoms and lumbar flexibility at baseline, one month and 12 months according to treatment group and between group comparisons of difference from baseline to one month and 12 months

| | Mean (SD) original values | | Mean (SD) change | | Unadjusted analyses | | Adjusted analyses | |
|---|---|---|---|---|---|---|---|---|
| | ZA n = 20 | Placebo n = 20 | ZA | Placebo | Difference (95% CI) | P | Difference (95% CI) | P* |
| Fingers-to-floor, cm | | | | | | | | |
| Baseline | 23 (19) | 19 (18) | | | | | | |
| 1 mo. | 17 (17) | 19 (17) | −5.1 (20) | −0.1 (8.3) | 5.0 (−4.8 to 15) | 0.306 | 3.6 (−5.0 to 12) | 0.403 |
| 12 mos. | 16 (16) | 20 (19) | −6.3 (23) | 0.9 (11) | 7.1 (−4.3 to 18) | 0.215 | 5.3 (−4.5 to 15) | 0.277 |
| Sidebending to right, cm | | | | | | | | |
| Baseline | 14.1 (4.9) | 13.8 (7.2) | | | | | | |
| 1 mo. | 15.7 (5.9) | 13.3 (6.9) | 1.5 (4.7) | −0.5 (2.2) | −2.0 (−4.3 to 0.4) | 0.101 | −2.0 (−4.4 to 0.3) | 0.087 |
| 12 mos. | 15.7 (5.6) | 13.8 (6.5) | 1.6 (4.8) | −0.1 (3.5) | −1.6 (−4.3 to 1.1) | 0.227 | −1.7 (−4.2 to 0.8) | 0.180 |
| Sidebending to left, cm | | | | | | | | |
| Baseline | 15.0 (5.4) | 13.3 (5.5) | | | | | | |
| 1 mo. | 16.1 (5.3) | 12.8 (5.9) | 1.1 (3.0) | −0.5 (2.2) | −1.5 (−3.2 to 0.1) | 0.072 | −1.7 (−3.4 to 0.0) | 0.051 |
| 12 mos. | 16.2 (6.7) | 13.7 (5.7) | 1.2 (5.3) | 0.5 (3.2) | −0.7 (−3.5 to 2.1) | 0.601 | −1.0 (−3.8 to 1.8) | 0.458 |

SD = standard deviation,
CI = confidence interval,
ZA = zoledronic acid,
LBP = low back pain.
*ANCOVA: Difference between follow-up and baseline, treatment effect adjusted for baseline value.
$^a$One subject missing at baseline in placebo group and in ZA group, and one subject at 1 month in ZA group.

TABLE 8

Health-related quality of life assessed using RAND-36 at baseline, one month, and 12 months according to treatment group and between group comparisons of difference from baseline to one month and 12 months

| | Mean (SD) original values | | Mean (SD) change | | Unadjusted analyses | | Adjusted analyses | |
|---|---|---|---|---|---|---|---|---|
| | ZA n = 20 | Placebo n = 20 | ZA | Placebo | Difference (95% CI) | P | Difference (95% CI) | P* |
| Total RAND-36 | | | | | | | | |
| Baseline | 50 (8) | 50 (7) | | | | | | |
| 1 mo. | 51 (8) | 49 (8) | 0.6 (6.4) | −0.6 (5.0) | 1.2 (−3 to 5) | 0.530 | 1.3 (−3 to 5) | 0.477 |
| 12 mos. | 51 (8) | 49 (9) | 1.0 (8.7) | −1.0 (5.9) | 2.1 (−3 to 7) | 0.378 | 2.2 (−2 to 7) | 0.314 |
| Physical component | | | | | | | | |
| Baseline | 52 (8) | 48 (8) | | | | | | |
| 1 mo. | 52 (9) | 48 (8) | 0.1 (8.6) | −0.1 (5.5) | 0.3 (−4 to 5) | 0.897 | 1.3 (−3 to 6) | 0.554 |
| 12 mos. | 52 (8) | 48 (2) | 0.3 (10) | −0.3 (6.5) | 0.7 (−5 to 6) | 0.808 | 2.1 (−3 to 7) | 0.405 |
| Mental component | | | | | | | | |
| Baseline | 49 (9) | 51 (8) | | | | | | |
| 1 mo. | 50 (9) | 50 (9) | 1.0 (6.1) | −1.0 (5.6) | 2.0 (−2 to 6) | 0.286 | 1.6 (−2 to 5) | 0.396 |
| 12 mos. | 51 (9) | 49 (9) | 1.8 (9.0) | −1.8 (6.7) | 3.5 (−2 to 9) | 0.167 | 2.7 (−2 to 7) | 0.261 |

SD = standard deviation,
CI = confidence interval,
ZA = zoledronic acid.
*ANCOVA: Difference between follow-up and baseline, treatment effect adjusted for baseline value.

TABLE 9

Pain Reduction in Patients Treated Zoledronic Acid (cm)

| | VAS Change from Baseline |
|---|---|
| Baseline VAS <6 | −0.1 |
| Baseline VAS ≥6 and <7 | −2.3 |
| Baseline VAS ≥7 | −3.4 |

Example 9

Methods:

A study was performed to evaluate the efficacy of bisphosphonates such as oral zoledronic acid in inhibiting immune responses and pain behavior in a rat fracture model of CRPS.

The effect of orally administered zoledronic acid was examined in the rat tibia fracture model of complex regional pain syndrome (CRPS). CRPS was induced in the rats by fracturing the right distal tibias of the animals and casting the fractured hindpaws for 4 weeks, as described in Guo T Z et al. (Pain. 2004; 108: 95-107). This animal model has been shown to replicate the inciting trauma (such as a fracture, a surgery, a crushing injury, a cutting injury, a scratch, or a puncture injury), natural history, signs, symptoms, and pathologic changes observed in human CRPS patients (Kingery W S et al., Pain. 2003; 104:75-84).

Figure 16:
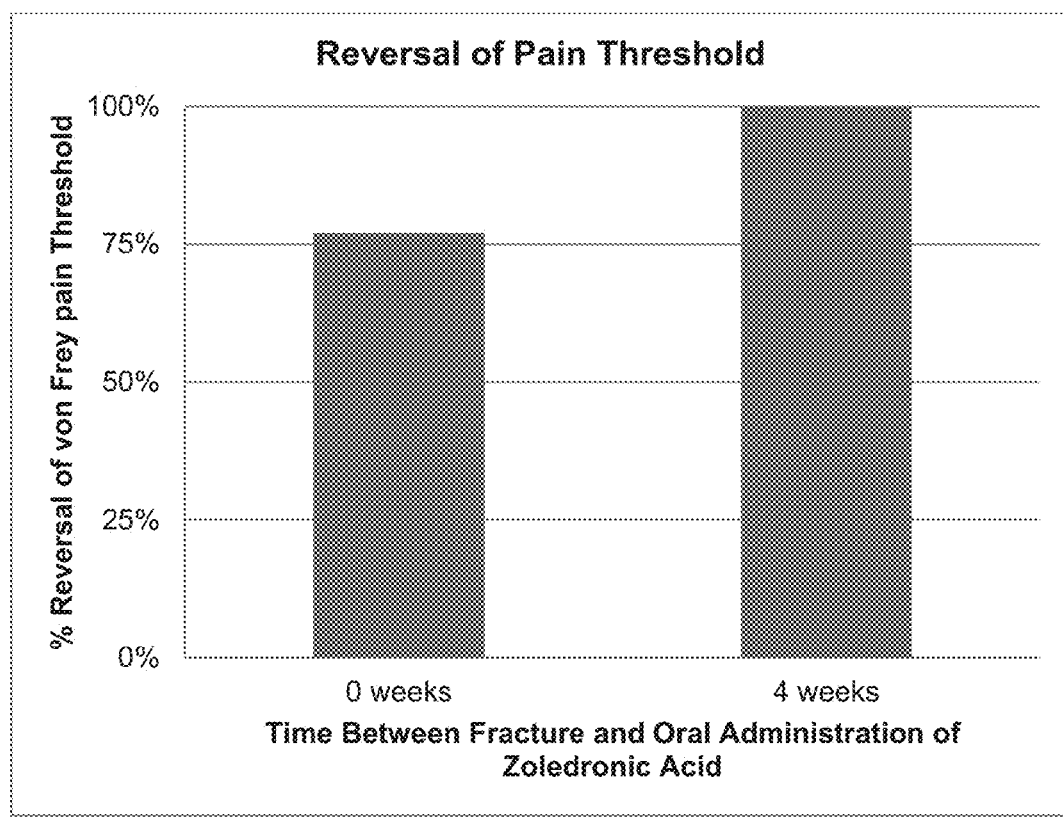
FIG. 16 depicts hindpaw pain thresholds for rats administered zoledronic acid at the time of fracture as compared to rats administered zoledronic acid four weeks after fracture.

As can be seen in FIG. 16, orally administering zoledronic acid four weeks after the fracture resulted in significantly greater improvement of pain relief as compared to administration at the time of injury.

Example 10

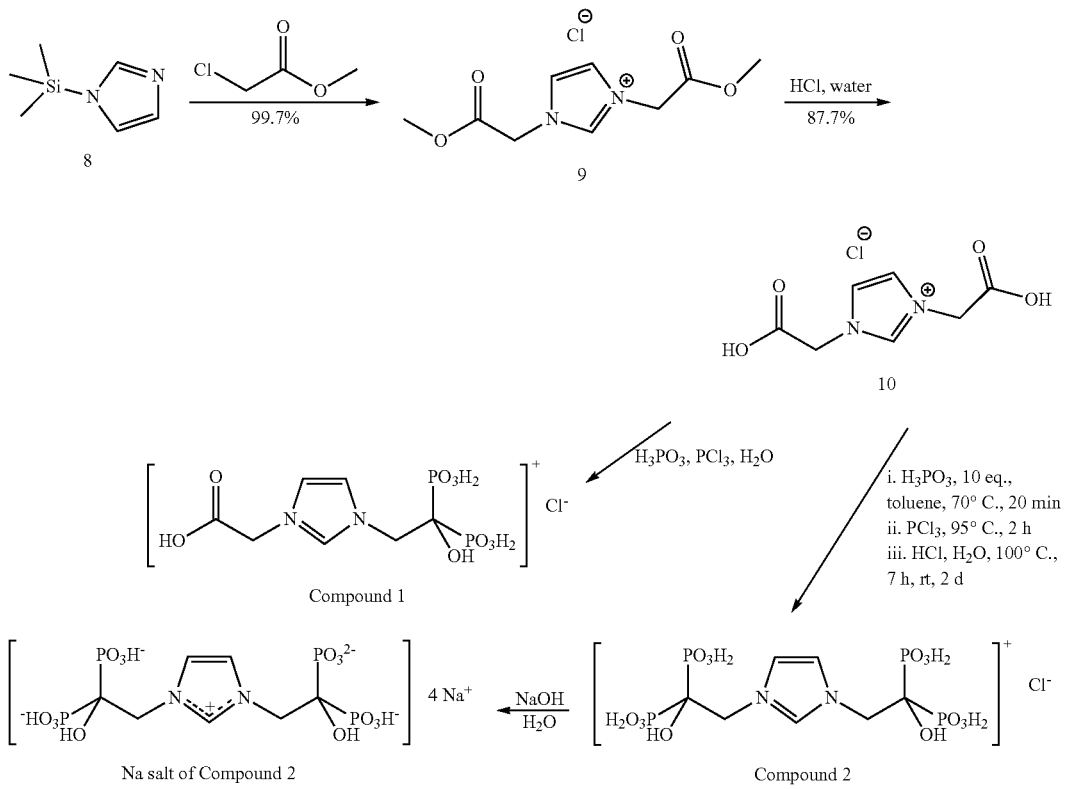

Starting four weeks after fracture and casting, animals were orally administered either vehicle (control) or zoledronic acid, a dose of 21 mg/kg on the first day and 3 mg/kg/day daily thereafter, or distilled water for 3 weeks (weeks 4-7 post-fracture). Drug was dissolved in distilled water and administered by gavage. Animals were fasted for 4 hours before and 2 hours after dosing. At the end of the 21-day period, casts were removed, and on the following day, the rats were tested for hindpaw pain, edema, and warmth.

Results

Figure 14:
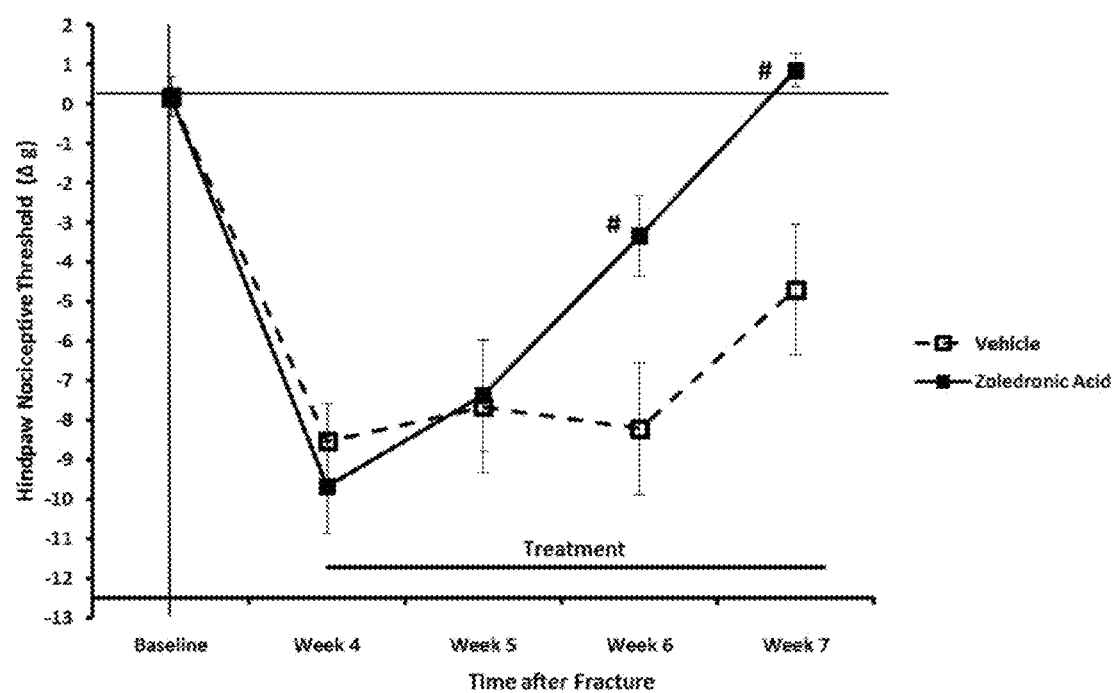
FIG. 14 depicts hindpaw pain thresholds for vehicle and zoledronic acid treated rats in a rat model of complex regional pain syndrome.
Figure 15:
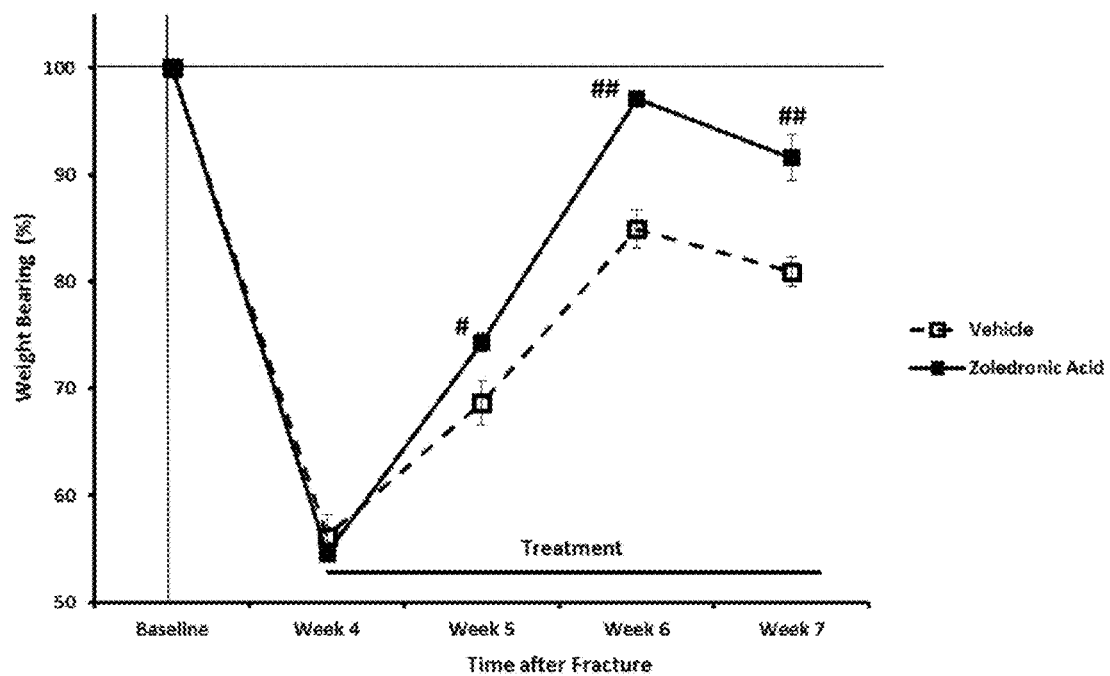
FIG. 15 depicts weight bearing for vehicle and zoledronic acid treated rats in a rat model of complex regional pain syndrome.

As illustrated in FIGS. 14-15, treatment with orally administered zoledronic acid reversed pain and restored weight bearing as compared to the vehicle treated animals.

As illustrated in FIG. 14, von Frey pain thresholds for the right (fracture) hindpaw were reduced by over 100% as compared to baseline when oral zoledronic acid was administered.

As illustrated in FIG. 15, reduction in weight bearing, a postural effect of pain, was significantly higher in the vehicle treated group as compared to the zoledronic acid treated group. Weight bearing on the fracture hindlimb was reduced to about 80% of normal in the vehicle treated group. Zoledronate treatment significantly restored hindlimb weight bearing as compared to vehicle treatment (over 90% of normal).

1,3-Bis(2-methoxy-2-oxoethyl)-1H-imidazol-3-ium chloride (9)

Methyl chloroacetate (29.8 mL, 338.6 mmol, 2.0 eq) was added drop-wise to 1-(trimethylsilyl)-1H-imidazole (8; 25.0 mL, 169.3 mmol). The mixture was heated at 60° C. for 24 hours. The mixture was cooled to room temperature, washed with Et$_2$O (3×500 mL) and dried in vacuo yielding 9 (41.97 g, 168.8 mmol, 99.7%) as a white solid.

1,3-Bis(carboxymethyl)-1H-imidazol-3-ium chloride (10)

To 1,3-bis(2-methoxy-2-oxoethyl)-1H-imidazol-3-ium chloride (9; 41.00 g, 164.88 mmol, 1 eq.) was added 37% aq. HCl (30.03 mL, 362.74 mmol, 2.2 eq.). The mixture was stirred under reflux for 0.5 hour. The mixture was concentrated and the remaining solid was washed with acetone (2×200 mL) and Et$_2$O (3×200 mL). Drying in vacuo gave 10 (31.89 g, 144.55 mmol, 87.7%) as a white solid.

Compound 1:

Compound 10 is reacted with an equimolar amount of phosphorous acid, followed by an equimolar amount of phosphorous trichloride, and an excess of water to form Compound 1, which is precipitated from ethanol.

Compound 2:

1,3-Bis(carboxymethyl)-1H-imidazol-3-ium chloride (10, 2.00 g, 9 mmol, 1.0 eq) and $H_3PO_3$ (7.37 g, 90 mmol, 10 eq) were dissolved in toluene (10 mL) and heated to 70° C. The reaction mixture was stirred at this temperature for 20 min before $PCl_3$ (16 mL, 180 mmol, 20 eq) was added within 30 min. The reaction mixture was then heated to 95° C. and stirred at this temperature for 2 h. Then, aq. HCl (30 mL, 37% HCl and 5 mL $H_2O$) was added. The reaction mixture was heated to 100° C. and stirred at this temperature for 7 h, then stirred at room temperature for 2 days and filtered. The filtrate was cooled in an ice bath and added within 45 min to absolute EtOH (90 mL). The resulting turbid solution was stirred for 1 h at room temperature before the solid was filtered off. The filter cake (Compound 2) was isolated and analyzed by 2D-NMR spectroscopy and mass spectrometry (m/z=477). The filtrate was concentrated in vacuo to give a residue. This residue (500 mg) was treated with aq. NaOH (150 mg in 3.5 mL of $H_2O$) and EtOH (7 mL). After standing overnight the liquid was decanted and the resulting solid (Na salt of Compound 2) was obtained and analyzed by NMR and mass spectrometry (m/z=477).

The following embodiments are specifically contemplated:

Embodiment 1

A method of relieving inflammatory pain comprising administering an oral dosage form containing zoledronic acid to a mammal in need thereof, wherein the mammal receives a total monthly dose of zoledronic acid that is about 800 mg/m² or less based upon the body surface area of the mammal.

Embodiment 2

The method of embodiment 1, wherein the mammal is a human being that receives a total monthly dose of zoledronic acid that is about 30 mg/m² to about 700 mg/m².

Embodiment 3

The method of embodiment 2, wherein the total monthly dose is administered in 4 or 5 weekly doses.

Embodiment 4

The method of embodiment 2, wherein the total monthly dose is administered in 28 to 31 daily doses.

Embodiment 5

The method of embodiment 2, wherein the total monthly dose is administered in 5 to 10 individual doses during the month.

Embodiment 6

The method of embodiment 1, wherein the mammal is a human being that receives a total weekly dose of zoledronic acid that is about 10 mg to about 300 mg.

Embodiment 7

The method of embodiment 6, wherein the total weekly dose is a single dose, administered once a week.

Embodiment 8

The method of embodiment 6, wherein the total weekly dose is administered in 2 to 7 individual doses during the week.

Embodiment 9

The method of embodiment 1, wherein the mammal is a human being that receives a total weekly dose of zoledronic acid that is about 10 mg to about 150 mg.

Embodiment 10

The method of any preceding embodiment, wherein the mammal experiences significant pain relief more than 3 hours after administration of the dosage form.

Embodiment 11

The method of embodiment 10, wherein the mammal experiences significant pain relief during at least a part of a time from about 3 hours to about 24 hours after administration of the dosage form.

Embodiment 12

The method of embodiment 10, wherein the mammal experiences significant pain relief during at least a part of a time from about 3 hours to about 3 weeks after administration of the dosage form.

Embodiment 13

A method of relieving inflammatory pain comprising administering an oral dosage form containing zoledronic acid to a mammal in need thereof, wherein the oral dosage form contains about 10 mg/m² to about 20 mg/m² of zoledronic acid based upon the body surface area of the mammal.

Embodiment 14

The method of embodiment 13, wherein the oral dosage form contains about 15 mg/m² to about 20 mg/m² of zoledronic acid based upon the body surface area of the mammal.

Embodiment 15

A method of relieving inflammatory pain comprising orally administering to a mammal in need thereof, about 300 mg/m² to about 600 mg/m² of zoledronic acid per month to the mammal, based upon the body surface area of the mammal.

Embodiment 16

The method of embodiment 15, comprising orally administering about 450 mg/m² to about 600 mg/m² of zoledronic acid per month to the mammal, based upon the body surface area of the mammal.

Embodiment 17

The method of any preceding embodiment, wherein the mammal is not suffering from bone metastasis.

Embodiment 18

The method of any preceding embodiment, wherein the mammal is not suffering from cancer.

Embodiment 19

The method of any preceding embodiment, wherein the zoledronic acid is administered as a salt of a dianion of zoledronic acid.

Embodiment 20

A method of relieving pain associated with an arthritis comprising administering an oral dosage form containing zoledronic acid to a human being in need thereof.

Embodiment 21

The method of embodiment 20, wherein the human being receives a total monthly dose of zoledronic acid that is about 40 mg to about 2000 mg.

Embodiment 22

The method of embodiment 21, wherein the total monthly dose is administered in 4 or 5 weekly doses.

Embodiment 23

The method of embodiment 21, wherein the total monthly dose is administered in 28 to 31 daily doses.

Embodiment 24

The method of embodiment 21, wherein the total monthly dose is administered in 5 to 10 individual doses during the month.

Embodiment 25

The method of embodiment 20, wherein the human being receives a total weekly dose of zoledronic acid that is about 100 mg to about 300 mg.

Embodiment 26

The method of embodiment 25, wherein the total weekly dose is a single dose, administered once a week.

Embodiment 27

The method of embodiment 25, wherein the total weekly dose is administered in 2 to 7 individual doses during the week.

Embodiment 28

The method of embodiment 20, wherein the human being receives a total weekly dose of zoledronic acid that is about 10 mg to about 100 mg.

Embodiment 29

The method of any of embodiments 20-28, wherein the human being experiences significant pain relief more than 3 hours after administration of the dosage form.

Embodiment 30

The method of embodiment 29, wherein the human being experiences significant pain relief during at least a part of a time from about 3 hours to about 24 hours after administration of the dosage form.

Embodiment 31

The method of embodiment 29, wherein the human being experiences significant pain relief during at least a part of a time from about 3 hours to about 3 weeks after administration of the dosage form.

Embodiment 32

The method of any of embodiments 20-31, wherein the dosage form contains about 10 mg/m$^2$ to about 20 mg/m$^2$ of zoledronic acid based upon the body surface area of the human being.

Embodiment 33

The method of embodiment 32, wherein the dosage form contains about 15 mg/m$^2$ to about 20 mg/m$^2$ of zoledronic acid based upon the body surface area of the human being.

Embodiment 34

The method of any of embodiments 20-33, wherein about 50 mg/m$^2$ to about 200 mg/m$^2$ of zoledronic acid is orally administered per month, based upon the body surface area of the human being.

Embodiment 35

The method of any of embodiments 20-31, wherein the dosage form contains about 80 mg/m$^2$ to about 150 mg/m$^2$ of zoledronic acid based upon the body surface area of the human being.

Embodiment 36

The method of embodiment 35, wherein about 300 mg/m$^2$ to about 1000 mg/m$^2$ of zoledronic acid is orally administered per month, based upon the body surface area of the human being.

Embodiment 37

The method of any of embodiments 20-36, wherein the human being is not suffering from bone metastasis.

Embodiment 38

The method of any of embodiments 20-37, wherein the human being is not suffering from cancer.

Embodiment 39

The method of any preceding embodiment, wherein the zoledronic acid is in the disodium salt form.

Embodiment 40

An oral dosage form comprising zoledronic acid, wherein the oral bioavailability of zoledronic acid in the dosage form is about 0.01% to about 4%.

Embodiment 41

The oral dosage form of embodiment 40, wherein the oral dosage form contains about 10 mg to about 300 mg of zoledronic acid.

Embodiment 42

The oral dosage form of embodiment 40, wherein the oral dosage form contains about 10 mg to about 50 mg of zoledronic acid.

Embodiment 43

The oral dosage form of any of embodiments 40-42, wherein the oral bioavailability of zoledronic acid in the dosage form is about 0.1% to about 2%.

Embodiment 44

A pharmaceutical product comprising more than one unit of an oral dosage form of embodiment 40.

Embodiment 45

The pharmaceutical product of embodiment 44, wherein each unit of the oral dosage form contains about 1 mg to about 50 mg of zoledronic acid.

Embodiment 46

The pharmaceutical product of embodiment 45, comprising 28, 29, 30, or 31 units of the oral dosage form, for a total of about 28 mg to about 1600 mg of zoledronic acid to be administered in about 1 month.

Embodiment 47

The pharmaceutical product of embodiment 45, comprising 85 to 95 units of the oral dosage form, for a total of about 85 mg to about 4800 mg of zoledronic acid to be administered in about 3 months.

Embodiment 48

The pharmaceutical product of embodiment 45, comprising 170 to 200 units of the oral dosage form, for a total of about 170 mg to about 10,000 mg of zoledronic acid to be administered in about 6 months.

Embodiment 49

The pharmaceutical product of embodiment 45, comprising 350 to 380 units of the oral dosage form, for a total of about 350 mg to about 19,000 mg of zoledronic acid to be administered in about 1 year.

Embodiment 50

The pharmaceutical product of embodiment 44, wherein each unit of the oral dosage form contains about 10 mg to about 300 mg.

Embodiment 51

The pharmaceutical product of embodiment 50, comprising 4 or 5 units of the oral dosage form, for a total of about 40 mg to about 1500 mg of zoledronic acid to be administered within a period of about 1 month.

Embodiment 52

The pharmaceutical product of embodiment 50, comprising 8 or 9 units of the oral dosage form, for a total of about 80 mg to about 2700 mg of zoledronic acid to be administered in about 2 months.

Embodiment 53

The pharmaceutical product of embodiment 50, comprising 12, 13 or 14 units of the oral dosage form, for a total of about 120 mg to about 4200 mg of zoledronic acid to be administered in about 3 months.

Embodiment 54

The pharmaceutical product of embodiment 50, comprising 22 to 30 units of the oral dosage form, for a total of about 220 mg to about 9000 mg of zoledronic acid to be administered in about 6 months.

Embodiment 55

The pharmaceutical product of embodiment 50, comprising 45 to 60 units of the oral dosage form, for a total of about 450 mg to about 18000 mg of zoledronic acid to be administered in about 1 year.

Embodiment 56

The pharmaceutical product of embodiment 44, comprising 1 to 10 units of the oral dosage form, wherein the product contains about 200 mg to about 2000 mg of zoledronic acid.

Embodiment 57

The oral dosage form of any preceding embodiment, wherein the zoledronic acid is in the form of a sodium salt.

Embodiment 58

The oral dosage form of any preceding embodiment, wherein the zoledronic acid is in a form that has an aqueous solubility greater than 1% (w/v).

Embodiment 59

The oral dosage form of any preceding embodiment, wherein the zoledronic acid is in a form that has an aqueous solubility of about 5% (w/v) to about 50% (w/v).

Embodiment 60

An oral dosage form comprising zoledronic acid and an excipient, wherein the zoledronic acid is in a form that has an aqueous solubility greater than 1% (w/v).

Embodiment 61

The oral dosage form of embodiment 60, wherein the zoledronic acid is in a form that has an aqueous solubility of about 5% (w/v) to about 50% (w/v).

Embodiment 62

A method of treating complex regional pain syndrome comprising administering an oral dosage form containing zoledronic acid to a mammal in need thereof.

Embodiment 63

The method of embodiment 62, wherein the mammal is a human being that receives an amount of zoledronic acid that is about 30 mg/m² to about 700 mg/m² in a period of one month or less.

Embodiment 64

The method of embodiment 63, wherein 4 or 5 weekly doses are administered in a period of one month or less.

Embodiment 65

The method of embodiment 63, wherein 28 to 31 daily doses are administered in a period of one month or less.

Embodiment 66

The method of embodiment 63, wherein 5 to 10 individual doses are administered during a period of one month or less.

Embodiment 67

The method of embodiment 63, wherein about 30 mg/m² to about 700 mg/m² of zoledronic acid is administered during only one month.

Embodiment 68

The method of embodiment 63, wherein about 30 mg/m² to about 700 mg/m² of zoledronic acid is administered in a period of one month or less for 2 or more consecutive months.

Embodiment 69

The method of embodiment 62, wherein the mammal receives about 10 mg/m² to about 30 mg/m² of zoledronic acid daily.

Embodiment 70

The method of embodiment 62, wherein the mammal is a human being that receives a total weekly dose of zoledronic acid that is about 10 mg to about 300 mg.

Embodiment 71

The method of embodiment 70, wherein the total weekly dose is a single dose, administered once a week.

Embodiment 72

The method of embodiment 70, wherein the total weekly dose is administered in 2 to 7 individual doses during the week.

Embodiment 73

The method of any of embodiments 62-72, wherein the complex regional pain syndrome is complex regional pain syndrome type I.

Embodiment 74

The method of any of embodiments 62-72, wherein the complex regional pain syndrome is complex regional pain syndrome type II.

Embodiment 75

The method of any preceding embodiment, wherein the zoledronic acid is in a salt form.

Embodiment 76

The method of any of embodiments 62-75, wherein the dosage form contains about 10 mg/m² to about 20 mg/m² of zoledronic acid based upon the body surface area of the mammal.

Embodiment 77

The method of embodiment 76, wherein the dosage form contains about 15 mg/m² to about 20 mg/m² of zoledronic acid based upon the body surface area of the mammal.

Embodiment 78

A method of treating complex regional pain syndrome, comprising administering pamidronic acid to a human being in need thereof.

Embodiment 79

A method of treating complex regional pain syndrome, comprising administering neridronic acid to a human being in need thereof.

Embodiment 80

A method of treating complex regional pain syndrome, comprising administering olpadronic acid to a human being in need thereof.

Embodiment 81

A method of treating complex regional pain syndrome, comprising administering alendronic acid to a human being in need thereof.

Embodiment 82

A method of treating complex regional pain syndrome, comprising administering incadronic acid to a human being in need thereof.

Embodiment 83

A method of treating complex regional pain syndrome, comprising administering ibandronic acid to a human being in need thereof.

Embodiment 84

A method of treating complex regional pain syndrome, comprising administering risedronic acid to a human being in need thereof.

Embodiment 85

A method of treating pain, comprising administering pamidronic acid to a human being in need thereof.

Embodiment 86

A method of treating pain, comprising administering neridronic acid to a human being in need thereof.

Embodiment 87

A method of treating pain, comprising administering olpadronic acid to a human being in need thereof.

Embodiment 88

A method of treating pain, comprising administering alendronic acid to a human being in need thereof.

Embodiment 89

A method of treating pain, comprising administering incadronic acid to a human being in need thereof.

Embodiment 90

A method of treating pain, comprising administering ibandronic acid to a human being in need thereof.

Embodiment 91

A method of treating pain, comprising administering risedronic acid to a human being in need thereof.

Embodiment 92

A method of treating arthritis pain, comprising administering pamidronic acid to a human being in need thereof.

Embodiment 93

A method of treating arthritis pain, comprising administering neridronic acid to a human being in need thereof.

Embodiment 94

A method of treating arthritis pain, comprising administering olpadronic acid to a human being in need thereof.

Embodiment 95

A method of treating arthritis pain, comprising administering alendronic acid to a human being in need thereof.

Embodiment 96

A method of treating arthritis pain, comprising administering incadronic acid to a human being in need thereof.

Embodiment 97

A method of treating arthritis pain, comprising administering ibandronic acid to a human being in need thereof.

Embodiment 98

A method of treating arthritis pain, comprising administering risedronic acid to a human being in need thereof.

Embodiment 99

A method of treating inflammatory pain, comprising administering pamidronic acid to a human being in need thereof.

Embodiment 100

A method of treating inflammatory pain, comprising administering neridronic acid to a human being in need thereof.

Embodiment 101

A method of treating inflammatory pain, comprising administering olpadronic acid to a human being in need thereof.

Embodiment 102

A method of treating inflammatory pain, comprising administering alendronic acid to a human being in need thereof.

Embodiment 103

A method of treating inflammatory pain, comprising administering incadronic acid to a human being in need thereof.

Embodiment 104

A method of treating inflammatory pain, comprising administering ibandronic acid to a human being in need thereof.

Embodiment 105

A method of treating inflammatory pain, comprising administering risedronic acid to a human being in need thereof.

Embodiment 106

A method of treating complex regional pain syndrome, comprising administering etidronic acid to a human being in need thereof.

Embodiment 107

A method of treating pain, comprising administering etidronic acid to a human being in need thereof.

Embodiment 108

A method of treating arthritis pain, comprising administering etidronic acid to a human being in need thereof.

Embodiment 109

A method of treating inflammatory pain, comprising administering etidronic acid to a human being in need thereof.

Embodiment 110

A method of treating complex regional pain syndrome, comprising administering clodronic acid to a human being in need thereof.

Embodiment 111

A method of treating pain, comprising administering clodronic acid to a human being in need thereof.

Embodiment 112

A method of treating arthritis pain, comprising administering clodronic acid to a human being in need thereof.

Embodiment 113

A method of treating inflammatory pain, comprising administering clodronic acid to a human being in need thereof.

Embodiment 114

A method of treating complex regional pain syndrome, comprising administering tiludronic acid to a human being in need thereof.

Embodiment 115

A method of treating pain, comprising administering tiludronic acid to a human being in need thereof.

Embodiment 116

A method of treating arthritis pain, comprising administering tiludronic acid to a human being in need thereof.

Embodiment 117

A method of treating inflammatory pain, comprising administering tiludronic acid to a human being in need thereof.

Embodiment 118

The method of any of embodiments 78-117, wherein the active compound is orally administered.

Embodiment 119

The method of any of embodiments 78-117, wherein the active compound is parenterally administered.

Embodiment 120

A method of enhancing the oral bioavailability of zoledronic acid comprising orally administering a dosage form containing zoledronic acid in the disodium salt form.

Embodiment 121

The method of embodiment 120, wherein the zoledronic acid in the disodium salt form provides an enhancement to bioavailability, as compared to zoledronic acid in the diacid form, which adds to any enhancement to bioavailability provided by any bioavailability-enhancing agents in the dosage form.

Embodiment 122

The method of embodiment 120, wherein the dosage form is substantially free of bioavailability-enhancing agents.

Embodiment 123

The method of embodiment 120, wherein the zoledronic acid in the disodium salt form is administered to a mammal in an amount that provides an area under the plasma concentration curve of zoledronic acid of about 4 ng·h/mL to about 2000 ng·h/mL to the mammal each time the zoledronic acid in the disodium salt is administered.

Embodiment 124

The method of embodiment 123, wherein the zoledronic acid in the disodium salt form is administered at an interval of about 3 to about 4 weeks in an amount that provides an area under the plasma concentration curve of zoledronic acid of about 100 ng·h/mL to about 2000 ng·h/mL to the mammal each time the zoledronic acid in the disodium salt form is administered.

Embodiment 125

The method of embodiment 123, wherein the zoledronic acid in the disodium salt form is administered weekly, or 3 to 5 times in a month, in an amount that provides an area under the plasma concentration curve of zoledronic acid of about 20 ng·h/mL to about 700 ng·h/mL to the mammal each time the zoledronic acid in the disodium salt form is administered.

Embodiment 126

The method of embodiment 123, wherein the zoledronic acid in the disodium salt form is administered daily in an amount that provides an area under the plasma concentration curve of zoledronic acid of about 4 ng·h/mL to about 100 ng·h/mL to the mammal each time the zoledronic acid in the disodium salt form is administered.

Embodiment 127

The method of embodiment 120, wherein the dosage form is a solid.

Embodiment 128

The method of embodiment 120, 121, 122, 123, 124, 125, 126, or 127, wherein the bioavailability of zoledronic acid is improved by at least about 20% as compared to administration of zoledronic acid in the diacid form.

Embodiment 129

The method of embodiment 120, 121, 122, 123, 124, 125, 126, 127, or 128, further comprising administering, on a molar basis, less of the zoledronic acid in the disodium salt form than would be administered of zoledronic acid in the diacid form in order to achieve the same plasma levels of zoledronic acid.

Embodiment 130

The method of embodiment 129, wherein at least about 10 mole % less of the disodium salt form is administered as compared the amount of zoledronic acid in the diacid form that would be administered in order to achieve the same plasma levels of zoledronic acid.

Embodiment 131

The method of embodiment 129, wherein the disodium salt form is administered in an amount, on a molar basis, that has a value of about $0.8n_d$ to about $1.2n_d$, wherein:

$n_d = (b_a/b_d)(n_a)$ wherein $b_a$ is the bioavailability of the diacid form, $b_d$ is the bioavailability of the disodium salt form, and $n_a$ is the number of moles of zoledronic acid in the diacid form that would be administered in order to achieve the same plasma levels of zoledronic acid.

Embodiment 132

The method of embodiment 131, wherein the disodium salt is administered in an amount that has a value of about $n_d$.

Embodiment 133

The method of any of embodiments 120-132, wherein the zoledronic acid is used to treat an inflammatory condition.

Embodiment 134

The method of embodiment 133, wherein the zoledronic acid is used to treat arthritis.

Embodiment 135

The method of embodiment 133, wherein the zoledronic acid is used to treat complex regional pain syndrome.

Embodiment 136

The method of any of embodiments 1-39, 62-77, and 120-135, wherein:
a first oral dosage form is administered; and
a second oral dosage form is administered;
wherein, with respect to the first oral dosage form, the second oral dosage form is administered at $10 \times T_{max}$ or greater, wherein $T_{max}$ is the time of maximum plasma concentration for the first oral dosage form.

Embodiment 137

A dosage form comprising zoledronic acid in the disodium salt form, wherein the bioavailability, in a mammal, of zoledronic acid in the disodium salt form is greater than the bioavailability of zoledronic acid in the diacid form would be in the same dosage form.

Embodiment 138

A dosage form comprising zoledronic acid in the disodium salt form, wherein the dosage form contains an amount of zoledronic acid in the disodium salt form that provides an area under the plasma concentration curve of zoledronic acid of about 4 ng·h/mL to about 2000 ng·h/mL to a human being to which the dosage form is administered.

Embodiment 139

The dosage form of embodiment 138, wherein the dosage form contains an amount of zoledronic acid in the disodium salt form that provides an area under the plasma concentration curve of zoledronic acid of about 100 ng·h/mL to about 2000 ng·h/mL to a human being to which the dosage form is administered.

Embodiment 140

The dosage form of embodiment 138, wherein the dosage form contains an amount of zoledronic acid in the disodium salt form that provides an area under the plasma concentration curve of zoledronic acid of about 20 ng·h/mL to about 700 ng·h/mL to a human being to which the dosage form is administered.

Embodiment 141

The dosage form of embodiment 138, wherein the dosage form contains an amount of zoledronic acid in the disodium salt form that provides an area under the plasma concentration curve of zoledronic acid of about 4 ng·h/mL to about 100 ng·h/mL to a human being to which the dosage form is administered.

Embodiment 142

A dosage form comprising zoledronic acid in the disodium salt form,
wherein the disodium salt form is present in a lower molar amount than would be present if the zoledronic acid were in the diacid form; and
wherein the zoledronic acid in the disodium salt form has an improved bioavailability as compared to the zoledronic acid in the diacid form to the extent that the lower molar amount of the disodium salt in the dosage form does not reduce the amount of zoledronic acid delivered to the plasma of a mammal.

Embodiment 143

The dosage form of embodiment 137, 138, 139, 140, 141, or 142, wherein the dosage form is a solid.

Embodiment 144

The dosage form of embodiment 142 or 143, wherein the bioavailability of zoledronic acid in the disodium salt form is improved by at least about 10% as compared to an otherwise identical dosage form containing zoledronic acid in the diacid form.

Embodiment 145

The dosage form of embodiment 142, 143, or 144, containing at least about 20 mole % less of the disodium salt form as compared to the amount of the zoledronic acid in the diacid form that would be present if the zoledronic acid were in the diacid form.

Embodiment 146

The dosage form of embodiment 142, wherein the disodium salt form is present in an amount, on a molar basis, that has a value of about 0.9nd to about 1.1nd, wherein:

$n_d = (b_a/b_d)(n_a)$ wherein $b_a$ is the bioavailability of the diacid form, $b_d$ is the bioavailability of the disodium salt form, and $n_a$ is the number of moles of the diacid form that would be present if the zoledronic acid were in the diacid form.

Embodiment 147

The dosage form of embodiment 146, wherein the disodium salt is administered in an amount that has a value of about $n_d$.

Embodiment 148

The method of any of embodiments 1-39, 62-77, and 120-136, wherein:
only a single oral dosage form is administered; or
a first oral dosage form is administered, and a second oral dosage form is administered after the first oral dosage form, wherein the second oral dosage form is administered before the maximum pain relieving effect of the first oral dosage form is achieved, or the second oral dosage form is administered before an observable pain relieving effect is achieved.

Embodiment 149

The method of embodiment 148, wherein the second oral dosage form is administered before an observable pain relieving effect is achieved.

Embodiment 150

The method of any of embodiments 1-39, 62-77, and 120-132, wherein a first dosage form is administered, followed by administration of a second dosage form, wherein the second dosage form is administered after the maximum pain relieving effect of the first oral dosage form is achieved, and the second oral dosage form is administered while a pain relieving effect from the first oral dosage form is observable.

Embodiment 151

The method of embodiment 148, 149, or 150, wherein the second oral dosage form is administered about 24 hours to about 28 days after the first oral dosage form is administered.

Embodiment 152

The method of any of embodiments 20-39, wherein the human being is about 30 years old to about 75 years old.

Embodiment 153

The method of any of embodiments 20-39, wherein the human being is about 1 year old to about 16 years old.

Embodiment 154

The method of any of embodiments 20-39, wherein the human being is about 80 years old to about 95 years old.

Embodiment 155

The method of any of embodiments 20-39, wherein the human being has suffered from the arthritis for at least 2 months.

Embodiment 156

The method of any of embodiments 20-39, wherein the arthritis affects, a knee, an elbow, a wrist, a shoulder, or a hip.

Embodiment 157

The method of any of embodiments 1-44, 62-133, and 144-156, wherein the mammal or human being to which the zoledronic acid is administered does not eat food or drink beverage for at least 1 hour before the zoledronic acid is administered.

Embodiment 158

The method of embodiment 157, wherein the mammal or human being to which the zoledronic acid is administered does not eat food or drink beverage for at least 2 hours before the zoledronic acid is administered.

Embodiment 159

The method of embodiment 158, wherein the mammal or human being to which the zoledronic acid is administered does not eat food or drink beverage for at least 4 hours before the zoledronic acid is administered.

Embodiment 160

The method of embodiment 159, wherein the mammal or human being to which the zoledronic acid is administered does not eat food or drink beverage for at least 6 hours before the zoledronic acid is administered.

Embodiment 161

The method of any of embodiments 157-160, wherein the mammal or human being to which the zoledronic acid is administered does not eat food or drink beverage for at least 30 minutes after the zoledronic acid is administered.

Embodiment 162

The method of embodiment 161, wherein the mammal or human being to which the zoledronic acid is administered does not eat food or drink beverage for at least 1 hour after the zoledronic acid is administered.

Embodiment 163

The method of embodiment 161, where in the mammal or human being to which the zoledronic acid is administered does not eat food or drink beverage for at least 2 hours after the zoledronic acid is administered.

Embodiment 164

The method, dosage form, or product, of any preceding embodiment, wherein the zoledronic acid in the oral dosage form has a 24 hour sustained plasma level factor of about 1 or higher.

Embodiment 165

The method, dosage form, or product, of any preceding embodiment, wherein the zoledronic acid in the oral dosage form has a 24 hour sustained plasma level factor that is higher than that of intravenously administered zoledronic acid.

Embodiment 166

The method, dosage form, or product, of any preceding embodiment, wherein the oral dosage form is a solid that has a hardness of about 5 kPa to about 20 kPa.

Embodiment 167

A method of treating bone marrow lesions comprising: selecting a patient having a bone marrow lesion and OARSI grade 0 of joint space narrowing, and administering an inhibitor of osteoclast activity to the patient for the treatment of the bone marrow lesion.

Embodiment 168

The method of embodiment 167, wherein the inhibitor of osteoclast activity is administered at least twice.

Embodiment 169

The method of embodiment 167, wherein the inhibitor of osteoclast activity is administered about every three months, or more frequently.

Embodiment 170

The method of embodiment 167, wherein the inhibitor of osteoclast activity comprises a nitrogen-containing bisphosphonate.

Embodiment 171

The method of any one of embodiments 167-170, wherein the inhibitor of osteoclast activity is or comprises zoledronic acid.

Embodiment 172

The method of any one of embodiments 167-170, wherein the inhibitor of osteoclast activity is or comprises pamidronic acid.

Embodiment 173

The method of any one of embodiments 167-170, wherein the inhibitor of osteoclast activity is or comprises neridronic acid.

Embodiment 174

The method of any one of embodiments 167-170, wherein the inhibitor of osteoclast activity is or comprises olpadronic acid.

Embodiment 175

The method of any one of embodiments 167-170, wherein the inhibitor of osteoclast activity is or comprises alendronic acid.

Embodiment 176

The method of any one of embodiments 167-170, wherein the inhibitor of osteoclast activity is or comprises incadronic acid.

Embodiment 177

The method of any one of embodiments 167-170, wherein the inhibitor of osteoclast activity is or comprises ibandronic acid.

Embodiment 178

The method of any one of embodiments 167-170, wherein the inhibitor of osteoclast activity is or comprises risedronic acid.

Embodiment 179

The method of any one of embodiments 167-178, wherein the inhibitor of osteoclast activity is administered orally.

Embodiment 180

The method of any one of embodiments 167-178, wherein the inhibitor of osteoclast activity is administered intravenously.

Embodiment 181

The method of any one of embodiments 167-180, wherein the patient experiences a reduction in bone marrow lesion size that is at least about 100% greater than a reduction in bone marrow lesion size achieved with a placebo.

Embodiment 182

The method of any one of embodiments 167-180, wherein the patient experiences a reduction in bone marrow lesion size that is at least about 150% greater than a reduction in bone marrow lesion size achieved with a placebo.

Embodiment 183

The method of any one of embodiments 167-182, wherein the inhibitor of osteoclast activity is administered at least twice over a period of at least four weeks.

Embodiment 184

The method of any one of embodiments 167-183, wherein the inhibitor of osteoclast activity is administered once weekly for a period of six weeks.

Embodiment 185

The method of any one of embodiments 167-184, wherein the inhibitor of osteoclast activity comprises zoledronic acid, and the weekly dose is between about 25 mg and about 75 mg.

Embodiment 186

A method of treating knee pain comprising: selecting a patient having knee pain and OARSI grade 0 of joint space narrowing, and administering an inhibitor of osteoclast activity to the patient for the treatment of the knee pain.

Embodiment 187

The method of embodiment 186, wherein the inhibitor of osteoclast activity is administered at least twice.

Embodiment 188

The method of any one of embodiments 186-187, wherein the inhibitor of osteoclast activity is administered about every three months, or more frequently.

Embodiment 189

The method of any one of embodiments 186-188, wherein the inhibitor of osteoclast activity comprises a nitrogen-containing bisphosphonate.

Embodiment 190

The method of any one of embodiments 186-189, wherein the patient experiences pain relief three months after administration of the inhibitor of osteoclast activity.

Embodiment 191

The method of any one of embodiments 186-190, wherein the inhibitor of osteoclast activity is or comprises zoledronic acid.

Embodiment 192

The method of any one of embodiments 186-190, wherein the inhibitor of osteoclast activity is or comprises pamidronic acid.

Embodiment 193

The method of any one of embodiments 186-190, wherein the inhibitor of osteoclast activity is or comprises neridronic acid.

Embodiment 194

The method of any one of embodiments 186-190, wherein the inhibitor of osteoclast activity is or comprises olpadronic acid.

Embodiment 195

The method of any one of embodiments 186-190, wherein the inhibitor of osteoclast activity is or comprises alendronic acid.

Embodiment 196

The method of any one of embodiments 186-190, wherein the inhibitor of osteoclast activity is or comprises incadronic acid.

Embodiment 197

The method of any one of embodiments 186-190, wherein the inhibitor of osteoclast activity is or comprises ibandronic acid.

Embodiment 198

The method of any one of embodiments 186-190, wherein the inhibitor of osteoclast activity is or comprises risedronic acid.

Embodiment 199

The method of any one of embodiments 186-198, wherein the patient experiences a reduction in pain intensity—when using a 100 mm visual analog scale—of at least about 20.

Embodiment 200

A method of treating a bone marrow lesion of the knee comprising: selecting a patient having a bone marrow lesion of the knee and OARSI Grade 0 or Kellgren and Lawrence Grade 0 or Grade 1 of joint space narrowing, and administering an inhibitor of osteoclast activity to the patient for the treatment of the bone marrow lesion.

Embodiment 201

The method of embodiment 200, wherein the inhibitor of osteoclast activity is administered at least twice.

Embodiment 202

The method of embodiment 201, wherein the inhibitor of osteoclast activity is administered about every three months, or more frequently.

Embodiment 203

The method of embodiment 200, wherein the inhibitor of osteoclast activity comprises a nitrogen-containing bisphosphonate.

Embodiment 204

The method of embodiment 203, wherein the inhibitor of osteoclast activity is zoledronic acid.

Embodiment 205

The method of embodiment 203, wherein the inhibitor of osteoclast activity is pamidronic acid.

Embodiment 206

The method of embodiment 203, wherein the inhibitor of osteoclast activity is neridronic acid.

Embodiment 207

The method of embodiment 203, wherein the inhibitor of osteoclast activity is olpadronic acid.

Embodiment 208

The method of embodiment 203, wherein the inhibitor of osteoclast activity is minodronic acid.

Embodiment 209

The method of embodiment 203, wherein the inhibitor of osteoclast activity is incadronic acid.

Embodiment 210

The method of embodiment 203, wherein the inhibitor of osteoclast activity is ibandronic acid.

Embodiment 211

The method of embodiment 203, wherein the inhibitor of osteoclast activity is risedronic acid.

Embodiment 212

The method of embodiment 203, wherein the inhibitor of osteoclast activity is alendronic acid.

Embodiment 213

The method of embodiment 200, wherein the inhibitor of osteoclast activity is administered orally.

Embodiment 214

The method of embodiment 200, wherein the inhibitor of osteoclast activity is administered intravenously.

Embodiment 215

The method of embodiment 200, wherein the patient experiences a reduction in bone marrow lesion size that is at least about 15% within about 6 months after the inhibitor of osteoclast activity is administered to the patient.

Embodiment 216

The method of embodiment 200, wherein the patient experiences a reduction in bone marrow lesion size that is at least about 25% within about 6 months after the inhibitor of osteoclast activity is administered to the patient.

Embodiment 217

The method of embodiment 201, wherein the inhibitor of osteoclast activity is administered at least twice over a period of at least four weeks.

Embodiment 218

The method of embodiment 201, wherein the inhibitor of osteoclast activity is administered once weekly for a period of six weeks.

Embodiment 219

The method of embodiment 218, wherein the inhibitor of osteoclast activity comprises zoledronic acid, and the weekly dose is between about 25 mg and about 75 mg.

Embodiment 220

A method of treating knee pain comprising:
a. selecting a patient having knee pain, and:
  i. OARSI Grade 0 or Kellgren and Lawrence Grade 0 or Grade 1 of joint space narrowing, or
  ii. pain intensity of 5 or greater measured using the 0-10 NRS or 5 cm or greater using the 10 cm VAS; and
b. administering an inhibitor of osteoclast activity to the patient.

Embodiment 221

The method of embodiment 220, comprising selecting a patient having OARSI Grade 0 or Kellgren and Lawrence Grade 0 or Grade 1 of joint space narrowing.

Embodiment 222

The method of embodiment 220 or 221, comprising selecting a patient having pain intensity of 5 or greater measured using the 0-10 NRS or 5 cm or greater using the 10 cm VAS.

Embodiment 223

The method of embodiment 220, wherein the inhibitor of osteoclast activity is administered at least twice.

Embodiment 224

The method of embodiment 223, wherein the inhibitor of osteoclast activity is administered about every three months, or more frequently.

Embodiment 225

The method of embodiment 220, wherein the inhibitor of osteoclast activity comprises a nitrogen-containing bisphosphonate.

Embodiment 226

The method of embodiment 220, wherein the patient experiences pain relief within about three months after the inhibitor of osteoclast activity is administered to the patient.

Embodiment 227

The method of embodiment 226, wherein the patient experiences pain relief at least 24 hours after the inhibitor of osteoclast activity is administered to the patient.

Embodiment 228

The method of embodiment 220, wherein the inhibitor of osteoclast activity is zoledronic acid.

Embodiment 229

The method of embodiment 220, wherein the inhibitor of osteoclast activity is minodronic acid.

Embodiment 230

The method of embodiment 220, wherein the inhibitor of osteoclast activity is neridronic acid.

Embodiment 231

The method of embodiment 220, wherein the inhibitor of osteoclast activity is olpadronic acid.

Embodiment 232

The method of embodiment 220, wherein the inhibitor of osteoclast activity is alendronic acid.

Embodiment 233

The method of embodiment 220, wherein the inhibitor of osteoclast activity is incadronic acid.

Embodiment 234

The method of embodiment 220, wherein the inhibitor of osteoclast activity is ibandronic acid.

Embodiment 235

The method of embodiment 220, wherein the inhibitor of osteoclast activity is risedronic acid.

Embodiment 236

The method of embodiment 220, wherein the patient experiences a reduction in pain intensity—when using a 100 mm visual analog scale—of at least about 5.

Embodiment 237

The method of embodiment 220, wherein the inhibitor of osteoclast activity is administered at least twice over a period of at least four weeks.

Embodiment 238

The method of embodiment 220, wherein the inhibitor of osteoclast activity is administered once weekly for a period of six weeks.

Embodiment 239

The method of embodiment 238, wherein the inhibitor of osteoclast activity comprises zoledronic acid, and the weekly dose is between about 25 mg and about 75 mg.

Embodiment 240

A method of treating moderate to severe knee pain comprising administering an inhibitor of osteoclast activity to a person suffering from moderate to severe knee pain.

Embodiment 241

The method of embodiment 240, wherein the person suffering from moderate to severe knee pain has a normal joint space in the knee.

Embodiment 242

The method of embodiment 240, wherein the inhibitor of osteoclast activity is administered at least twice.

Embodiment 243

The method of embodiment 240, wherein the inhibitor of osteoclast activity is administered about every three months, or more frequently.

Embodiment 244

The method of embodiment 240, wherein the inhibitor of osteoclast activity comprises a nitrogen-containing bisphosphonate.

Embodiment 245

The method of embodiment 240, wherein the patient experiences pain relief within about three months after the inhibitor of osteoclast activity is administered to the patient.

Embodiment 246

The method of embodiment 245, wherein the patient experiences pain relief at least 24 hours after the inhibitor of osteoclast activity is administered to the patient.

Embodiment 247

The method of embodiment 240, wherein the inhibitor of osteoclast activity is zoledronic acid.

Embodiment 248

The method of embodiment 240, wherein the inhibitor of osteoclast activity is minodronic acid.

Embodiment 249

The method of embodiment 240, wherein the inhibitor of osteoclast activity is neridronic acid.

Embodiment 250

The method of embodiment 240, wherein the inhibitor of osteoclast activity is olpadronic acid.

Embodiment 251

The method of embodiment 240, wherein the inhibitor of osteoclast activity is alendronic acid.

Embodiment 252

The method of embodiment 240, wherein the inhibitor of osteoclast activity is incadronic acid.

Embodiment 253

The method of embodiment 240, wherein the inhibitor of osteoclast activity is ibandronic acid.

Embodiment 254

The method of embodiment 240, wherein the inhibitor of osteoclast activity is risedronic acid.

Embodiment 255

The method of embodiment 240, wherein the patient experiences a reduction in pain intensity—when using a 100 mm visual analog scale—of at least about 5.

Embodiment 256

The method of embodiment 240, wherein the inhibitor of osteoclast activity is administered at least twice over a period of at least four weeks.

Embodiment 257

The method of embodiment 240, wherein the inhibitor of osteoclast activity is administered once weekly for a period of six weeks.

Embodiment 258

The method of embodiment 257, wherein the inhibitor of osteoclast activity comprises zoledronic acid, and the weekly dose is between about 25 mg and about 75 mg.

Embodiment 259

A method of safely delivering zoledronic acid to the blood of a mammal through repeated oral administration comprising:
 orally administering about 0.4 mg/kg to about 4 mg/kg of zoledronic acid to the mammal no more frequently than once a day and more frequently than once a week; or
 orally administering about 0.4 mg/kg to about 10 mg/kg to the mammal once a week, or less frequently.

Embodiment 260

The method of any preceding embodiment, such as embodiment 259, wherein about 0.5 mg/kg to about 2 mg/kg is orally administered to the mammal daily.

Embodiment 261

The method of any preceding embodiment, such as embodiment 260, wherein about 0.6 mg/kg to about 0.9 mg/kg is orally administered to the mammal daily.

Embodiment 262

The method of any preceding embodiment, such as embodiment 259, wherein about 0.5 mg/kg to about 2 mg/kg is orally administered to the mammal weekly.

Embodiment 263

The method of any preceding embodiment, such as embodiment 263, wherein about 0.6 mg/kg to about 0.9 mg/kg is orally administered to the mammal weekly.

Embodiment 264

The method of any preceding embodiment, such as embodiment 259, 260, 261, 262, or 263, wherein zoledronic acid is orally administered about 3 to about 10 times.

Embodiment 265

The method of any preceding embodiment, such as embodiment 259, 260, 261, 262, 263, or 264, wherein zoledronic acid is orally administered in a dosage form comprising more than about 10% zoledronic acid by weight.

Embodiment 266

The method of any preceding embodiment, such as embodiment 259, 260, 261, 262, 263, 264, or 265, wherein zoledronic acid is administered in a manner and amount that results in the mammal having an $AUC_{0-24}$ of zoledronic acid that is about 50 ng·h/mL to about 500 ng·h/mL with each administration of zoledronic acid.

Embodiment 267

The method of any preceding embodiment, such as embodiment 266, wherein zoledronic acid is administered in a manner and amount that results in the mammal having an $AUC_{0-24}$ of zoledronic acid that is about 100 ng·h/mL to about 500 ng·h/mL with each administration of zoledronic acid.

Embodiment 268

A method of preparing an oral dosage form that is safe for repeated administration to a mammal comprising combining zoledronic acid with an excipient that is pharmaceutically acceptable to the mammal, wherein the amount of zoledronic acid that is combined with the excipient is such that zoledronic acid is present in the oral dosage form in an amount that is 0.4 mg/kg to about 10 mg/kg based upon the weight of the mammal.

Embodiment 269

The method of any preceding embodiment, such as embodiment 268, wherein the amount of zoledronic acid that is combined with the excipient is such that the oral dosage form comprises more than about 10% zoledronic acid by weight.

Embodiment 270

The method of any preceding embodiment, such as embodiment 268 or 269, wherein the amount of zoledronic acid that is combined with the excipient is such that zoledronic acid is present in the oral dosage form in an amount that is 0.4 mg/kg to about 3 mg/kg based upon the weight of the mammal.

Embodiment 271

The method of any preceding embodiment, such as embodiment 270, wherein the amount of zoledronic acid that is combined with the excipient is such that zoledronic acid is present in the oral dosage form in an amount that is 0.4 mg/kg to about 1.5 mg/kg based upon the weight of the mammal.

Embodiment 272

The method of any preceding embodiment, such as embodiment 270, wherein the amount of zoledronic acid that is combined with the excipient is such that zoledronic acid is present in the oral dosage form in an amount that is 0.6 mg/kg to about 0.9 mg/kg based upon the weight of the mammal.

Embodiment 273

The method of any preceding embodiment, such as embodiment 268, 269, 270, 271, or 272, wherein the oral dosage form is safe for once daily administration of the oral dosage form for about 3 to about 10 days.

Embodiment 274

The method of any preceding embodiment, such as embodiment 268, 269, 270, 271, or 272, wherein the oral dosage form is safe for once weekly administration of the oral dosage form for about 3 to about 10 weeks.

Embodiment 275

A method of safely delivering zoledronic acid to the blood of a mammal through repeated oral administration comprising:
  orally administering about 0.05 mg/kg to about 4 mg/kg of zoledronic acid to the mammal no more frequently than once a day and more frequently than once a week; or
  orally administering about 0.1 mg/kg to about 10 mg/kg to the mammal once a week, or less frequently
  wherein zoledronic acid is orally administered at least 5 times.

Embodiment 276

The method of any preceding embodiment, such as embodiment 275, wherein zoledronic acid is orally administered about 5 to about 10 times.

Embodiment 277

The method of any preceding embodiment, such as embodiment 275 or 276, wherein zoledronic acid is orally administered in a dosage form comprising more than about 10% zoledronic acid by weight.

Embodiment 278

The method of any preceding embodiment, such as embodiment 259, 260, 261, 262, 263, 264, 265, 266, 267, 268, 269, 270, 271, 272, 273, 274, 275, 276, or 277, wherein the mammal is a human being.

Embodiment 279

The method of any preceding embodiment, such as embodiment 259, 260, 261, 262, 263, 264, 265, 266, 267, 268, 269, 270, 271, 272, 273, 274, 275, 276, 277, or 278, wherein about 50 mg to about 350 mg of oral zoledronic acid is administered to the mammal per month.

Embodiment 280

An oral dosage form prepared by the method of any preceding embodiment, such as embodiment 259, 260, 261, 262, 263, 264, 265, 266, 267, 268, 269, 270, 271, 272, 273, 274, 275, 276, 277, 278, or 279.

Embodiment 281

An oral dosage form prepared by the method of any preceding embodiment, wherein an osteoclast inhibitor, including a bisphosphonate, such as zoledronic acid, neridronic acid, etc., is in a dosage form containing one of, or a combination of, the ingredients in the Table E.

Embodiment 282

A molecular complex comprising zoledronic acid or neridronic acid in an acid or a salt form.

Embodiment 283

The molecular complex of Embodiment 282, further comprising a basic or a salt form of a) an amine, b) an amide, or c) ammonium.

Embodiment 284

The molecular complex of Embodiment 283, wherein the molecular complex comprises ammonia in a salt form.

Embodiment 285

The molecular complex of Embodiment 283, wherein the amine is an amino acid.

Embodiment 286

The molecular complex of Embodiment 285, wherein the amino acid is a lysine.

Embodiment 287

The molecular complex of Embodiment 285, wherein the amino acid is L-lysine.

Embodiment 288

The molecular complex of Embodiment 285, wherein the amino acid is D-lysine.

Embodiment 289

The molecular complex of Embodiment 285, wherein the amino acid is DL-lysine.

Embodiment 290

The molecular complex of Embodiment 285, wherein the amino acid is a glycine.

Embodiment 291

The molecular complex of Embodiment 285, wherein the amino acid is L-glycine.

Embodiment 292

The molecular complex of Embodiment 285, wherein the amino acid is D-glycine.

Embodiment 293

The molecular complex of Embodiment 285, wherein the amino acid is DL-glycine.

Embodiment 294

The molecular complex of Embodiment 283, wherein the amide is nicotinamide.

Embodiment 295

The molecular complex of Embodiment 283, wherein the amine is adenine.

Embodiment 296

The molecular complex of Embodiment 285, wherein the amino acid (including the DL-mixture, a D-enantiomer, or an L-enantiomer) is alanine.

Embodiment 297

The molecular complex of Embodiment 285, wherein the amino acid (including the DL-mixture, a D-enantiomer, or an L-enantiomer) is arginine.

Embodiment 298

The molecular complex of Embodiment 285, wherein the amino acid (including the DL-mixture, a D-enantiomer, or an L-enantiomer) is asparagine.

Embodiment 299

The molecular complex of Embodiment 285, wherein the amino acid (including the DL-mixture, a D-enantiomer, or an L-enantiomer) is aspartic acid.

Embodiment 300

The molecular complex of Embodiment 285, wherein the amino acid (including the DL-mixture, a D-enantiomer, or an L-enantiomer) is cysteine.

Embodiment 301

The molecular complex of Embodiment 285, wherein the amino acid (including the DL-mixture, a D-enantiomer, or an L-enantiomer) is glutamic acid.

Embodiment 302

The molecular complex of Embodiment 285, wherein the amino acid (including the DL-mixture, a D-enantiomer, or an L-enantiomer) is glutamine.

Embodiment 303

The molecular complex of Embodiment 285, wherein the amino acid (including the DL-mixture, a D-enantiomer, or an L-enantiomer) is histidine.

Embodiment 304

The molecular complex of Embodiment 285, wherein the amino acid (including the DL-mixture, a D-enantiomer, or an L-enantiomer) is isoleucine.

Embodiment 305

The molecular complex of Embodiment 285, wherein the amino acid (including the DL-mixture, a D-enantiomer, or an L-enantiomer) is leucine.

Embodiment 306

The molecular complex of Embodiment 285, wherein the amino acid (including the DL-mixture, a D-enantiomer, or an L-enantiomer) is methionine.

Embodiment 307

The molecular complex of Embodiment 285, wherein the amino acid (including the DL-mixture, a D-enantiomer, or an L-enantiomer) is phenylalanine.

Embodiment 308

The molecular complex of Embodiment 285, wherein the amino acid (including the DL-mixture, a D-enantiomer, or an L-enantiomer) is proline.

Embodiment 309

The molecular complex of Embodiment 285, wherein the amino acid (including the DL-mixture, a D-enantiomer, or an L-enantiomer) is serine.

Embodiment 310

The molecular complex of Embodiment 285, wherein the amino acid (including the DL-mixture, a D-enantiomer, or an L-enantiomer) is threonine.

Embodiment 311

The molecular complex of Embodiment 285, wherein the amino acid (including the DL-mixture, a D-enantiomer, or an L-enantiomer) is tryptophan.

Embodiment 312

The molecular complex of Embodiment 285, wherein the amino acid (including the DL-mixture, a D-enantiomer, or an L-enantiomer) is tyrosine.

Embodiment 313

The molecular complex of Embodiment 285, wherein the amino acid (including the DL-mixture, a D-enantiomer, or an L-enantiomer) is valine.

Embodiment 314

A dosage form comprising the molecular complex of Embodiment 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, or 313.

Embodiment 315

The dosage form of Embodiment 314, which is an oral dosage form.

Embodiment 316

A method of treating pain, a musculoskeletal condition, or a condition related to bone or joint comprising administering a dosage form of Embodiment 314 or 315 to a mammal in need thereof.

Embodiment 317

The method of Embodiment 316, wherein the mammal is a human being.

Embodiment 318

The method of Embodiment 316 or 317, comprising treating acute pain, central pain, radio-therapy or chemo-therapy associated neuropathy, ankylosing spondylitis, arthritis, axial spondyloarthritis, blood cancers, bone fracture, bone metastases from solid tumors, bone metastasis, breast cancer, cancer, central multiple sclerosis pain, Charcot's foot, chronic pain, complex regional pain syndrome, diabetic peripheral neuropathy, erosive osteoarthritis, excessive bone resorption, fibrous dysplasia, giant cell tumor of bone, HIV-associated neuropathy, hypercalcemia of malignancy, inflammatory pain, juvenile rheumatoid arthritis, leukemias, low back pain, lumbar nerve root compression, lumbosacral pain, lung cancer, metastatic bone cancer, monoradiculopathies, multiple myeloma, musculoskeletal pain, neuropathic arthropaties, neuropathic pain, non-articular rheumatism, osteoarthritis, osteogenesis imperfecta, osteoporosis, Paget's disease, Paget's disease of bone, periarticular disorders, phantom limb pain, post-herpetic neuralgia, postoperative pain, post-stroke pain, prostate cancer, rheumatoid arthritis, SAPHO syndrome, sero-negative (non-rheumatoid) arthropathies, solid tumors or cancers, spinal cord injury, systemic lupus erythematosus, transient osteoarthritis of the hip, transient osteoporosis, transient osteoporosis of the hip, trigeminal neuralgia, tumor induced hypocalcemia, or vertebral crush fracture.

Embodiment 319

The method of Embodiment 316 or 317, comprising treating arthritis.

Embodiment 320

The method of Embodiment 319, comprising relieving pain associated with arthritis.

Embodiment 321

The method of Embodiment 320, wherein the arthritis affects a knee, an elbow, a wrist, a shoulder, or a hip.

Embodiment 322

The method of Embodiment 321, wherein the arthritis affects a knee.

Embodiment 323

The method of Embodiment 316 or 317, comprising treating musculoskeletal pain.

Embodiment 324

The method of Embodiment 316 or 317, comprising treating a bone marrow lesion.

Embodiment 325

The method of Embodiment 324, wherein the mammal is a human being that experiences a reduction in bone marrow lesion size that is at least about 15% within about 6 months after the inhibitor of osteoclast activity is administered to the human being.

Embodiment 326

The method of Embodiment 324, wherein the mammal is a human being that experiences a reduction in bone marrow lesion size that is at least about 25% within about 6 months after the inhibitor of osteoclast activity is administered to the human being.

Embodiment 327

The method of Embodiment 324, 325, or 326, wherein the bone marrow lesion affects a knee.

Embodiment 328

The method of Embodiment 324, 325, 326, or 327, comprising treating a bone marrow lesion of the knee by selecting a patient having a bone marrow lesion of the knee and OARSI Grade 0 or Kellgren and Lawrence Grade 0 or Grade 1 of joint space narrowing, and administering the dosage form to the patient for the treatment of the bone marrow lesion.

Embodiment 329

The method of Embodiment 316 or 317, comprising treating osteoarthritis.

Embodiment 330

The method of Embodiment 329, wherein the osteoarthritis affects a knee.

Embodiment 331

The method of Embodiment 329 or 330, comprising treating an osteolytic lesion associated with osteoarthritis.

Embodiment 332

The method of Embodiment 316, 317, 318, 319, 320, 321, 322, 323, 324, 325, 326, 327, 328, 329, 330, or 331, comprising treating knee pain.

Embodiment 333

The method of Embodiment 332, comprising treating moderate to severe knee pain.

Embodiment 334

The method of Embodiment 332 or 333, wherein the mammal is a human being that has a normal joint space in the knee.

Embodiment 335

The method of Embodiment 332, comprising treating knee pain by:
1) selecting a patient having knee pain, and:
   a. OARSI Grade 0 or Kellgren and Lawrence Grade 0 or Grade 1 of joint space narrowing, or
   b. pain intensity of 5 or greater measured using the 0-10 NRS, or 5 cm or greater using the 10 cm VAS; and
2) administering the dosage form to the patient.

Embodiment 336

The method of Embodiment 335, comprising selecting a patient having OARSI Grade 0 or Kellgren and Lawrence Grade 0 or Grade 1 of joint space narrowing.

Embodiment 337

The method of Embodiment 335, comprising selecting a patient having pain intensity of 5 or greater measured using the 0-10 NRS, or 5 cm or greater using the 10 cm VAS.

Embodiment 338

The method of Embodiment 335, 336, or 337, wherein the patient experiences a reduction in pain intensity—when using a 100 mm visual analog scale—of at least about 5 mm.

Embodiment 339

The method of Embodiment 316 or 317, comprising treating musculoskeletal pain.

Embodiment 340

The method of Embodiment 316 or 317, comprising treating inflammatory pain.

Embodiment 341

The method of Embodiment 316 or 317, comprising treating back pain.

Embodiment 342

The method of Embodiment 341, wherein the back pain comprises low back pain.

Embodiment 343

The method of Embodiment 342, wherein the low back pain is related to a vertebral change.

Embodiment 344

The method of Embodiment 316 or 317, comprising treating type 1 Modic changes, or type 1 and type 2 Modic changes.

Embodiment 345

The method of Embodiment 344, wherein the Modic change is located at C1/2, C2/3, C3/4, C4/5, C5/6, or C6/7.

Embodiment 346

The method of Embodiment 344, wherein the Modic change is located at C7/T1, T1/2, T2/3, T3/4, T4/5, T5/6, T6/7, T7/8, T8/9, T9/10, T10/11, or T11/12.

Embodiment 347

The method of Embodiment 344, wherein the Modic change is located at T12/L1, L1/2, L2/3, L3/4, L4/5, or L5/S1.

Embodiment 348

The method of Embodiment 316 or 317, comprising treating pain in an extremity.

Embodiment 349

The method of Embodiment 316 or 317, comprising treating joint pain.

Embodiment 350

The method of Embodiment 316 or 317, comprising treating muscle pain.

Embodiment 351

The method of Embodiment 316 or 317, comprising treating neuropathic pain.

Embodiment 352

The method of Embodiment 316 or 317, comprising treating complex regional pain syndrome.

Embodiment 353

The method of Embodiment 352, wherein the complex regional pain syndrome is complex regional pain syndrome type I.

Embodiment 354

The method of Embodiment 352, wherein the complex regional pain syndrome is complex regional pain syndrome type II.

Embodiment 355

The method of Embodiment 316 or 317, comprising treating Paget's disease of bone.

Embodiment 356

The method of Embodiment 316 or 317, comprising treating multiple myeloma.

Embodiment 357

The method of Embodiment 316 or 317, comprising treating ankylosing spondylitis.

Embodiment 358

The method of Embodiment 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, or 357, wherein the dosage form is administered about every three months, or more frequently.

Embodiment 359

The method of Embodiment 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, or 358, wherein the mammal experiences pain relief at least 24 hours after the dosage form is administered to the mammal.

Embodiment 360

The method of Embodiment 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, or 359, wherein the mammal experiences pain relief three months after the dosage form is administered.

Embodiment 361

The method of Embodiment 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, or 360, wherein the human being experiences pain relief that lasts for a duration of at least 48 hours after administration of the dosage form.

Embodiment 362

The method of Embodiment 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, or 361, wherein the human being receives the dosage form no more often than once daily.

Embodiment 363

The method of Embodiment 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, or 361, wherein there is a period of about 24 hours to about 7 days between administration of dosage forms.

Embodiment 364

The method of Embodiment 363, wherein the dosage form is administered weekly.

Embodiment 365

The method of Embodiment 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, or 361, wherein there is a period of about 14 days to about 28 days between administration of dosage forms.

Embodiment 366

The method of Embodiment 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, or 361, wherein there is a period of at least one month between administration of dosage forms.

Embodiment 367

The method of Embodiment 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, or 361, wherein there is a period of about 7 days to about 14 days between administration of dosage forms.

Embodiment 368

The method of Embodiment 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, or 367, wherein the compound is administered more than once.

Embodiment 369

The method, composition, molecular complex, dosage form, or product, of any preceding embodiment, wherein zoledronic acid or neridronic acid decreases osteoclast activity and/or CTX serum levels.

Embodiment 370

The method, composition, molecular complex, dosage form, or product, of any preceding embodiment, wherein zoledronic acid or neridronic acid decreases osteoclast activity by at least about 5%.

Embodiment 371

The method, composition, molecular complex, dosage form, or product, of any preceding embodiment, wherein zoledronic acid or neridronic acid decreases osteoclast activity by at least about 10%.

Embodiment 372

The method, composition, molecular complex, dosage form, or product, of any preceding embodiment, wherein zoledronic acid or neridronic acid decreases osteoclast activity by at least about 15%.

Embodiment 373

The method, composition, molecular complex, dosage form, or product, of any preceding embodiment, wherein zoledronic acid or neridronic acid decreases osteoclast activity by at least about 20%.

Embodiment 374

The method, composition, molecular complex, dosage form, or product, of any preceding embodiment, wherein zoledronic acid or neridronic acid decreases osteoclast activity by at least about 25%.

Embodiment 375

The method, composition, molecular complex, dosage form, or product, of any preceding embodiment, wherein zoledronic acid or neridronic acid decreases osteoclast activity by at least about 30%.

Embodiment 376

The method, composition, molecular complex, dosage form, or product, of any preceding embodiment, wherein zoledronic acid or neridronic acid decreases osteoclast activity by at least about 35%.

Embodiment 377

The method, composition, molecular complex, dosage form, or product, of any preceding embodiment, wherein zoledronic acid or neridronic acid decreases osteoclast activity by at least about 40%.

Embodiment 378

The method, composition, molecular complex, dosage form, or product, of any preceding embodiment, wherein zoledronic acid or neridronic acid decreases osteoclast activity by at least about 45%.

Embodiment 379

The method, composition, molecular complex, dosage form, or product, of any preceding embodiment, wherein zoledronic acid or neridronic acid decreases osteoclast activity by at least about 50%.

Embodiment 380

The method, composition, molecular complex, dosage form, or product, of any preceding embodiment, wherein zoledronic acid or neridronic acid decreases osteoclast activity by at least about 55%.

Embodiment 381

The method, composition, molecular complex, dosage form, or product, of any preceding embodiment, wherein zoledronic acid or neridronic acid decreases osteoclast activity by at least about 60%.

Embodiment 382

The method, composition, molecular complex, dosage form, or product, of any preceding embodiment, wherein zoledronic acid or neridronic acid decreases osteoclast activity by about 60%-70%.

Embodiment 383

The method, composition, molecular complex, dosage form, or product, of any preceding embodiment, wherein zoledronic acid or neridronic acid decreases osteoclast activity by about 70%-80%.

Embodiment 384

The method, composition, molecular complex, dosage form, or product, of any preceding embodiment, wherein zoledronic acid or neridronic acid decreases osteoclast activity by at least about 70%.

Embodiment 385

The method, composition, molecular complex, dosage form, or product, of any preceding embodiment, wherein zoledronic acid or neridronic acid decreases osteoclast activity by at about 75%.

Embodiment 386

The method, composition, molecular complex, dosage form, or product, of any preceding embodiment, wherein zoledronic acid or neridronic acid decreases osteoclast activity by about 80%-90%.

Embodiment 387

The method, composition, molecular complex, dosage form, or product, of any preceding embodiment, wherein zoledronic acid or neridronic acid decreases osteoclast activity by at least about 80%.

Embodiment 388

The method, composition, molecular complex, dosage form, or product, of any preceding embodiment, wherein zoledronic acid or neridronic acid decreases osteoclast activity by at least about 85%.

Embodiment 389

The method, composition, molecular complex, dosage form, or product, of any preceding embodiment, wherein zoledronic acid or neridronic acid decreases osteoclast activity by about 80%-85%.

Embodiment 390

The method, composition, molecular complex, dosage form, or product, of any preceding embodiment, wherein zoledronic acid or neridronic acid decreases osteoclast activity by at least about 90%.

Embodiment 391

The method, composition, molecular complex, dosage form, or product, of any preceding embodiment, wherein zoledronic acid or neridronic acid decreases osteoclast activity by about 85%-90%.

Embodiment 392

The method, composition, molecular complex, dosage form, or product, of any preceding embodiment, wherein zoledronic acid or neridronic acid decreases osteoclast activity by about 85%-95%.

Embodiment 393

The method, composition, molecular complex, dosage form, or product, of any preceding embodiment, wherein zoledronic acid or neridronic acid decreases osteoclast activity by about 90%-95%.

Embodiment 394

The method, composition, molecular complex, dosage form, or product, of any preceding embodiment, wherein zoledronic acid or neridronic acid decreases osteoclast activity by at least about 95%.

Embodiment 395

The method, composition, molecular complex, dosage form, or product, of any preceding embodiment, wherein zoledronic acid or neridronic acid decreases osteoclast activity by at least about 99%.

Embodiment 396

The method, composition, molecular complex, dosage form, or product, of any preceding embodiment, wherein zoledronic acid or neridronic acid decreases osteoclast activity by at least about 100%.

Embodiment 397

The method, composition, molecular complex, dosage form, or product, of any preceding embodiment, wherein zoledronic acid or neridronic acid decreases CTX serum levels by at least about 5%.

Embodiment 398

The method, composition, molecular complex, dosage form, or product, of any preceding embodiment, wherein zoledronic acid or neridronic acid decreases CTX serum levels by at least about 10%.

Embodiment 399

The method, composition, molecular complex, dosage form, or product, of any preceding embodiment, wherein zoledronic acid or neridronic acid decreases CTX serum levels by at least about 15%.

Embodiment 400

The method, composition, molecular complex, dosage form, or product, of any preceding embodiment, wherein zoledronic acid or neridronic acid decreases CTX serum levels by at least about 20%.

Embodiment 401

The method, composition, molecular complex, dosage form, or product, of any preceding embodiment, wherein zoledronic acid or neridronic acid decreases CTX serum levels by at least about 25%.

Embodiment 402

The method, composition, molecular complex, dosage form, or product, of any preceding embodiment, wherein zoledronic acid or neridronic acid decreases CTX serum levels by at least about 30%.

Embodiment 403

The method, composition, molecular complex, dosage form, or product, of any preceding embodiment, wherein zoledronic acid or neridronic acid decreases CTX serum levels by at least about 35%.

Embodiment 404

The method, composition, molecular complex, dosage form, or product, of any preceding embodiment, wherein zoledronic acid or neridronic acid decreases CTX serum levels by at least about 40%.

Embodiment 405

The method, composition, molecular complex, dosage form, or product, of any preceding embodiment, wherein zoledronic acid or neridronic acid decreases CTX serum levels by at least about 45%.

Embodiment 406

The method, composition, molecular complex, dosage form, or product, of any preceding embodiment, wherein zoledronic acid or neridronic acid decreases CTX serum levels by at least about 50%.

Embodiment 407

The method, composition, molecular complex, dosage form, or product, of any preceding embodiment, wherein zoledronic acid or neridronic acid decreases CTX serum levels by at least about 55%.

Embodiment 408

The method, composition, molecular complex, dosage form, or product, of any preceding embodiment, wherein zoledronic acid or neridronic acid decreases CTX serum levels by at least about 60%.

Embodiment 409

The method, composition, molecular complex, dosage form, or product, of any preceding embodiment, wherein zoledronic acid or neridronic acid decreases CTX serum levels by about 60%-70%.

Embodiment 410

The method, composition, molecular complex, dosage form, or product, of any preceding embodiment, wherein zoledronic acid or neridronic acid decreases CTX serum levels by about 70%-80%.

Embodiment 411

The method, composition, molecular complex, dosage form, or product, of any preceding embodiment, wherein zoledronic acid or neridronic acid decreases CTX serum levels by least about 70%.

Embodiment 412

The method, composition, molecular complex, dosage form, or product, of any preceding embodiment, wherein zoledronic acid or neridronic acid decreases CTX serum levels by at least about 75%.

Embodiment 413

The method, composition, molecular complex, dosage form, or product, of any preceding embodiment, wherein zoledronic acid or neridronic acid decreases CTX serum levels by at least about 80%.

Embodiment 414

The method, composition, molecular complex, dosage form, or product, of any preceding embodiment, wherein zoledronic acid or neridronic acid decreases CTX serum levels by at least about 85%.

Embodiment 415

The method, composition, molecular complex, dosage form, or product, of any preceding embodiment, wherein zoledronic acid or neridronic acid decreases CTX serum levels by about 80%-85%.

Embodiment 416

The method, composition, molecular complex, dosage form, or product, of any preceding embodiment, wherein zoledronic acid or neridronic acid decreases CTX serum levels by at least about 90%.

Embodiment 417

The method, composition, molecular complex, dosage form, or product, of any preceding embodiment, wherein zoledronic acid or neridronic acid decreases CTX serum levels by about 80%-90%.

Embodiment 418

The method, composition, molecular complex, dosage form, or product, of any preceding embodiment, wherein zoledronic acid or neridronic acid decreases CTX serum levels by about 85%-90%.

Embodiment 419

The method, composition, molecular complex, dosage form, or product, of any preceding embodiment, wherein zoledronic acid or neridronic acid decreases CTX serum levels by about 85%-95%.

Embodiment 420

The method, composition, molecular complex, dosage form, or product, of any preceding embodiment, wherein zoledronic acid or neridronic acid decreases CTX serum levels by about 90%-95%.

Embodiment 421

The method, composition, molecular complex, dosage form, or product, of any preceding embodiment, wherein zoledronic acid or neridronic acid decreases CTX serum levels by at least about 95%.

Embodiment 422

The method, composition, molecular complex, dosage form, or product, of any preceding embodiment, wherein zoledronic acid or neridronic acid decreases CTX serum levels by at least about 99%.

Embodiment 423

The method, composition, molecular complex, dosage form, or product, of any preceding embodiment, wherein zoledronic acid or neridronic acid decreases CTX serum levels by at least about 100%.

Embodiment 424

The method, dosage form, or product, of any preceding embodiment, wherein the zoledronic acid is orally administered in a manner that results in a 24 hour sustained plasma level factor that is at least 1.5 times that of 4 mg of zoledronic acid administered intravenously.

Unless otherwise indicated, all numbers expressing quantities of ingredients, properties such as molecular weight, reaction conditions, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A method of treating pain associated with complex regional pain syndrome, comprising orally administering zoledronic acid in an acid form or a salt form to a human being suffering from complex regional pain syndrome, wherein each time about 30 mg to about 100 mg of zoledronic acid in the salt form or the acid form, based upon the weight of the acid form, is administered at least twice approximately weekly until about 100 mg to about 320 mg of zoledronic acid in the salt or the acid form, based upon the weight of the acid form, have been administered to the human being, wherein the human being has suffered a traumatic event associated with the complex regional pain syndrome.

2. The method of claim 1, wherein about 50 mg of zoledronic acid in the salt form or the acid form, based upon the weight of the acid form, is administered to the human being approximately weekly.

3. The method of claim 2, wherein the zoledronic acid in the salt form or the acid form is administered at least 3 times.

4. The method of claim 3, wherein the zoledronic acid is administered in a disodium salt form.

5. The method of claim 1, wherein each orally administered dose contains about 50 mg to about 65 mg of the zoledronic acid in the disodium salt form.

6. The method of claim 5, wherein the zoledronic acid in the disodium salt form is administered 6 times.

7. The method of claim 1, wherein the pain is debilitating.

8. The method of claim 1, wherein, as a result of orally administering the zoledronic acid in the acid form or the salt form, the human being experiences a reduction in edema.

9. The method of claim 1, wherein, as a result of orally administering the zoledronic acid in an acid form or a salt form, an area affected by the complex regional pain syndrome experiences a reduction in temperature.

10. The method of claim 1, wherein the zoledronic acid in the acid form or the salt form is orally administered in a manner that results in a 24-hour sustained plasma level factor that is at least 1.5 times that of 4 mg of zoledronic acid administered intravenously.

11. The method of claim 1, wherein the zoledronic acid is orally administered in a manner that results in a 48-hour sustained plasma level factor that is at least five times that of 4 mg of zoledronic acid administered intravenously.

12. The method of claim 1, wherein the human being is not suffering from cancer or osteoporosis.

13. The method of claim 1, wherein the human being is not suffering from a solid tumor.

14. The method of claim 1, wherein the human being is not suffering from bone metastases.

15. The method of claim 1, wherein the human being is not suffering from a blood cancer.

16. The method of claim 1, wherein the human being is not suffering from a leukemia.

17. The method of claim 1, wherein the zoledronic acid is orally administered in a dosage form that, other than a sodium counter-ion to zoledronic acid, contains no agents which enhance the bioavailability of zoledronic acid.

18. The method of claim 1, wherein the zoledronic acid is orally administered in a dosage form that, other than a disodium salt of zoledronic acid, contains no agents which enhance the bioavailability of zoledronic acid.

19. The method of claim 1, wherein the zoledronic acid is orally administered in a dosage form that further comprises silicified microcrystalline cellulose, a crosslinked polyvinylpyrrolidone, a fumed silica, or magnesium stearate.

20. The method of claim 1, wherein the zoledronic acid in the acid form or the salt form is co-administered with steroid.

21. The method of claim 1, wherein the human being experiences a reduction in pain that lasts at least one month.

22. The method of claim 1, wherein the human being experiences a reduction in pain that lasts at least three months.

23. The method of claim 1, wherein the method reduces the use of a pain relief medication, other than the zoledronic acid, by the human being.

24. The method of claim 1, wherein the method reduces the use of a pain relief medication, other than the zoledronic acid, by the human being, about three months after orally administering the zoledronic acid.

25. The method of claim 1, wherein the method reduces the use of a pain relief medication, other than the zoledronic acid, by the human being, about one year after orally administering the zoledronic acid.

26. The method of claim 1, wherein the method reduces the use of a non-steroidal anti-inflammatory drug by the human being.

27. The method of claim 1, wherein the method reduces the use of a non-steroidal anti-inflammatory drug by the human being by at least about 50%.

28. The method of claim 4, wherein the zoledronic acid is administered in a dosage form containing at least 50% of the disodium salt form of zoledronic acid by weight.

29. The method of claim 1, wherein the zoledronic acid is orally administered in a solid dosage form having an enteric coating.

30. The method of claim 1, wherein the zoledronic acid is orally administered in a solid dosage form having a film coating.

\* \* \* \* \*